US009012722B2

(12) United States Patent
Narva et al.

(10) Patent No.: US 9,012,722 B2
(45) Date of Patent: Apr. 21, 2015

(54) NUCLEIC ACID MOLECULES THAT TARGET THE RHO1 SMALL GTP-BINDING PROTEIN AND CONFER RESISTANCE TO COLEOPTERAN PESTS

(75) Inventors: Kenneth Narva, Zionsville, IN (US); Huarong Li, Zionsville, IN (US); Chaoxian Geng, Zionsville, IN (US); Ignacio M. Larrinua, Indianapolis, IN (US); Monica B. Olson, Lebanon, IN (US); Navin Elango, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 338 days.

(21) Appl. No.: 13/341,752

(22) Filed: Dec. 30, 2011

(65) Prior Publication Data
US 2012/0174260 A1 Jul. 5, 2012

Related U.S. Application Data

(60) Provisional application No. 61/428,688, filed on Dec. 30, 2010.

(51) Int. Cl.
| C12N 15/113 | (2010.01) |
| A01H 1/00 | (2006.01) |
| C07K 14/435 | (2006.01) |
| A61K 31/713 | (2006.01) |
| C12N 15/82 | (2006.01) |

(52) U.S. Cl.
CPC ......... C07K 14/43563 (2013.01); A61K 31/713 (2013.01); C12N 15/8218 (2013.01); C12N 15/8286 (2013.01)

(58) Field of Classification Search
None
See application file for complete search history.

(56) References Cited

U.S. PATENT DOCUMENTS

| 7,612,194 | B2 * | 11/2009 | Andersen et al. ............ 536/24.5 |
| 7,943,819 | B2 | 5/2011 | Baum et al. |
| 2007/0050860 | A1 | 3/2007 | Andersen et al. |
| 2007/0124836 | A1 | 5/2007 | Baum et al. |
| 2010/0192265 | A1 | 7/2010 | Andersen et al. |
| 2011/0154545 | A1 | 6/2011 | Andersen et al. |
| 2012/0164205 | A1 * | 6/2012 | Baum et al. .................. 424/409 |
| 2012/0174258 | A1 | 7/2012 | Narva et al. |
| 2012/0174259 | A1 | 7/2012 | Narva et al. |
| 2012/0198586 | A1 | 8/2012 | Narva et al. |

FOREIGN PATENT DOCUMENTS

| WO | 2007011479 | 1/2007 |
| WO | 2007035650 | 3/2007 |
| WO | 2010147879 | 12/2010 |

OTHER PUBLICATIONS

Thomas et al, 2001, Plant J., 25:417-425.*
NCBI GenBank Accession No. XM_002198994: Predicted: Taeniopygia guttata ATPase, H+ transporting, lysosomal 42kDa, V1 subunit C1(LOC100218219), mRNA, Feb 25, 2009.
International Search Report and Written Opinion for International Application for PCT/US2011/068144, dated Sep. 12, 2012.
Klapholz, B., B. H. Dietrich, et al. (2009). "CAF-1 is required for efficient replication of euchromatic DNA in Drosophila larval endocycling cells." Chromosoma 118:235-248.
Oleson, J. D., Y. L. Park, et al. (2005 ). "Node-Injury Scale to Evaluate Root Injury by Corn Rootworms (Coleoptera: Chrysomelidae)." Journal of Economic Entomology 98:1-8.
Petolino, J. F. and N. L. Arnold (2009). Whiskers-mediated maize transformation. Methods in Molecular Biology; Transgenic Maize. M. P. Scott. Clifton, NJ, Humana Press. 526:59-67.
Tomoyasu, Y. and R. E. Denell (2004 ). "Larval RNAi in Tribolium (Coleoptera) for analyzing adult development. ." Developmental Genes and Evolution 214:575-578.
Vancanneyt, G., R. Schmidt, et al. (1990). "Construction of an intron-containing marker gene: Splicing of the intron in transgenic plants and its use in monitoring early events in Agrobacterium-mediated plant transformation" Molecular and General Genetics 220:245-250.
Wehrmann, A., A. Van Vliet, et al. (1996). "The similarities of bar and pat gene products make them equally applicable for plant engineers." Nature Biotechnology 14:1274-1278.
NCBI GenBank Accession No. XM_001951535: Predicted: Acyrthosiphon pisum similar to Caf1-180 CG1209-PB (Loc100161640), mRNA, Jul. 8, 2008.
International Search Report and Written Opinion for International Application for PCT/US2011/068062, dated Aug. 14, 2012.
International Search Report and Written Opinion for International Application for PCT/US2011/068188, dated Aug. 14, 2012.
International Search Report and Written Opinion for International Application for PCT/US2011/068162, dated Aug. 14, 2012.
Price, et al., "RNAi-mediated crop protection against insects" Trends in Biotechnology, May 22, 2008, pp. 393-400 ,vol. 26, No. 7.
Zhao, et al., "PsOr1, a potential target for RNA interference-based pest management" Insect Molecular Biology, Sep. 21, 2010, pp. 97-104, vol. 20, No. 1.
Allan, A. K., J. Du, et al., "Genome-wide survey of V-ATPase genes in Drosophila reveals a conserved renal phenotype for lethal alleles," Physiological Genomics, 2005, pp. 128-138, vol. 22.
Baum, James A., et al., "Control of coleopteran insect pests through RNA interference," Nature Biotechnology, 2007, pp. 1-5.
Bucher, G., J. Scholten, et al., "Parental RNAi in Tribolium (Coleoptera)," Current Biology, 2002, vol. 12:R85-R86.

(Continued)

Primary Examiner — Medina A Ibrahim
Assistant Examiner — Jason Deveau Rosen
(74) Attorney, Agent, or Firm — James Daly, IV; Trask Britt, P.C.

(57) ABSTRACT

This disclosure concerns nucleic acid molecules and methods of use thereof for control of coleopteran pests through RNA interference-mediated inhibition of target coding and transcribed non-coding sequences in coleopteran pests. The disclosure also concerns methods for making transgenic plants that express nucleic acid molecules useful for the control of coleopteran pests, and the plant cells and plants obtained thereby.

9 Claims, 5 Drawing Sheets

(56) References Cited

OTHER PUBLICATIONS

Davies, S. A., D. C. Kelly, et al., "Analysis and inactivation of vha55, the gene encoding the V-ATPase B-subunit in *Drosophila melanogaster*, reveals a larval lethal phenotype," Journal of Biological Chemistry, 1996, pp. 30677-30684, vol. 271.

Fox, D. T., C. C. F. Homem, et al., "Rho1 regulates *Drosophila* adherens junctions independently of p120ctn." Development, 2005, pp. 4819-4831, vol. 132.

Kadandale, P., J. D. Stender, et al., "Conserved role for autophagy in Rho1-mediated cortical remodeling and blood cell recruitment," Proceedings of the National Academy of Science USA, 2010, pp. 10502-10507, vol. 107.

Magie, C. R. and S. M. Parkhurst, "Rho1 regulates signaling events required for proper *Drosophila* embryonic development," Developmental Biology, 2005, pp. 144-154, vol. 278.

Rosales-Nieves, A. E., J. E. Johndrow, et al., "Coordination of microtubule and microfilament dynamics by *Drosophila* Rho1, Spire and Cappuccino," Nature Cell Biology, 2006, pp. 367-376, vol. 8.

Sambrook, J., E. F. Fritsch, et al., Eds., Molecular Cloning: A Laboratory Manual. Plainview, N. Y., Cold Spring Harbor Laboratory Press, 1989, 8 pages.

Shagin, D. A., E. V. Barsova, et al., "GFP-like proteins as ubiquitous metazoan superfamily: evolution of functional features and structural complexity," Molecular Biology and Evolution, 2004, pp. 841-850, vol. 21.

Song, Y., F. He, et al., "CAF-1 is essential for *Drosophila* development and involved in the maintenance of epigenetic memory," Developmental Biology, 2007, pp. 213-222, vol. 311.

Tyler, J. K., K. A. Collins, et al., "Interaction between the *Drosophila* CAF-1 and ASF1 Chromatin Assembly Factors," Molecular and Cellular Biology, 2001, pp. 6574-6584, vol. 21.

Vaccari, T., S. Duchi, et al., "The vacuolar ATPase is required for physiological as well as pathological activation of the Notch receptor," Development, 2010, pp. 1825-1832, vol. 137.

Xu, N., B. Keung, et al. "Rho GTPase controls invagination and cohesive migration of the *Drosophila* salivary gland through Crumbs and Rho-kinase," Developmental Biology, 2008, pp. 88-100, vol. 321.

Thomas et al, "Size constraints for targeting post-transcriptional gene silencing and for RNA-directed methylation in *Nicotiana benthamiana* using a potato virus X vector" 2001, Plant J. 25:417-425.

* cited by examiner

FIG. 5.

5'-(*sequence*)-(SEQ ID NO:4, 87, 88, 89, or 90)-(*sequence*)-3'

5'-(*sequence*)-( SEQ ID NO:4, 87, 88, 89, or 90)-(*sequence*)-(SEQ ID NO:1, 2, or 3)-(*sequence*)-3'

5'-(*sequence*)-(SEQ ID NO:1, 2, or 3)-(*sequence*)-(SEQ ID NO:4, 87, 88, 89, or 90)-(*sequence*)-3'

5'-(*sequence*)-( SEQ ID NO:4, 87, 88, 89, or 90)-(*sequence*)-(SEQ ID NO:4, 87, 88, 89, or 90)-(*sequence*)-3'

5'-(*sequence*)-( SEQ ID NO:4, 87, 88, 89, or 90)-(*sequence*)-(fragment of one of SEQ ID NO:1, 2, or 3)-(*sequence*)-3'

5'-(*sequence*)-(fragment of one of SEQ ID NO:1, 2, or 3)-(*sequence*)-(SEQ ID NO:4, 87, 88, 89, or 90)-(*sequence*)-3'

5'-(*sequence*)-(SEQ ID NO:4, 87, 88, 89, or 90)-(*sequence*)-(fragment of one of SEQ ID NO:1, 2, or 3)-(*sequence*)-(SEQ ID NO:2, 5, 6, or 7)-(*sequence*)-3'

5'-(*sequence*)-(fragment of one of SEQ ID NO:1, 2, or 3)-(*sequence*)-( SEQ ID NO:4, 87, 88, 89, or 90)-(*sequence*)-(fragment of one of SEQ ID NO:1, 2, or 3)-(*sequence*)-3'

Additional elements such as those contained in brackets "()" may be added to the 5' and 3' end of the nucleic acid molecule as desired.

SEQUENCE LISTING

<160> NUMBER OF SEQ ID NOS: 138

<210> SEQ ID NO 1
<211> LENGTH: 635
<212> TYPE: DNA
<213> ORGANISM: Diabrotica virgifera
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t

<400> SEQUENCE: 1

```
ttcggaagct tcatatttaa aagatctgtc atcaggaaag gctataggta aaagtctaaa      60
aacttggcca tatgaagaat ctcttgatga tgaaatcatt cttgttgatt tgggagaaac     120
tatttgcgaa gacaaatctg gccttcaaag acacaaagcc aagttttgt acttccatga     180 caatcgtaga cctgcatatt atggcacatg gaggaaaaaa agcaaatttg ttaaaccaag     240
aaaacctttg gctgaagata aaaaacattt ttaaattatg aaggtaggat ttcagatgat     300
gattgggagg aagaggaaca aggtgagtct mttaatggtt cagaagatga agctgagaag     360
gataatgacg atgacaagga tgattatgaa gttgataatg aattctttgt tccacatggg     420
cacttaagtg atgatgaggt ggatgatgaa gaactgagtc gtttanccc agattctttg     480 aaacaaaaac ttaaacttct taagaagag tttgatcaag atatgaagtc taaaactcag     540
aaactaaaga cctaggtcca tggtttgcat atggtnttaa caaagaataa gtagaggagt     600
atagtaggag gagagtgtgt gtagtatnta ctact                                 635
```

<210> SEQ ID NO 2
<211> LENGTH: 1387
<212> TYPE: DNA
<213> ORGANISM: Diabrotica virgifera
<220> FEATURE:
<221> NAME/KEY: misc_feature
<222> LOCATION: (1382)..(1382)
<223> OTHER INFORMATION: n is a, c, g, or t

<400> SEQUENCE: 2

```
agggcwgact cagttcattg gggagtggtt gaaagggggtg ttttttggag ttattccatt      60
atttgaagga gtgataaaga agatcttgga agccaccata gacttaattc acatagaacc     120
agcatacttt ctgatcacca agaagaaatg actgagtatt ggttgatatc tgccccaggg     180
gataagacct gtcaacagac atgggacacg atgaataata tgacaagtaa acagaataat     240
ttgtcaacca actacaagtt tcaaatcccg gacttgaaag ttggtactct ggatcagtta     300
gtaggacttt ctgatgatct gggcaagctt gatgggttcg tggagcaggt taccaggaag     360
gtagctcagt accttggaga agtacttgaa gaacagaggg acaagtggtc agaaaacctg     420
caggccaata acagcgattt gcccacttat ttaacccgat ttacttggga catcgccaaa     480
tatcccatca agcaatcgct ccgtaacatc gccgatataa tcagcaaaca agttggccaa     540
attgacgctg atctgaagac caaatcgtct gcgtacaata acttgaaagg aagtcttcag     600
aatttggaga gaaacagac aggaagttta ctaacaagaa acttggcaga tttggtgaaa     660
aaggaacatt ttatttttgga ttctgaatat ttgcagacat tgttggttat tgttccaaaa     720
```

-continued

```
gcccaattca acgaatggaa tgcgacatac gaaaagatta ccgacatgat agtccctcgt      780
tcttcacaac tgattaaaca ggataacgaa tacggtctat atactgtatc cctattcaaa      840
aaggtcgtcg aagaattcaa gttacacgct agagaaaaga agttcatcgt tcgtgatttc      900
atatataacg aagaggaact ggcagctgga agaacgaga taaccaaact cgtcaccgat       960
aaaaagaagc aatttggtcc attagttaga tggcttaaag tcaacttcag cgagtgtttc     1020
tgcgcctgga ttcacgttaa agcgttgagg gtatttgttg aatctgtttt aagatatggc     1080
ctcccgtcaa tttccaagct atttaatcc acccaataag caacaattaa acgtttaag      1140 agatgtcttg aaccaacttt acggccacct cgatagtagt gctgccctt caggacctaa      1200 cgttgatagc gttgacattc caggcctcgg attcggccaa tcagagtatt acccatacgt    1260
ttactacaag ctgaacgtcg acatgttaga atcgaagatc taaactcacg catcaatcca    1320
agagtttgtt attaataggt tccaaacaat tttaaaaaaa cgtacttacg caagtgagtg    1380 anaggcc                                                              1387

<210> SEQ ID NO 3
<211> LENGTH: 1701
<212> TYPE: DNA
<213> ORGANISM: Diabrotica virgifera

<400> SEQUENCE: 3
aattawattt tatacctcga tccaaaaata ttttcgcaaa attgtagtac actgaatttt       60
aactatcatg attgttccag atatgttggc tgctacaagt gtattgcagc aaagagctac      120
agatataaga aatcaacatg taaactggca atcctatttc cagtcacaaa tgatttcgca      180
ggaagactac aacttcatag tagcttttga tgtgactgat agtgcaaaaa gagaagctct      240
cctgaaaagc gacagaaacc aatgtgctca acattgttg aaccttttgg ggcatgtatc      300
caaggaccaa actctgcagt acattttagt tttggttgat gatatgttac aggagaacag      360
aagtcgtgta gagatatttc acgaatatgc caaccaaaag aaagaatctg tttggggtcc      420 attttgaac cttcttaacc gccaggatgg atttattacc aacatgactt ctaggatcat      480
cgctaaaatt gcttgttggt cgcagacact tatggatcgt tctgaccttc attttactt      540 gacctggtta aaagaccaac taaaaactca gaacaacgaa tacatccaat cggttgcaag      600
atgccttcaa atgatgctcc gaattgacga ctaccgtttt gccttcgtgt ccgtcgatgg      660
aatatccact ctgttgtcgg tactctctgg aagagtaaat ttccaagttc agtaccagct      720
gatattctgc ttgtgggtac tcactttcaa cccgttgtta gccgaaaaga tgaacaaatt      780
caacgttatt cctatattgg cagatatttt gagcgattcg gtaaaggaga agtaaccag      840 aattatttta gctgtttca ggaatttgat cgaaaaccc gaagatcaac aagtttcaaa      900
agaacattgt atagctatgg tgcaatgcaa agtattgaaa caattggcca ttttagaaca      960
gcgcaagttc gatgatgaag atgtgacagc tgatgtcgaa tttctaactg aaaaactaca     1020
gagttctgtt caggatctga gttccttcga tgaatattca actgaagtca atctggacg     1080 tttggaatgg tctccagtac acaagagcaa gttctggcgg aaaatgcgc agcgcctcaa    1140 cgagaaaaac tacgaattac tccgtattct cattcatttg ttagaaacca gcaaggaccc   1200
cttggtattg agcgtagcta gtttcgatat tggagagtat gttcgccatt atcctcgcgg   1260
caaacacata atcgagcagt tgggaggaaa gcaattagtt atgcaactct agcccacga     1320 agatcccaat gtacgatatg aagctctgtt ggcagtccaa aaattgatgg tccacaattg    1380
```

```
ggaataccctt ggtcgtcaac ttgaaaaaga gcaaagtaca gataaaaacg cgccaaaggg    1440
tggagctcct gtcgcaggca aggcgtaaat actaccatga aaagtattta aagatattta    1500
ctgcaataat tgtagaaact ttaaaaataa ttgtaaaaat tatatcgatt tctgtacata    1560
gctgtatagg tatacattcc tgtcatattt tattattgtt acgataacca ataatcaacc    1620
atgcacattt taaacattta aaaatattgc ttttaaagtt aamtttttt acttgtattg    1680 ttagtattat aataagtata t                                              1701
```

<210> SEQ ID NO 4
<211> LENGTH: 1001
<212> TYPE: DNA
<213> ORGANISM: Diabrotica virgifera

<400> SEQUENCE: 4

```
aaattggact aaacttttt gctcgtttwg ttaatcttat ccattaattt ctaaaattgt     60
atgattttgt tagaaagtgg tagaataacg ctaaccaatt taggagtaac actgcaaaga    120
gactctctga atgttttgtt gctgttccga taaggaggac tacggaaaat ttttgcttga    180
tccttatctg tctgttatcc ccgctcttac ttcgtaattt atttaatgtc cgccattttc    240
gttcgtagtt gaataggcgt taactttgtg tgttttggca ggtccgatgg ctgcaataag    300
aaaaaaattg gtgattgttg gtgacggagc atgtggaaaa acatgtcttt taatagtatt    360
tagtaaagat cagttcccag aagtatacgt gcccactgta ttcgaaaact atgtggcgga    420
tattgaagta gatggaaagc aggtagaact cgccttatgg gataccgcag gtcaagaaga    480
ttatgatcgt ctgcggcccc tttcatatcc agacaccgat gtgattttaa tgtgcttctc    540
agtagactcc cccgactcat tagaaaacat cccagaaaaa tggacccag aggtaaaaca     600 cttttgtcca aatgtgccaa ttattctggt aggcaataag aaggatctgc gtaacgatcc    660
caataccatt aacgaactta aaagatgaa acaagaacca gtaaaacctc aagacggaag     720
atccatggca gagaaaatca atgctttgc atatctagaa tgttctgcca aaagtaagga    780
gggtgtaaga gaggtttttg aaaatgctac ccgagctgca ctgcaagtca aaagaagaa     840 gaagccccgt tgtgtaatgt tttgagccac tacatattct atattttata ttaataatcg    900
ttacgtgtgt taattaattt actaagggg acgttctgtc atgatgtatt gacaagggg     960 cttctgcatg atgtattgac taacaaaaat aaaccccwtt a                       1001
```

<210> SEQ ID NO 5
<211> LENGTH: 338
<212> TYPE: DNA
<213> ORGANISM: Diabrotica virgifera

<400> SEQUENCE: 5

```
agggcwgact cagttcattg gggagtggtt gaaagggtg ttttttggag ttattccatt      60
atttgaagga gtgataaaga agatcttgga agccaccata gacttaattc acatagaacc    120
agcatacttt ctgatcacca agaagaaatg actgagtatt ggttgatatc tgccccaggg    180
gataagacct gtcaacagac atgggacacg atgaataata tgacaagtaa acagaataat    240
ttgtcaacca actacaagtt tcaaatcccg gacttgaaag ttggtactct ggatcagtta    300
gtaggacttt ctgatgatct gggcaagctt gatgggtt                            338
```

<210> SEQ ID NO 6
<211> LENGTH: 21
<212> TYPE: DNA
<213> ORGANISM: Diabrotica virgifera

```
<220> FEATURE:
<221> NAME/KEY: misc_feature
<222> LOCATION: (16)..(16)
<223> OTHER INFORMATION: n is a, c, g, or t

<400> SEQUENCE: 6
tacgcaagtg agtganaggc c                                              21

<210> SEQ ID NO 7
<211> LENGTH: 460
<212> TYPE: DNA
<213> ORGANISM: Diabrotica virgifera

<400> SEQUENCE: 7
agaagaaatg actgagtatt ggttgatatc tgccccaggg gataagacct gtcaacagac     60
atgggacacg atgaataata tgacaagtaa acagaataat ttgtcaacca actcaagtt    120 tcaaatcccg gacttgaaag ttggtactct ggatcagtta gtaggacttt ctgatgatct   180
gggcaagctt gatgggttcg tggagcaggt taccaggaag gtagctcagt accttggaga   240
agtacttgaa gaacagaggg acaagtggtc agaaaacctg caggccaata acagcgattt   300
gcccacttat ttaaccccgat ttacttggga catcgccaaa tatcccatca agcaatcgct   360
ccgtaacatc gccgatataa tcagcaaaca agttggccaa attgacgctg atctgaagac   420
caaatcgtct gcgtacaata acttgaaagg aagtcttcag                         460

<210> SEQ ID NO 8
<211> LENGTH: 500
<212> TYPE: DNA
<213> ORGANISM: Diabrotica virgifera

<400> SEQUENCE: 8
agaaacagac aggaagttta ctaacaagaa acttggcaga tttggtgaaa aaggaacatt     60
ttattttgga ttctgaatat ttgcagacat tgttggttat tgttccaaaa gcccaattca    120
acgaatggaa tgcgacatac gaaaagatta ccgacatgat agtccctcgt tcttcacaac   180
tgattaaaca ggataacgaa tacggtctat atactgtatc cctattcaaa aaggtcgtcg   240
aagaattcaa gttacacgct agagaaaaga agttcatcgt tcgtgatttc atatataacg   300
aagaggaact ggcagctgga aagaacgaga taaccaaact cgtcaccgat aaaaagaagc   360
aatttggtcc attagttaga tggcttaaag tcaacttcag cgagtgtttc tgcgcctgga   420
ttcacgttaa agcgttgagg gtatttgttg aatctgtttt aagatatggc ctcccgtcaa   480
tttccaagct attttaatcc                                              500

<210> SEQ ID NO 9
<211> LENGTH: 77
<212> TYPE: DNA
<213> ORGANISM: Diabrotica virgifera

<400> SEQUENCE: 9
aattawattt tataccctcga tccaaaaata ttttcgcaaa attgtagtac actgaattttt    60 aactatcatg attgttc                                                   77

<210> SEQ ID NO 10
<211> LENGTH: 445
<212> TYPE: DNA
<213> ORGANISM: Diabrotica virgifera

<400> SEQUENCE: 10
```

```
tcatgattgt tccagatatg ttggctgcta caagtgtatt gcagcaaaga gctacagata    60
taagaaatca acatgtaaac tggcaatcct atttccagtc acaaatgatt tcgcaggaag   120
actacaactt catagtagct tttgatgtga ctgatagtgc aaaaagagaa gctctcctga   180
aaagcgacag aaaccaatgt gctcaaacat tgttgaacct ttgggggcat gtatccaagg   240
accaaactct gcagtacatt ttagttttgg ttgatgatat gttacaggag aacagaagtc   300
gtgtagagat atttcacgaa tatgccaacc aaaagaaaga atctgtttgg ggtccatttt   360
tgaaccttct taaccgccag gatggattta ttaccaacat gacttctagg atcatcgcta   420
aaattgcttg ttggtcgcag acact                                         445
```

<210> SEQ ID NO 11
<211> LENGTH: 570
<212> TYPE: DNA
<213> ORGANISM: Diabrotica virgifera
<400> SEQUENCE: 11

```
agaacattgt atagctatgg tgcaatgcaa agtattgaaa caattggcca ttttagaaca    60
gcgcaagttc gatgatgaag atgtgacagc tgatgtcgaa tttctaactg aaaaactaca   120
gagttctgtt caggatctga gttccttcga tgaatattca actgaagtca aatctggacg   180
tttggaatgg tctccagtac acaagagcaa gttctggcgg aaaatgcgc agcgcctcaa    240 cgagaaaaac tacgaattac tccgtattct cattcatttg ttagaaacca gcaaggaccc   300
cttggtattg agcgtagcta gtttcgatat tggagagtat gttcgccatt atcctcgcgg   360
caaacacata atcgagcagt tgggaggaaa gcaattagtt atgcaactct tagcccacga   420
agatcccaat gtacgatatg aagctctgtt ggcagtccaa aaattgatgg tccacaattg   480
ggaatacctt ggtcgtcaac ttgaaaaaga gcaaagtaca gataaaaacg cgccaaaggg   540
tggagctcct gtcgcaggca aggcgtaaat                                    570
```

<210> SEQ ID NO 12
<211> LENGTH: 24
<212> TYPE: DNA
<213> ORGANISM: Artificial
<220> FEATURE:
<223> OTHER INFORMATION: T7 phage promoter sequence
<400> SEQUENCE: 12

```
ttaatacgac tcactatagg gaga                                           24
```

<210> SEQ ID NO 13
<211> LENGTH: 50
<212> TYPE: DNA
<213> ORGANISM: Artificial
<220> FEATURE:
<223> OTHER INFORMATION: Primer Caf-FT7

<400> SEQUENCE: 13

```
ttaatacgac tcactatagg gagattcgga agcttcatat ttaaaagatc                50
```

<210> SEQ ID NO 14
<211> LENGTH: 24
<212> TYPE: DNA
<213> ORGANISM: Artificial
<220> FEATURE:
<223> OTHER INFORMATION: Primer Caf-R
<400> SEQUENCE: 14

```
tatcttcagc caaaggtttt cttg                                           24
```

<210> SEQ ID NO 15
<211> LENGTH: 26
<212> TYPE: DNA
<213> ORGANISM: Artificial
<220> FEATURE:
<223> OTHER INFORMATION: Primer Caf-F

<400> SEQUENCE: 15
ttcggaagct tcatatttaa aagatc                                        26

<210> SEQ ID NO 16
<211> LENGTH: 48
<212> TYPE: DNA
<213> ORGANISM: Artificial
<220> FEATURE:
<223> OTHER INFORMATION: Primer Caf-RT7

<400> SEQUENCE: 16
ttaatacgac tcactatagg gagatatctt cagccaaagg ttttcttg                48

<210> SEQ ID NO 17
<211> LENGTH: 46
<212> TYPE: DNA
<213> ORGANISM: Artificial
<220> FEATURE:
<223> OTHER INFORMATION: Primer Atp.C-F1T7

<400> SEQUENCE: 17
ttaatacgac tcactatagg gagaagaaga aatgactgag tattgg                  46

<210> SEQ ID NO 18
<211> LENGTH: 20
<212> TYPE: DNA
<213> ORGANISM: Artificial
<220> FEATURE:
<223> OTHER INFORMATION: Primer Atp.C-R1

<400> SEQUENCE: 18
ctgaagactt cctttcaagt                                                20

<210> SEQ ID NO 19
<211> LENGTH: 22
<212> TYPE: DNA
<213> ORGANISM: Artificial
<220> FEATURE:
<223> OTHER INFORMATION: Primer Atp.C-F1

<400> SEQUENCE: 19
agaagaaatg actgagtatt gg                                             22

<210> SEQ ID NO 20
<211> LENGTH: 44
<212> TYPE: DNA
<213> ORGANISM: Artificial
<220> FEATURE:
<223> OTHER INFORMATION: Primer Atp.C-R1T7

<400> SEQUENCE: 20
ttaatacgac tcactatagg gagactgaag acttcctttc aagt                     44

<210> SEQ ID NO 21
<211> LENGTH: 48
<212> TYPE: DNA
<213> ORGANISM: Artificial
<220> FEATURE:

<223> OTHER INFORMATION: Primer Atp.C-R1shortT7

<400> SEQUENCE: 21
ttaatacgac tcactatagg gagagatggg atatttggcg atgtccca        48

<210> SEQ ID NO 22
<211> LENGTH: 24
<212> TYPE: DNA
<213> ORGANISM: Artificial
<220> FEATURE:
<223> OTHER INFORMATION: Primer Atp.C-R1short

<400> SEQUENCE: 22
gatgggatat ttggcgatgt ccca        24

<210> SEQ ID NO 23
<211> LENGTH: 46
<212> TYPE: DNA
<213> ORGANISM: Artificial
<220> FEATURE:
<223> OTHER INFORMATION: Atp.C-F2T7

<400> SEQUENCE: 23
ttaatacgac tcactatagg gagaagaaac agacaggaag tttact        46

<210> SEQ ID NO 24
<211> LENGTH: 25
<212> TYPE: DNA
<213> ORGANISM: Artificial
<220> FEATURE:
<223> OTHER INFORMATION: Primer Atp.C-R2

<400> SEQUENCE: 24
ggattaaaat agcttggaaa ttgac        25

<210> SEQ ID NO 25
<211> LENGTH: 22
<212> TYPE: DNA
<213> ORGANISM: Artificial
<220> FEATURE:
<223> OTHER INFORMATION: Primer Atp.C-F2

<400> SEQUENCE: 25
agaaacagac aggaagttta ct        22

<210> SEQ ID NO 26
<211> LENGTH: 49
<212> TYPE: DNA
<213> ORGANISM: Artificial
<220> FEATURE:
<223> OTHER INFORMATION: Primer Atp.C-R2T7

<400> SEQUENCE: 26
ttaatacgac tcactatagg gagaggatta aaatagcttg gaaattgac        49

<210> SEQ ID NO 27
<211> LENGTH: 48
<212> TYPE: DNA
<213> ORGANISM: Artificial
<220> FEATURE:
<223> OTHER INFORMATION: Primer Atp.H-F1T7

<400> SEQUENCE: 27
ttaatacgac tcactatagg gagatcatga ttgttccaga tatgttgg        48

```
<210> SEQ ID NO 28
<211> LENGTH: 20
<212> TYPE: DNA
<213> ORGANISM: Artificial
<220> FEATURE:
<223> OTHER INFORMATION: Primer Atp.H-R1

<400> SEQUENCE: 28
agtgtctgcg accaacaagc                                              20

<210> SEQ ID NO 29
<211> LENGTH: 24
<212> TYPE: DNA
<213> ORGANISM: Artificial
<220> FEATURE:
<223> OTHER INFORMATION: Primer Atp.H-F1

<400> SEQUENCE: 29
tcatgattgt tccagatatg ttgg                                         24

<210> SEQ ID NO 30
<211> LENGTH: 44
<212> TYPE: DNA
<213> ORGANISM: Artificial
<220> FEATURE:
<223> OTHER INFORMATION: Primer Atp.H-R1T7

<400> SEQUENCE: 30
ttaatacgac tcactatagg gagaagtgtc tgcgaccaac aagc                   44

<210> SEQ ID NO 31
<211> LENGTH: 46
<212> TYPE: DNA
<213> ORGANISM: Artificial
<220> FEATURE:
<223> OTHER INFORMATION: Primer Atp.H-F2T7

<400> SEQUENCE: 31
ttaatacgac tcactatagg gagaagaaca ttgtatagct atggtg                 46

<210> SEQ ID NO 32
<211> LENGTH: 20
<212> TYPE: DNA
<213> ORGANISM: Artificial
<220> FEATURE:
<223> OTHER INFORMATION: Primer Atp.H-R2

<400> SEQUENCE: 32
atttacgcct tgcctgcgac                                              20

<210> SEQ ID NO 33
<211> LENGTH: 22
<212> TYPE: DNA
<213> ORGANISM: Artificial
<220> FEATURE:
<223> OTHER INFORMATION: Primer Atp.H-F2

<400> SEQUENCE: 33
agaacattgt atagctatgg tg                                           22

<210> SEQ ID NO 34
<211> LENGTH: 44
<212> TYPE: DNA
<213> ORGANISM: Artificial
<220> FEATURE:
<223> OTHER INFORMATION: Primer Atp.H-R2T7
```

<400> SEQUENCE: 34
ttaatacgac tcactatagg gagaaatttac gccttgcctg cgac            44

<210> SEQ ID NO 35
<211> LENGTH: 46
<212> TYPE: DNA
<213> ORGANISM: Artificial
<220> FEATURE:
<223> OTHER INFORMATION: Primer Rho1-FT7

<400> SEQUENCE: 35
ttaatacgac tcactatagg gagacaggtc cgatggctgc aataag          46

<210> SEQ ID NO 36
<211> LENGTH: 20
<212> TYPE: DNA
<213> ORGANISM: Artificial
<220> FEATURE:
<223> OTHER INFORMATION: Primer Rho1-R

<400> SEQUENCE: 36
gacttgcagt gcagctcggg                                        20

<210> SEQ ID NO 37
<211> LENGTH: 22
<212> TYPE: DNA
<213> ORGANISM: Artificial
<220> FEATURE:
<223> OTHER INFORMATION: Primer Rho1-F

<400> SEQUENCE: 37
caggtccgat ggctgcaata ag                                     22

<210> SEQ ID NO 38
<211> LENGTH: 44
<212> TYPE: DNA
<213> ORGANISM: Artificial
<220> FEATURE:
<223> OTHER INFORMATION: Primer Rho1-RT7

<400> SEQUENCE: 38
ttaatacgac tcactatagg gagagacttg cagtgcagct cggg            44

<210> SEQ ID NO 39
<211> LENGTH: 39
<212> TYPE: DNA
<213> ORGANISM: Artificial
<220> FEATURE:
<223> OTHER INFORMATION: Primer hpCaf-F

<400> SEQUENCE: 39
gagaggtacc tcggaagctt catatttaaa agatctgtc                   39

<210> SEQ ID NO 40
<211> LENGTH: 42
<212> TYPE: DNA
<213> ORGANISM: Artificial
<220> FEATURE:
<223> OTHER INFORMATION: Primer hpCaf-R

<400> SEQUENCE: 40
ctctggatcc aaaatgtttt ttatcttcag ccaaaggttt tc               42

<210> SEQ ID NO 41
<211> LENGTH: 42

```
<212> TYPE: DNA
<213> ORGANISM: Artificial
<220> FEATURE:
<223> OTHER INFORMATION: Primer hp-invCaf-F

<400> SEQUENCE: 41
agagccatgg aaaatgtttt ttatcttcag ccaaaggttt tc                    42

<210> SEQ ID NO 42
<211> LENGTH: 39
<212> TYPE: DNA
<213> ORGANISM: Artificial
<220> FEATURE:
<223> OTHER INFORMATION: Primer hp-invCaf-R

<400> SEQUENCE: 42
ctctgagctc tcggaagctt catatttaaa agatctgtc                        39

<210> SEQ ID NO 43
<211> LENGTH: 43
<212> TYPE: DNA
<213> ORGANISM: Artificial
<220> FEATURE:
<223> OTHER INFORMATION: Primer ST-LS1-F

<400> SEQUENCE: 43
agagggatcc aggcctaggt atgtttctgc ttctaccttt gat                   43

<210> SEQ ID NO 44
<211> LENGTH: 47
<212> TYPE: DNA
<213> ORGANISM: Artificial
<220> FEATURE:
<223> OTHER INFORMATION: Primer ST-LS1-R

<400> SEQUENCE: 44
ctctccatgg accggtattt aaatacctgc acatcaccat gttttgg               47

<210> SEQ ID NO 45
<211> LENGTH: 40
<212> TYPE: DNA
<213> ORGANISM: Artificial
<220> FEATURE:
<223> OTHER INFORMATION: Primer hpATPaseC-F

<400> SEQUENCE: 45
agagggtacc agaagaaatg actgagtatt ggttgatatc                       40

<210> SEQ ID NO 46
<211> LENGTH: 32
<212> TYPE: DNA
<213> ORGANISM: Artificial
<220> FEATURE:
<223> OTHER INFORMATION: Primer hpATPaseC-R

<400> SEQUENCE: 46
ctctggatcc gatgggatat ttggcgatgt cc                               32

<210> SEQ ID NO 47
<211> LENGTH: 32
<212> TYPE: DNA
<213> ORGANISM: Artificial
<220> FEATURE:
<223> OTHER INFORMATION: Primer hp-invATPaseC-F

<400> SEQUENCE: 47
```
agagccatgg gatgggatat ttggcgatgt cc    32

<210> SEQ ID NO 48
<211> LENGTH: 39
<212> TYPE: DNA
<213> ORGANISM: Artificial
<220> FEATURE:
<223> OTHER INFORMATION: Primer hp-invATPaseC-R

<400> SEQUENCE: 48
gctgagctca aagaaaatga ctgagtattg gttgatatc    39

<210> SEQ ID NO 49
<211> LENGTH: 729
<212> TYPE: DNA
<213> ORGANISM: Artificial
<220> FEATURE:
<223> OTHER INFORMATION: Caf1-180 hairpin-forming sequence

<400> SEQUENCE: 49
tcggaagctt catatttaaa agatctgtca tcaggaaagg ctataggtaa aagtctaaaa    60
acttggccat atgaagaatc tcttgatgat gaaatcattc ttgttgattt gggagaaact   120
atttgcgaag acaaatctgg ccttcaaaga cacaaagcca agttttttgta cttccatgac   180
aatcgtagac ctgcatatta tggcacatgg aggaaaaaaa gcaaatttgt taaaccaaga   240
aaacctttgg ctgaagataa aaaacatttt gtatgtttct gcttctacct ttgatatata   300
tataataatt atcactaatt agtagtaata tagtatttca agtattttt tcaaaataaa   360
agaatgtagt atatagctat tgcttttctg tagtttataa gtgtgtatat tttaatttat   420
aacttttcta atatatgacc aaaacatggt gatgtgcaga aaatgttttt tatcttcagc   480
caaaggtttt cttggtttaa caaatttgct ttttttcctc catgtgccat aatatgcagg   540
tctacgattg tcatggaagt acaaaaactt ggctttgtgt ctttgaaggc cagatttgtc   600
ttcgcaaata gtttctccca aatcaacaag aatgatttca tcatcaagag attcttcata   660
tggccaagtt tttagacttt tacctatagc cttcctgat gacagatctt ttaaatatga   720
agcttccga   729

<210> SEQ ID NO 50
<211> LENGTH: 889
<212> TYPE: DNA
<213> ORGANISM: Artificial
<220> FEATURE:
<223> OTHER INFORMATION: VatpaseC hairpin-forming sequence

<400> SEQUENCE: 50
aagaagaaat gactgagtat tggttgatat ctgccccagg ggataagacc tgtcaacaga    60
catgggacac gatgaataat atgacaagta acagaataa tttgtcaacc aactacaagt   120
ttcaaatccc ggacttgaaa gttggtactc tggatcagtt agtaggactt tctgatgatc   180
tgggcaagct tgatgggttc gtggagcagg ttaccaggaa ggtagctcag taccttggag   240
aagtacttga agaacagagg gacaagtggt cagaaaacct gcaggccaat aacagcgatt   300
tgccccactta ttttaacccga tttacttggg acatcgccaa atatcccatc gtatgtttct   360
gcttctacct ttgatatata tataataatt atcactaatt agtagtaata tagtatttca   420
agtatttttt tcaaaataaa agaatgtagt atatagctat tgcttttctg tagtttataa   480
gtgtgtatat tttaatttat aacttttcta atatatgacc aaaacatggt gatgtgcagg   540
atgggatatt tggcgatgtc ccaagtaaat cgggttaaat aagtgggcaa atcgctgtta   600

```
ttggcctgca ggttttctga ccacttgtcc ctctgttctt caagtacttc tccaaggtac    660
tgagctacct tcctggtaac ctgctccacg aacccatcaa gcttgcccag atcatcagaa    720
agtcctacta actgatccag agtaccaact ttcaagtccg ggatttgaaa cttgtagttg    780
gttgacaaat tattctgttt acttgtcata ttattcatcg tgtcccatgt ctgttgacag    840
gtcttatccc ctggggcaga tatcaaccaa tactcagtca tttcttctt               889

<210> SEQ ID NO 51
<211> LENGTH: 447
<212> TYPE: DNA
<213> ORGANISM: Diabrotica virgifera

<400> SEQUENCE: 51
gctccaacag tggttcctta tccagatttc aatgccgaag aagatgcaaa ggctctaaaa     60
caagcattca agggtttcgg aacggacgaa gaagctgtaa tagaaattat cacaaaaagg    120
agtaatgaac aaagacgtga aatagcgatt acattcaaaa caatgtatgg caaggatctc    180
atcaaagaac tgaaaagtga acttagagga aatttcgaag atgccatcgt agctctgatg    240
acagagccca tcgagtttca agccaaacag ttgcataaag ctatcagcgg attgggaact    300
gatgaaagta caatmgtmga aattttaagt gtmcacaaca acgatgagat tataagaatt    360
tcccaggcct atgaaggatt gtaccaacgm tcattggaat ctgatatcaa aggagatacc    420
tcaggaacat taaaaagaa ttattag                                         447

<210> SEQ ID NO 52
<211> LENGTH: 424
<212> TYPE: DNA
<213> ORGANISM: Diabrotica virgifera
<220> FEATURE:
<221> NAME/KEY: misc_feature
<222> LOCATION: (393)..(395)
<223> OTHER INFORMATION: n is a, c, g, or t

<400> SEQUENCE: 52
ttgttacaag ctggagaact tctctttgct ggaaccgaag agtcagtatt taatgctgta     60
ttctgtcaaa gaaataaacc acaattgaat ttgatattcg acaaatatga agaaattgtt    120
gggcatccca ttgaaaaagc cattgaaaac gagttttcag gaaatgctaa acaagccatg    180
ttacacctta tccagagcgt aagagatcaa gttgcatatt tggtaaccag gctgcatgat    240
tcaatggcag gcgtcggtac tgacgataga actttaatca gaattgttgt ttcgagatct    300
gaaatcgatc tagaggaaat caaacaatgc tatgaagaaa tctacagtaa aaccttggct    360
gataggatag cggatgacac atctggcgac tannnaaaag ccttattagc cgttgttggt    420
taag                                                                 424

<210> SEQ ID NO 53
<211> LENGTH: 397
<212> TYPE: DNA
<213> ORGANISM: Diabrotica virgifera

<400> SEQUENCE: 53
agatgttggc tgcatctaga gaattacaca agttcttcca tgattgcaag gatgtactga     60
gcagaatagt ggaaaaacag gtatccatgt ctgatgaatt gggaagggac gcaggagctg    120
tcaatgccct tcaacgcaaa caccagaact tcctccaaga cctacaaaca ctccaatcga    180
acgtccaaca aatccaagaa gaatcagcta aacttcaagc tagctatgcc ggtgatagag    240
```

```
ctaaagaaat caccaacagg gagcaggaag tggtagcagc ctgggcagcc ttgcagatcg    300
cttgcgatca gagacacgga aaattgagcg atactggtga tctattcaaa ttctttaact    360
tggtacgaac gttgatgcag tggatggacg aatggac                            397
```

```
<210> SEQ ID NO 54
<211> LENGTH: 490
<212> TYPE: DNA
<213> ORGANISM: Diabrotica virgifera

<400> SEQUENCE: 54
gcagatgaac accagcgaga aaccaagaga tgttagtggt gttgaattgt tgatgaacaa     60
ccatcagaca ctcaaggctg agatcgaagc cagagaagac aactttacgg cttgtatttc    120
tttaggaaag gaattgttga gccgtaatca ctatgctagt gctgatatta aggataaatt    180
ggtcgcgttg acgaatcaaa ggaatgctgt actacagagg tgggaagaaa gatgggagaa    240
cttgcaactc atcctcgagg tataccaatt cgccagagat gcggccgtcg ccgaagcatg    300
gttgatcgca caagaacctt acttgatgag ccaagaacta ggcacacca ttgacgacgt     360 tgaaaacttg ataagaaac acgaagcgtt cgaaaaatcg gcagcggcgc aagaagagag    420
attcagtgct ttggagagac tgacgacgtt cgaattgaga gaaataaaga ggaaacaaga    480
agctgcccag                                                           490
```

```
<210> SEQ ID NO 55
<211> LENGTH: 330
<212> TYPE: DNA
<213> ORGANISM: Diabrotica virgifera

<400> SEQUENCE: 55
agtgaaatgt tagcaaatat aacatccaag tttcgtaatt gtacttgctc agttagaaaa     60
tattctgtag tttcactatc ttcaaccgaa aatagaataa atgtagaacc tcgcgaactt    120
gcctttcctc caaatatca agaacctcga caagtttggt tggagagttt agatacgata    180
gacgacaaaa aattgggtat tcttgagctg catcctgatg ttttgctac taatccaaga    240 atagatatta tacatcaaaa tgttagatgg caaagtttat atagatatgt aagctatgct    300
catacaaagt caagatttga agtgagaggt                                     330
```

```
<210> SEQ ID NO 56
<211> LENGTH: 320
<212> TYPE: DNA
<213> ORGANISM: Diabrotica virgifera

<400> SEQUENCE: 56
caaagtcaag atttgaagtg agaggtggag gtcgaaaacc gtggccgcaa aagggattgg     60
gacgtgctcg acatggttca attagaagtc cactttggag aggtggagga gttgttcatg    120
gaccaaaatc tccaacccct catttttaca tgattccatt ctacaccgt ttgctgggtt    180 tgactagcgc acttcagta aaatttgccc aagatgactt gcacgttgtg gatagtctag    240
atctgccaac tgacgaacaa agttatatag aagagctggt caaaagccgc ttttgggggt    300
ccttcttgtt ttatttgtag                                                320
```

```
<210> SEQ ID NO 57
<211> LENGTH: 503
<212> TYPE: DNA
<213> ORGANISM: Artificial
<220> FEATURE:
<223> OTHER INFORMATION: YFP sequence
```

<400> SEQUENCE: 57

```
caccatgggc tccagcggcg ccctgctgtt ccacggcaag atcccctacg tggtggagat      60
ggagggcaat gtggatggcc acaccttcag catccgcggc aagggctacg gcgatgccag     120
cgtgggcaag gtggatgccc agttcatctg caccaccggc gatgtgcccg tgccctggag     180
caccctggtg accaccctga cctacggcgc ccagtgcttc gccaagtacg ccccgagct      240
gaaggatttc tacaagagct gcatgcccga tggctacgtg caggagcgca ccatcacctt     300
cgagggcgat ggcaatttca gacccgcgc cgaggtgacc ttcgagaatg cagcgtgta      360
caatcgcgtg aagctgaatg ccagggctt caagaaggat ggccacgtgc tgggcaagaa     420
tctggagttc aatttcaccc cccactgcct gtacatctgg ggcgatcagg ccaatcacgg     480
cctgaagagc gccttcaaga tct                                             503
```

<210> SEQ ID NO 58
<211> LENGTH: 46
<212> TYPE: DNA
<213> ORGANISM: Artificial
<220> FEATURE:
<223> OTHER INFORMATION: Primer Ann-F1T7

<400> SEQUENCE: 58

```
ttaatacgac tcactatagg gagagctcca acagtggttc cttatc                     46
```

<210> SEQ ID NO 59
<211> LENGTH: 29
<212> TYPE: DNA
<213> ORGANISM: Artificial
<220> FEATURE:
<223> OTHER INFORMATION: Primer Ann-R1

<400> SEQUENCE: 59

```
ctaataattc tttttttaatg ttcctgagg                                       29
```

<210> SEQ ID NO 60
<211> LENGTH: 22
<212> TYPE: DNA
<213> ORGANISM: Artificial
<220> FEATURE:
<223> OTHER INFORMATION: Primer Ann-F1

<400> SEQUENCE: 60

```
gctccaacag tggttcctta tc                                               22
```

<210> SEQ ID NO 61
<211> LENGTH: 53
<212> TYPE: DNA
<213> ORGANISM: Artificial
<220> FEATURE:
<223> OTHER INFORMATION: Primer Ann-R1T7

<400> SEQUENCE: 61

```
ttaatacgac tcactatagg gagactaata attcttttt aatgttcctg agg              53
```

<210> SEQ ID NO 62
<211> LENGTH: 48
<212> TYPE: DNA
<213> ORGANISM: Artificial
<220> FEATURE:
<223> OTHER INFORMATION: Primer Ann-F2T7

<400> SEQUENCE: 62
ttaatacgac tcactatagg gagattgtta caagctggag aacttctc                48

<210> SEQ ID NO 63
<211> LENGTH: 24
<212> TYPE: DNA
<213> ORGANISM: Artificial
<220> FEATURE:
<223> OTHER INFORMATION: Primer Ann-R2

<400> SEQUENCE: 63
cttaaccaac aacggctaat aagg                                           24

<210> SEQ ID NO 64
<211> LENGTH: 24
<212> TYPE: DNA
<213> ORGANISM: Artificial
<220> FEATURE:
<223> OTHER INFORMATION: Primer Ann-F2

<400> SEQUENCE: 64
ttgttacaag ctggagaact tctc                                           24

<210> SEQ ID NO 65
<211> LENGTH: 48
<212> TYPE: DNA
<213> ORGANISM: Artificial
<220> FEATURE:
<223> OTHER INFORMATION: Primer Ann-R2T7

<400> SEQUENCE: 65
ttaatacgac tcactatagg gagacttaac caacaacggc taataagg                 48

<210> SEQ ID NO 66
<211> LENGTH: 47
<212> TYPE: DNA
<213> ORGANISM: Artificial
<220> FEATURE:
<223> OTHER INFORMATION: Primer Betasp2-F1T7

<400> SEQUENCE: 66
ttaatacgac tcactatagg gagaagatgt tggctgcatc tagagaa                  47

<210> SEQ ID NO 67
<211> LENGTH: 22
<212> TYPE: DNA
<213> ORGANISM: Artificial
<220> FEATURE:
<223> OTHER INFORMATION: Primer Betasp2-R1

<400> SEQUENCE: 67
gtccattcgt ccatccactg ca                                             22

<210> SEQ ID NO 68
<211> LENGTH: 23
<212> TYPE: DNA
<213> ORGANISM: Artificial
<220> FEATURE:
<223> OTHER INFORMATION: Primer Betasp2-F1

<400> SEQUENCE: 68
agatgttggc tgcatctaga gaa                                            23

<210> SEQ ID NO 69
<211> LENGTH: 46
<212> TYPE: DNA
<213> ORGANISM: Artificial

```
<220> FEATURE:
<223> OTHER INFORMATION: Primer Betasp2-R1T7

<400> SEQUENCE: 69
ttaatacgac tcactatagg gagagtccat tcgtccatcc actgca          46

<210> SEQ ID NO 70
<211> LENGTH: 46
<212> TYPE: DNA
<213> ORGANISM: Artificial
<220> FEATURE:
<223> OTHER INFORMATION: Primer Betasp2-F2T7

<400> SEQUENCE: 70
ttaatacgac tcactatagg gagagcagat gaacaccagc gagaaa          46

<210> SEQ ID NO 71
<211> LENGTH: 22
<212> TYPE: DNA
<213> ORGANISM: Artificial
<220> FEATURE:
<223> OTHER INFORMATION: Primer Betasp2-R2

<400> SEQUENCE: 71
ctgggcagct tcttgtttcc tc                                    22

<210> SEQ ID NO 72
<211> LENGTH: 22
<212> TYPE: DNA
<213> ORGANISM: Artificial
<220> FEATURE:
<223> OTHER INFORMATION: Primer Betasp2-F2

<400> SEQUENCE: 72
gcagatgaac accagcgaga aa                                    22

<210> SEQ ID NO 73
<211> LENGTH: 46
<212> TYPE: DNA
<213> ORGANISM: Artificial
<220> FEATURE:
<223> OTHER INFORMATION: Primer Betasp2-R2T7

<400> SEQUENCE: 73
ttaatacgac tcactatagg gagactgggc agcttcttgt ttcctc          46

<210> SEQ ID NO 74
<211> LENGTH: 51
<212> TYPE: DNA
<213> ORGANISM: Artificial
<220> FEATURE:
<223> OTHER INFORMATION: Primer L4-F1T7

<400> SEQUENCE: 74
ttaatacgac tcactatagg gagaagtgaa atgttagcaa atataacatc c     51

<210> SEQ ID NO 75
<211> LENGTH: 26
<212> TYPE: DNA
<213> ORGANISM: Artificial
<220> FEATURE:
<223> OTHER INFORMATION: Primer L4-R1

<400> SEQUENCE: 75
acctctcact tcaaatcttg actttg                                26
```

<210> SEQ ID NO 76
<211> LENGTH: 27
<212> TYPE: DNA
<213> ORGANISM: Artificial
<220> FEATURE:
<223> OTHER INFORMATION: Primer L4-F1

<400> SEQUENCE: 76
agtgaaatgt tagcaaatat aacatcc                                27

<210> SEQ ID NO 77
<211> LENGTH: 50
<212> TYPE: DNA
<213> ORGANISM: Artificial
<220> FEATURE:
<223> OTHER INFORMATION: Primer L4-R1T7

<400> SEQUENCE: 77
ttaatacgac tcactatagg gagaacctct cacttcaaat cttgactttg       50

<210> SEQ ID NO 78
<211> LENGTH: 50
<212> TYPE: DNA
<213> ORGANISM: Artificial
<220> FEATURE:
<223> OTHER INFORMATION: Primer L4-F2T7

<400> SEQUENCE: 78
ttaatacgac tcactatagg gagacaaagt caagatttga agtgagaggt       50

<210> SEQ ID NO 79
<211> LENGTH: 25
<212> TYPE: DNA
<213> ORGANISM: Artificial
<220> FEATURE:
<223> OTHER INFORMATION: Primer L4-R2

<400> SEQUENCE: 79
ctacaaataa aacaagaagg acccc                                  25

<210> SEQ ID NO 80
<211> LENGTH: 26
<212> TYPE: DNA
<213> ORGANISM: Artificial
<220> FEATURE:
<223> OTHER INFORMATION: Primer L4-F2

<400> SEQUENCE: 80
caaagtcaag atttgaagtg agaggt                                 26

<210> SEQ ID NO 81
<211> LENGTH: 49
<212> TYPE: DNA
<213> ORGANISM: Artificial
<220> FEATURE:
<223> OTHER INFORMATION: Primer L4-R2T7

<400> SEQUENCE: 81
ttaatacgac tcactatagg gagactacaa ataaaacaag aaggacccc        49

<210> SEQ ID NO 82
<211> LENGTH: 47
<212> TYPE: DNA
<213> ORGANISM: Artificial
<220> FEATURE:
<223> OTHER INFORMATION: Primer YFP-FT7

<400> SEQUENCE: 82
ttaatacgac tcactatagg gagacaccat gggctccagc ggcgccc         47

<210> SEQ ID NO 83
<211> LENGTH: 23
<212> TYPE: DNA
<213> ORGANISM: Artificial
<220> FEATURE:
<223> OTHER INFORMATION: Primer YFP-R

<400> SEQUENCE: 83
agatcttgaa ggcgctcttc agg                                    23

<210> SEQ ID NO 84
<211> LENGTH: 23
<212> TYPE: DNA
<213> ORGANISM: Artificial
<220> FEATURE:
<223> OTHER INFORMATION: Primer YFP-F

<400> SEQUENCE: 84
caccatgggc tccagcggcg ccc                                    23

<210> SEQ ID NO 85
<211> LENGTH: 47
<212> TYPE: DNA
<213> ORGANISM: Artificial
<220> FEATURE:
<223> OTHER INFORMATION: Primer YFP-RT7

<400> SEQUENCE: 85
ttaatacgac tcactatagg gagaagatct tgaaggcgct cttcagg          47

<210> SEQ ID NO 86
<211> LENGTH: 260
<212> TYPE: DNA
<213> ORGANISM: Diabrotica virgifera

<400> SEQUENCE: 86
ttcggaagct tcatatttaa agatctgtc atcaggaaag gctataggta aaagtctaaa      60
aacttggcca tatgaagaat ctcttgatga tgaaatcatt cttgttgatt gggagaaac    120 tatttgcgaa gacaaatctg gccttcaaag acacaaagcc aagttttgt acttccatga   180 caatcgtaga cctgcatatt atggcacatg gaggaaaaaa agcaaatttg ttaaaccaag   240
aaaacctttg gctgaagata                                              260

<210> SEQ ID NO 87
<211> LENGTH: 551
<212> TYPE: DNA
<213> ORGANISM: Diabrotica virgifera

<400> SEQUENCE: 87
caggtccgat ggctgcaata agaaaaaaat tggtgattgt tggtgacgga gcatgtggaa     60
aaacatgtct tttaatagta tttagtaaag atcagttccc agaagtatac gtgcccactg   120
tattcgaaaa ctatgtggcg gatattgaag tagatgaaa gcaggtagaa ctcgccttat   180
gggataccgc aggtcaagaa gattatgatc gtctgcggcc cctttcatat ccagacaccg   240
atgtgatttt aatgtgcttc tcagtagact cccccgactc attagaaaac atcccagaaa   300
aatggacccc agaggtaaaa cacttttgtc caaatgtgcc aattattctg gtaggcaata    360

```
agaaggatct gcgtaacgat cccaatacca ttaacgaact taaaaagatg aaacaagaac    420
cagtaaaacc tcaagacgga agatccatgg cagagaaaat caatgctttt gcatatctag    480
aatgttctgc caaaagtaag gagggtgtaa gagaggtttt tgaaaatgct acccgagctg    540
cactgcaagt c                                                        551

<210> SEQ ID NO 88
<211> LENGTH: 19
<212> TYPE: DNA
<213> ORGANISM: Diabrotica virgifera

<400> SEQUENCE: 88
gttaatctta tccattaat                                                 19

<210> SEQ ID NO 89
<211> LENGTH: 104
<212> TYPE: DNA
<213> ORGANISM: Diabrotica virgifera

<400> SEQUENCE: 89
tttttgcttg atccttatct gtctgttatc cccgctctta cttcgtaatt tatttaatgt     60
ccgccatttt cgttcgtagt tgaataggcg ttaactttgt gtgt                    104

<210> SEQ ID NO 90
<211> LENGTH: 98
<212> TYPE: DNA
<213> ORGANISM: Diabrotica virgifera

<400> SEQUENCE: 90
gttacgtgtg ttaattaatt tactaagggg gacgttctgt catgatgtat tgacaagggg     60
gcttctgcat gatgtattga ctaacaaaaa taaacccc                             98

<210> SEQ ID NO 91
<211> LENGTH: 745
<212> TYPE: DNA
<213> ORGANISM: Artificial
<220> FEATURE:
<223> OTHER INFORMATION: Caf1-180 hairpin-forming sequence with internal
      cloning sites

<400> SEQUENCE: 91
tcggaagctt catatttaaa agatctgtca tcaggaaagg ctataggtaa aagtctaaaa     60
acttggccat atgaagaatc tcttgatgat gaaatcattc ttgttgattt gggagaaact    120
atttgcgaag acaaatctgg ccttcaaaga cacaaagcca agttttttgta cttccatgac    180 aatcgtagac ctgcatatta tggcacatgg aggaaaaaaa gcaaatttgt taaaccaaga    240
aaacctttgg ctgaagataa aaaacatttt aggcctaggt atgtttctgc ttctaccttt    300
gatatatata taataattat cactaattag tagtaatata gtatttcaag tattttttc    360 aaaataaaag aatgtagtat atagctattg ctttctgta gtttataagt gtgtatattt    420
taatttataa cttttctaat atatgaccaa acatggtga tgtgcaggta ccggtaaaat    480
gttttttatc ttcagccaaa ggttttcttg gttaacaaa tttgcttttt ttcctccatg    540
tgccataata tgcaggtcta cgattgtcat ggaagtacaa aaacttggct ttgtgtcttt    600
gaaggccaga tttgtcttcg caaatagttt ctcccaaatc aacaagaatg atttcatcat    660
caagagattc ttcatatggc caagttttta gactttttacc tatagccttt cctgatgaca    720 gatctttaa atatgaagct tccga                                           745
```

<210> SEQ ID NO 92
<211> LENGTH: 929
<212> TYPE: DNA
<213> ORGANISM: Artificial
<220> FEATURE:
<223> OTHER INFORMATION: version 2 Caf1-180 hairpin RNA-forming sequence with ST-LS1 intron and without maize consensus sequence

<400> SEQUENCE: 92

| | | | | | |
|---|---|---|---|---|---|
| cagaagaaat | gactgagtat | tggttgatat | ctgccccagg | ggataagacc | tgtcaacaga | 60 |
| catgggacac | gatgaataat | atgacaagta | aacagaataa | tttgtcaacc | aactacaagt | 120 |
| ttcaaatccc | ggacttgaaa | gttggtactc | tggatcagtt | agtaggactt | tctgatgatc | 180 |
| tgggcaagct | tgatgggttc | gtggagcagg | ttaccaggaa | ggtagctcag | taccttggag | 240 |
| aagtacttga | agaacagagg | gacaagtggt | cagaaaacct | gcaggccaat | aacagcgatt | 300 |
| tgcccactta | tttaacccga | tttacttggg | acatcgccaa | atatcccatc | ggatccaggc | 360 |
| ctaggtatgt | ttctgcttct | acctttgata | tatatataat | aattatcact | aattagtagt | 420 |
| aatatagtat | ttcaagtatt | tttttcaaaa | taaagaatg | tagtatatag | ctattgcttt | 480 |
| tctgtagttt | ataagtgtgt | atattttaat | ttataacttt | tctaatatat | gaccaaaaca | 540 |
| tggtgatgtg | caggtattta | ataccggtc | catgggatgg | gatatttggc | gatgtcccaa | 600 |
| gtaaatcggg | ttaaataagt | gggcaaatcg | ctgttattgg | cctgcaggtt | ttctgaccac | 660 |
| ttgtccctct | gttcttcaag | tacttctcca | aggtactgag | ctaccttcct | ggtaacctgc | 720 |
| tccacgaacc | catcaagctt | gcccagatca | tcagaaagtc | ctactaactg | atccagagta | 780 |
| ccaactttca | agtccgggat | ttgaaacttg | tagttggttg | acaaattatt | ctgtttactt | 840 |
| gtcatattat | tcatcgtgtc | ccatgtctgt | tgacaggtct | tatcccctgg | ggcagatatc | 900 |
| aaccaatact | cagtcatttc | ttctgagct | | | | 929 |

<210> SEQ ID NO 93
<211> LENGTH: 905
<212> TYPE: DNA
<213> ORGANISM: Artificial
<220> FEATURE:
<223> OTHER INFORMATION: VatpaseC hairpin-forming sequence with internal cloning sites and maize consensus sequence

<400> SEQUENCE: 93

| | | | | | |
|---|---|---|---|---|---|
| aagaagaaat | gactgagtat | tggttgatat | ctgccccagg | ggataagacc | tgtcaacaga | 60 |
| catgggacac | gatgaataat | atgacaagta | aacagaataa | tttgtcaacc | aactacaagt | 120 |
| ttcaaatccc | ggacttgaaa | gttggtactc | tggatcagtt | agtaggactt | tctgatgatc | 180 |
| tgggcaagct | tgatgggttc | gtggagcagg | ttaccaggaa | ggtagctcag | taccttggag | 240 |
| aagtacttga | agaacagagg | gacaagtggt | cagaaaacct | gcaggccaat | aacagcgatt | 300 |
| tgcccactta | tttaacccga | tttacttggg | acatcgccaa | atatcccatc | aggcctaggt | 360 |
| atgtttctgc | ttctaccttt | gatatatata | taataattat | cactaattag | tagtaatata | 420 |
| gtatttcaag | tattttttc | aaaataaaag | aatgtagtat | atagctattg | cttttctgta | 480 |
| gtttataagt | gtgtatattt | taatttataa | cttttctaat | atatgaccaa | aacatggtga | 540 |
| tgtgcaggta | ccggtgatgg | gatatttggc | gatgtcccaa | gtaaatcggg | ttaaataagt | 600 |
| gggcaaatcg | ctgttattgg | cctgcaggtt | ttctgaccac | ttgtccctct | gttcttcaag | 660 |
| tacttctcca | aggtactgag | ctaccttcct | ggtaacctgc | tccacgaacc | catcaagctt | 720 |
| gcccagatca | tcagaaagtc | ctactaactg | atccagagta | ccaactttca | agtccgggat | 780 |

```
ttgaaacttg tagttggttg acaaattatt ctgtttactt gtcatattat tcatcgtgtc    840
ccatgtctgt tgacaggtct tatcccctgg ggcagatatc aaccaatact cagtcatttc    900
ttctt                                                                905
```

<210> SEQ ID NO 94
<211> LENGTH: 929
<212> TYPE: DNA
<213> ORGANISM: Artificial
<220> FEATURE:
<223> OTHER INFORMATION: version 2 VatpaseC hairpin RNA-forming sequence
      with ST-LS1 intron and without maize consensus sequence

<400> SEQUENCE: 94

```
cagaagaaat gactgagtat tggttgatat ctgccccagg ggataagacc tgtcaacaga     60
catgggacac gatgaataat atgacaagta aacagaataa tttgtcaacc aactacaagt    120
ttcaaatccc ggacttgaaa gttggtactc tggatcagtt agtaggactt tctgatgatc    180
tgggcaagct tgatgggttc gtggagcagg ttaccaggag ggtagctcag taccttggag    240
aagtacttga agaacagagg gacaagtggt cagaaaacct gcaggccaat aacagcgatt    300
tgcccactta ttttaacccga tttacttggg acatcgccaa atatcccatc ggatccaggc    360
ctaggtatgt ttctgcttct acctttgata tatataat aattatcact aattagtagt       420
aatatagtat ttcaagtatt tttttcaaaa taaagaatg tagtatatag ctattgcttt    480
tctgtagttt ataagtgtgt atattttaat ttataacttt tctaatatat gaccaaaaca    540
tggtgatgtg caggtattta ataccggtc catgggatgg gatatttggc gatgtcccaa    600
gtaaatcggg ttaaataagt gggcaaatcg ctgttattgg cctgcaggtt ttctgaccac    660
ttgtccctct gttcttcaag tacttctcca aggtactgag ctaccttcct ggtaacctgc    720
tccacgaacc catcaagctt gcccagatca tcagaaagtc ctactaactg atccagagta    780
ccaactttca gtccgggat ttgaaacttg tagttggttg acaaattatt ctgtttactt      840
gtcatattat tcatcgtgtc ccatgtctgt tgacaggtct tatcccctgg ggcagatatc    900
aaccaatact cagtcatttc ttctgagct                                      929
```

<210> SEQ ID NO 95
<211> LENGTH: 501
<212> TYPE: DNA
<213> ORGANISM: Artificial
<220> FEATURE:
<223> OTHER INFORMATION: Segment of a Caf1-180 sense strand containing
      an ST-LS1 intron

<400> SEQUENCE: 95

```
ggtacctaat cggaagcttc atatttaaaa gatctgtcat caggaaaggc tataggtaaa     60
agtctaaaaa cttggccata tgaagaatct cttgatgatg aaatcattct tgttgatttg    120
ggagaaacta tttgcgaaga caatctggcc ttcaaagac acaaagccaa gttttttgtac    180 ttccatgaca atcgtagacc tgcatattat ggcacatgga ggaaaaaaag caaatttgtt    240
aaaccaagaa aacctttggc tgaagataaa aacatttttg actagtaccg gttgggaaag    300
gtatgtttct gcttctacct tgatatata taataatt atcactaatt agtagtaata       360
tagtatttca gtattttttt tcaaaataaa agaatgtagt atatagctat gcttttctg    420 tagtttataa gtgtgtatat tttaatttat aacttttcta atatatgacc aaaacatggt    480
gatgtgcagg ttgatccgcg g                                              501
```

<210> SEQ ID NO 96
<211> LENGTH: 286
<212> TYPE: DNA
<213> ORGANISM: Artificial
<220> FEATURE:
<223> OTHER INFORMATION: Segment of a Caf1-180 DNA antisense strand

<400> SEQUENCE: 96

| | |
|---|---|
| ccgcggttaa aaatgttttt tatcttcagc caaaggtttt cttggtttaa caaatttgct | 60 |
| ttttttcctc catgtgccat aatatgcagg tctacgattg tcatggaagt acaaaaactt | 120 |
| ggctttgtgt ctttgaaggc cagatttgtc ttcgcaaata gtttctccca atcaacaag | 180 |
| aatgatttca tcatcaagag attcttcata tggccaagtt tttagacttt tacctatagc | 240 |
| ctttcctgat gacagatctt ttaaatatga agcttccgaa gagctc | 286 |

<210> SEQ ID NO 97
<211> LENGTH: 781
<212> TYPE: DNA
<213> ORGANISM: Artificial
<220> FEATURE:
<223> OTHER INFORMATION: Caf1-180 hairpin RNA-forming DNA sequence
    containing an ST-LS1 intron

<400> SEQUENCE: 97

| | |
|---|---|
| ggtacctaat cggaagcttc atatttaaaa gatctgtcat caggaaaggc tataggtaaa | 60 |
| agtctaaaaa cttggccata tgaagaatct cttgatgatg aaatcattct tgttgatttg | 120 |
| ggagaaacta tttgcgaaga caaatctggc cttcaaagac acaaagccaa gtttttgtac | 180 |
| ttccatgaca atcgtagacc tgcatattat ggcacatgga ggaaaaaaag caaatttgtt | 240 |
| aaaccaagaa aacctttggc tgaagataaa aacatttttg actagtaccg gttgggaaag | 300 |
| gtatgttttct gcttctacct tgatatata tataataatt atcactaatt agtagtaata | 360 |
| tagtatttca agtattttt tcaaaataaa agaatgtagt atatagctat tgcttttctg | 420 |
| tagtttataa gtgtgtatat tttaatttat aacttttcta atatatgacc aaaacatggt | 480 |
| gatgtgcagg ttgatccgcg gttaaaaatg ttttttatct tcagccaaag gttttcttgg | 540 |
| tttaacaaat ttgctttttt tcctccatgt gccataatat gcaggtctac gattgtcatg | 600 |
| gaagtacaaa aacttggctt gtgtctttg aaggccagat ttgtcttcgc aaatagtttc | 660 |
| tcccaaatca acaagaatga tttcatcatc aagagattct tcatatggcc aagttttag | 720 |
| acttttacct atagcctttc tgatgacag atcttttaaa tatgaagctt ccgaagagct | 780 |
| c | 781 |

<210> SEQ ID NO 98
<211> LENGTH: 511
<212> TYPE: DNA
<213> ORGANISM: Artificial
<220> FEATURE:
<223> OTHER INFORMATION: Segment of a VatpaseC DNA sense strand
    containing an ST-LS1 intron

<400> SEQUENCE: 98

| | |
|---|---|
| ggtacctaaa ctgagtattg gttgatatct gccccagggg ataagacctg tcaacagaca | 60 |
| tgggacacga tgaataatat gacaagtaaa cagaataatt tgtcaaccaa ctacaagttt | 120 |
| caaatcccgg acttgaaagt tggtactctg gatcagttag taggactttc tgatgatctg | 180 |
| ggcaagcttg atgggttcgt ggagcaggtt accaggaagg tagctcagta ccttggagaa | 240 |
| gtacttgaag aacagaggga caagtggtca gaaaacctgc aggccaatag actagtaccg | 300 |

```
gttgggaaag gtatgtttct gcttctacct ttgatatata tataataatt atcactaatt    360
agtagtaata tagtatttca agtatttttt tcaaaataaa agaatgtagt atatagctat    420
tgcttttctg tagtttataa gtgtgtatat tttaatttat aacttttcta atatatgacc    480
aaaacatggt gatgtgcagg ttgatccgcg g                                   511
```

<210> SEQ ID NO 99
<211> LENGTH: 296
<212> TYPE: DNA
<213> ORGANISM: Artificial
<220> FEATURE:
<223> OTHER INFORMATION: Segment of a VatpaseC DNA antisense strand

<400> SEQUENCE: 99

```
ccgcggttat attggcctgc aggttttctg accacttgtc cctctgttct tcaagtactt     60
ctccaaggta ctgagctacc ttcctggtaa cctgctccac gaacccatca agcttgccca    120
gatcatcaga aagtcctact aactgatcca gagtaccaac tttcaagtcc gggatttgaa    180
acttgtagtt ggttgacaaa ttattctgtt tacttgtcat attattcatc gtgtcccatg    240
tctgttgaca ggtcttatcc cctggggcag atatcaacca atactcagta gagctc       296
```

<210> SEQ ID NO 100
<211> LENGTH: 801
<212> TYPE: DNA
<213> ORGANISM: Artificial
<220> FEATURE:
<223> OTHER INFORMATION: VatpaseC hairpin RNA-forming DNA sequence
      containing an ST-LS1 intron

<400> SEQUENCE: 100

```
ggtacctaaa ctgagtattg gttgatatct gccccagggg ataagacctg tcaacagaca     60
tgggacacga tgaataatat gacaagtaaa cagaataatt tgtcaaccaa ctacaagttt    120
caaatcccgg acttgaaagt tggtactctg gatcagttag taggactttc tgatgatctg    180
ggcaagcttg atgggttcgt ggagcaggtt accaggaagg tagctcagta ccttggagaa    240
gtacttgaag aacagaggga caagtggtca gaaaacctgc aggccaatag actagtaccg    300
gttgggaaag gtatgtttct gcttctacct ttgatatata tataataatt atcactaatt    360
agtagtaata tagtatttca agtatttttt tcaaaataaa agaatgtagt atatagctat    420
tgcttttctg tagtttataa gtgtgtatat tttaatttat aacttttcta atatatgacc    480
aaaacatggt gatgtgcagg ttgatccgcg gttatattgg cctgcaggtt ttctgaccac    540
ttgtccctct gttcttcaag tacttctcca aggtactgag ctaccttcct ggtaacctgc    600
tccacgaacc catcaagctt gcccagatca tcagaaagtc ctactaactg atccagagta    660
ccaactttca gtccgggat tgaaacttg tagttggttg acaaattatt ctgtttactt    720
gtcatattat tcatcgtgtc ccatgtctgt tgacaggtct tatcccctgg ggcagatatc    780
aaccaatact cagtagagct c                                              801
```

<210> SEQ ID NO 101
<211> LENGTH: 402
<212> TYPE: DNA
<213> ORGANISM: Artificial
<220> FEATURE:
<223> OTHER INFORMATION: Segment of a VatpaseC DNA sense strand
      containing an ST-LS1 intron

<400> SEQUENCE: 101

```
ggtacctaaa ctgagtattg gttgatatct gccccagggg ataagacctg tcaacagaca      60
tgggacacga tgaataatat gacaagtaaa cagaataatt tgtcaaccaa ctacaagttt     120
caaatcccgg acttgaaagt tggtactctg gatcagttag taggactttc tgatgatctg     180
gactagtacc ggttgggaaa ggtatgtttc tgcttctacc tttgatatat atataataat     240
tatcactaat tagtagtaat atagtatttc aagtattttt ttcaaaataa agaatgtag      300 tatatagcta ttgcttttct gtagtttata agtgtgtata ttttaattta taacttttct     360
aatatatgac caaaacatgg tgatgtgcag gttgatccgc gg                        402

<210> SEQ ID NO 102
<211> LENGTH: 187
<212> TYPE: DNA
<213> ORGANISM: Artificial
<220> FEATURE:
<223> OTHER INFORMATION: Segment of a VatpaseC DNA antisense strand

<400> SEQUENCE: 102
ccgcggttac agatcatcag aaagtcctac taactgatcc agagtaccaa ctttcaagtc      60
cgggatttga aacttgtagt tggttgacaa attattctgt ttacttgtca tattattcat     120
cgtgtcccat gtctgttgac aggtcttatc ccctggggca gatatcaacc aatactcagt     180
agagctc                                                               187

<210> SEQ ID NO 103
<211> LENGTH: 583
<212> TYPE: DNA
<213> ORGANISM: Artificial
<220> FEATURE:
<223> OTHER INFORMATION: VatpaseC hairpin RNA-forming DNA sequence
      containing an ST-LS1 intron

<400> SEQUENCE: 103
ggtacctaaa ctgagtattg gttgatatct gccccagggg ataagacctg tcaacagaca      60
tgggacacga tgaataatat gacaagtaaa cagaataatt tgtcaaccaa ctacaagttt     120
caaatcccgg acttgaaagt tggtactctg gatcagttag taggactttc tgatgatctg     180
gactagtacc ggttgggaaa ggtatgtttc tgcttctacc tttgatatat atataataat     240
tatcactaat tagtagtaat atagtatttc aagtattttt ttcaaaataa agaatgtag      300 tatatagcta ttgcttttct gtagtttata agtgtgtata ttttaattta taacttttct     360
aatatatgac caaaacatgg tgatgtgcag gttgatccgc ggttacagat catcagaaag     420
tcctactaac tgatccagag taccaacttt caagtccggg atttgaaact tgtagttggt     480
tgacaaatta ttctgtttac ttgtcatatt attcatcgtg tcccatgtct gttgacaggt     540
cttatcccct ggggcagata tcaaccaata ctcagtagag ctc                       583

<210> SEQ ID NO 104
<211> LENGTH: 531
<212> TYPE: DNA
<213> ORGANISM: Artificial
<220> FEATURE:
<223> OTHER INFORMATION: Segment of a VatpaseH DNA sense strand
      containing an ST-LS1 intron

<400> SEQUENCE: 104
ggtacctaag tattgcagca aagagctaca gatataagaa atcaacatgt aaactggcaa      60
tcctatttcc agtcacaaat gatttcgcag gaagactaca acttcatagt agcttttgat     120
gtgactgata gtgcaaaaag agaagctctc ctgaaaagcg acagaaacca atgtgctcaa     180
```

```
acattgttga accttttggg gcatgtatcc aaggaccaaa ctctgcagta cattttagtt    240
ttggttgatg atatgttaca ggagaacaga agtcgtgtag agatatttca cgaatatgcc    300
aaccaaaagg actagtaccg gttgggaaag gtatgtttct gcttctacct ttgatatata    360
tataataatt atcactaatt agtagtaata tagtatttca agtattttt tcaaaataaa    420 agaatgtagt atatagctat tgcttttctg tagtttataa gtgtgtatat tttaatttat    480
aacttttcta atatatgacc aaaacatggt gatgtgcagg ttgatccgcg g             531

<210> SEQ ID NO 105
<211> LENGTH: 316
<212> TYPE: DNA
<213> ORGANISM: Artificial
<220> FEATURE:
<223> OTHER INFORMATION: Segment of a VatpaseH DNA antisense strand

<400> SEQUENCE: 105
ccgcggttac ttttggttgg catattcgtg aaatatctct acacgacttc tgttctcctg     60
taacatatca tcaaccaaaa ctaaaatgta ctgcagagtt tggtccttgg atacatgccc    120
caaaaggttc aacaatgttt gagcacattg gtttctgtcg cttttcagga gagcttctct    180
ttttgcacta tcagtcacat caaaagctac tatgaagttg tagtcttcct gcgaaatcat    240
ttgtgactgg aaataggatt gccagtttac atgttgattt cttatatctg tagctctttg    300
ctgcaataca gagctc                                                    316

<210> SEQ ID NO 106
<211> LENGTH: 841
<212> TYPE: DNA
<213> ORGANISM: Artificial
<220> FEATURE:
<223> OTHER INFORMATION: VatpaseH hairpin RNA-forming DNA sequence
      containing an ST-LS1 intron

<400> SEQUENCE: 106
ggtacctaag tattgcagca aagagctaca gatataagaa atcaacatgt aaactggcaa     60
tcctatttcc agtcacaaat gatttcgcag gaagactaca acttcatagt agcttttgat    120
gtgactgata gtgcaaaaag agaagctctc ctgaaaagcg acagaaacca atgtgctcaa    180
acattgttga accttttggg gcatgtatcc aaggaccaaa ctctgcagta cattttagtt    240
ttggttgatg atatgttaca ggagaacaga agtcgtgtag agatatttca cgaatatgcc    300
aaccaaaagg actagtaccg gttgggaaag gtatgtttct gcttctacct ttgatatata    360
tataataatt atcactaatt agtagtaata tagtatttca agtattttt tcaaaataaa    420 agaatgtagt atatagctat tgcttttctg tagtttataa gtgtgtatat tttaatttat    480
aacttttcta atatatgacc aaaacatggt gatgtgcagg ttgatccgcg gttacttttg    540
gttggcatat tcgtgaaata tctctacacg acttctgttc tcctgtaaca tatcatcaac    600
caaaactaaa atgtactgca gagtttggtc cttggataca tgcccaaaaa ggttcaacaa    660
tgtttgagca cattggtttc tgtcgctttt caggagagct tctcttttg cactatcagt    720 cacatcaaaa gctactatga agttgtagtc ttcctgcgaa atcatttgtg actggaaata    780
ggattgccag tttacatgtt gatttcttat atctgtagct ctttgctgca atacagagct    840
c                                                                    841

<210> SEQ ID NO 107
<211> LENGTH: 531
```

<212> TYPE: DNA
<213> ORGANISM: Artificial
<220> FEATURE:
<223> OTHER INFORMATION: Segment of a Rho1 DNA sense strand containing an ST-LS1 intron

<400> SEQUENCE: 107

| | | | | | |
|---|---|---|---|---|---|
| ggtacctaac | atgaggaaaa | acatgtcttt | taatagtatt | tagtaaagat | cagttcccag | 60 |
| aagtatacgt | gcccactgta | ttcgaaaact | atgtggcgga | tattgaagta | gatggaaagc | 120 |
| aggtagaact | cgccttatgg | gataccgcag | gtcaagaaga | ttatgatcgt | ctgcggcccc | 180 |
| tttcatatcc | agacaccgat | gtgattttaa | tgtgcttctc | agtagactcc | cccgactcat | 240 |
| tagaaaacat | cccagaaaaa | tggaccccag | aggtaaaaca | cttttgtcca | aatgtgccaa | 300 |
| ttattctggg | actagtaccg | gttgggaaag | gtatgtttct | gcttctacct | ttgatatata | 360 |
| tataataatt | atcactaatt | agtagtaata | tagtatttca | agtattttttt | tcaaaataaa | 420 |
| agaatgtagt | atatagctat | tgcttttctg | tagtttataa | gtgtgtatat | tttaatttat | 480 |
| aacttttcta | atatatgacc | aaaacatggt | gatgtgcagg | ttgatccgcg | g | 531 |

<210> SEQ ID NO 108
<211> LENGTH: 316
<212> TYPE: DNA
<213> ORGANISM: Artificial
<220> FEATURE:
<223> OTHER INFORMATION: Segment of a Rho1 DNA antisense strand

<400> SEQUENCE: 108

| | | | | | |
|---|---|---|---|---|---|
| ccgcggttac | cagaataatt | ggcacatttg | gacaaaagtg | ttttacctct | ggggtccatt | 60 |
| tttctgggat | gttttctaat | gagtcggggg | agtctactga | gaagcacatt | aaaatcacat | 120 |
| cggtgtctgg | atatgaaagg | ggccgcagac | gatcataatc | ttcttgacct | gcggtatccc | 180 |
| ataaggcgag | ttctacctgc | tttccatcta | cttcaatatc | cgccacatag | ttttcgaata | 240 |
| cagtgggcac | gtatacttct | gggaactgat | ctttactaaa | tactattaaa | agacatgttt | 300 |
| ttcctcatga | gagctc | | | | | 316 |

<210> SEQ ID NO 109
<211> LENGTH: 841
<212> TYPE: DNA
<213> ORGANISM: Artificial
<220> FEATURE:
<223> OTHER INFORMATION: Rho1 hairpin RNA-forming DNA sequence containing an ST-LS1 intron

<400> SEQUENCE: 109

| | | | | | |
|---|---|---|---|---|---|
| ggtacctaac | atgaggaaaa | acatgtcttt | taatagtatt | tagtaaagat | cagttcccag | 60 |
| aagtatacgt | gcccactgta | ttcgaaaact | atgtggcgga | tattgaagta | gatggaaagc | 120 |
| aggtagaact | cgccttatgg | gataccgcag | gtcaagaaga | ttatgatcgt | ctgcggcccc | 180 |
| tttcatatcc | agacaccgat | gtgattttaa | tgtgcttctc | agtagactcc | cccgactcat | 240 |
| tagaaaacat | cccagaaaaa | tggaccccag | aggtaaaaca | cttttgtcca | aatgtgccaa | 300 |
| ttattctggg | actagtaccg | gttgggaaag | gtatgtttct | gcttctacct | ttgatatata | 360 |
| tataataatt | atcactaatt | agtagtaata | tagtatttca | agtatttttt | tcaaaataaa | 420 |
| agaatgtagt | atatagctat | tgcttttctg | tagtttataa | gtgtgtatat | tttaatttat | 480 |
| aacttttcta | atatatgacc | aaaacatggt | gatgtgcagg | ttgatccgcg | gttaccagaa | 540 |
| taattggcac | atttggacaa | aagtgtttta | cctctggggt | ccattttttct | gggatgtttt | 600 |

```
ctaatgagtc gggggagtct actgagaagc acattaaaat cacatcggtg tctggatatg    660 aaagggccg cagacgatca taatcttctt gacctgcggt atcccataag gcgagttcta     720
cctgctttcc atctacttca atatccgcca catagttttc gaatacagtg ggcacgtata    780
cttctgggaa ctgatcttta ctaaatacta ttaaaagaca tgttttttcct catgagagct   840 c                                                                    841

<210> SEQ ID NO 110
<211> LENGTH: 260
<212> TYPE: DNA
<213> ORGANISM: Artificial
<220> FEATURE:
<223> OTHER INFORMATION: Segment of a Caf-180 DNA used to provide a
      template for dsRNA synthesis

<400> SEQUENCE: 110
ttcggaagct tcatatttaa aagatctgtc atcaggaaag gctataggta aaagtctaaa     60
aacttggcca tatgaagaat ctcttgatga tgaaatcatt cttgttgatt gggagaaac    120 tatttgcgaa gacaaatctg gccttcaaag acacaaagcc aagttttttgt acttccatga  180 caatcgtaga cctgcatatt atggcacatg gaggaaaaaa agcaaatttg ttaaaccaag   240
aaaacctttg gctgaagata                                               260

<210> SEQ ID NO 111
<211> LENGTH: 460
<212> TYPE: DNA
<213> ORGANISM: Artificial
<220> FEATURE:
<223> OTHER INFORMATION: Segment of a VatpaseC region 1 DNA used to
      provide a template for dsRNA synthesis

<400> SEQUENCE: 111
agaagaaatg actgagtatt ggttgatatc tgccccaggg gataagacct gtcaacagac     60
atgggacacg atgaataata tgacaagtaa acagaatat ttgtcaacca actacaagtt   120
tcaaatcccg gacttgaaag ttggtactct ggatcagtta gtaggacttt ctgatgatct   180
gggcaagctt gatgggttcg tggagcaggt taccaggaag gtagctcagt accttggaga   240
agtacttgaa gaacagaggg acaagtggtc agaaaacctg caggccaata acagcgattt   300
gcccacttat ttaacccgat ttacttggga catcgccaaa tatcccatca agcaatcgct   360
ccgtaacatc gccgatataa tcagcaaaca agttggccaa attgacgctg atctgaagac   420
caaatcgtct gcgtacaata acttgaaagg aagtcttcag                          460

<210> SEQ ID NO 112
<211> LENGTH: 349
<212> TYPE: DNA
<213> ORGANISM: Artificial
<220> FEATURE:
<223> OTHER INFORMATION: Segment of a VatpaseC region 1 (short) DNA used
      to provide a template for dsRNA synthesis

<400> SEQUENCE: 112
agaagaaatg actgagtatt ggttgatatc tgccccaggg gataagacct gtcaacagac     60
atgggacacg atgaataata tgacaagtaa acagaatat ttgtcaacca actacaagtt   120
tcaaatcccg gacttgaaag ttggtactct ggatcagtta gtaggacttt ctgatgatct   180
gggcaagctt gatgggttcg tggagcaggt taccaggaag gtagctcagt accttggaga   240
agtacttgaa gaacagaggg acaagtggtc agaaaacctg caggccaata acagcgattt   300
```

```
gcccacttat ttaacccgat ttacttggga catcgccaaa tatcccatc         349
```

```
<210> SEQ ID NO 113
<211> LENGTH: 500
<212> TYPE: DNA
<213> ORGANISM: Artificial
<220> FEATURE:
<223> OTHER INFORMATION: Segment of a VatpaseC region 2 DNA used to
      provide a template for dsRNA synthesis

<400> SEQUENCE: 113
agaaacagac aggaagttta ctaacaagaa acttggcaga tttggtgaaa aaggaacatt    60
ttattttgga ttctgaatat ttgcagacat tgttggttat tgttccaaaa gcccaattca   120
acgaatggaa tgcgacatac gaaaagatta ccgacatgat agtccctcgt tcttcacaac   180
tgattaaaca ggataacgaa tacggtctat atactgtatc cctattcaaa aaggtcgtcg   240
aagaattcaa gttacacgct agagaaaaga agttcatcgt tcgtgatttc atatataacg   300
aagaggaact ggcagctgga aagaacgaga taaccaaact cgtcaccgat aaaaagaagc   360
aatttggtcc attagttaga tggcttaaag tcaacttcag cgagtgtttc tgcgcctgga   420
ttcacgttaa agcgttgagg gtatttgttg aatctgtttt aagatatggc ctcccgtcaa   480
tttccaagct attttaatcc                                              500
```

```
<210> SEQ ID NO 114
<211> LENGTH: 445
<212> TYPE: DNA
<213> ORGANISM: Artificial
<220> FEATURE:
<223> OTHER INFORMATION: Segment of a VatpaseH region 1 DNA used to
      provide a template for dsRNA synthesis

<400> SEQUENCE: 114
tcatgattgt tccagatatg ttggctgcta caagtgtatt gcagcaaaga gctacagata    60
taagaaatca acatgtaaac tggcaatcct atttccagtc acaaatgatt tcgcaggaag   120
actacaactt catagtagct tttgatgtga ctgatagtgc aaaaagagaa gctctcctga   180
aaagcgacag aaaccaatgt gctcaaacat tgttgaacct ttggggcat gtatccaagg    240 accaaactct gcagtacatt ttagttttgg ttgatgatat gttacaggag aacagaagtc   300
gtgtagagat atttcacgaa tatgccaacc aaaagaaaga atctgtttgg ggtccatttt   360
tgaaccttct taaccgccag gatggattta ttaccaacat gacttctagg atcatcgcta   420
aaattgcttg ttggtcgcag acact                                        445
```

```
<210> SEQ ID NO 115
<211> LENGTH: 570
<212> TYPE: DNA
<213> ORGANISM: Artificial
<220> FEATURE:
<223> OTHER INFORMATION: Segment of a VatpaseH region 2 DNA used to
      provide a template for dsRNA synthesis

<400> SEQUENCE: 115
agaacattgt atagctatgg tgcaatgcaa agtattgaaa caattggcca ttttagaaca    60
gcgcaagttc gatgatgaag atgtgacagc tgatgtcgaa tttctaactg aaaaactaca   120
gagttctgtt caggatctga gttccttcga tgaatattca actgaagtca atctggacg    180 tttggaatgg tctccagtac acaagagcaa gttctggcgg aaaatgcgc agcgcctcaa    240 cgagaaaaac tacgaattac tccgtattct cattcatttg ttagaaacca gcaaggaccc   300
```

```
cttggtattg agcgtagcta gtttcgatat tggagagtat gttcgccatt atcctcgcgg      360
caaacacata atcgagcagt tgggaggaaa gcaattagtt atgcaactct tagcccacga      420
agatcccaat gtacgatatg aagctctgtt ggcagtccaa aaattgatgg tccacaattg      480 ggatacctt ggtcgtcaac ttgaaaaaga gcaaagtaca gataaaaacg cgccaaaggg       540
tggagctcct gtcgcaggca aggcgtaaat                                       570
```

<210> SEQ ID NO 116
<211> LENGTH: 551
<212> TYPE: DNA
<213> ORGANISM: Artificial
<220> FEATURE:
<223> OTHER INFORMATION: Segment of a Rho1 DNA used to provide a
      template for dsRNA synthesis

<400> SEQUENCE: 116

```
caggtccgat ggctgcaata agaaaaaaat tggtgattgt tggtgacgga gcatgtggaa       60
aaacatgtct tttaatagta tttagtaaag atcagttccc agaagtatac gtgcccactg      120
tattcgaaaa ctatgtggcg gatattgaag tagatggaaa gcaggtagaa ctcgcccttat     180 gggataccgc aggtcaagaa gattatgatc gtctgcggcc cctttcatat ccagacaccg      240
atgtgatttt aatgtgcttc tcagtagact ccccgactc attagaaaac atcccagaaa       300
aatggacccc agaggtaaaa cactttgtc caaatgtgcc aattattctg gtaggcaata      360
agaaggatct gcgtaacgat cccaatacca ttaacgaact taaaagatg aaacaagaac       420 cagtaaaacc tcaagacgga agatccatgg cagagaaaat caatgctttt gcatatctag      480
aatgttctgc caaagtaag gagggtgtaa gagaggtttt tgaaaatgct acccgagctg       540
cactgcaagt c                                                           551
```

<210> SEQ ID NO 117
<211> LENGTH: 15
<212> TYPE: RNA
<213> ORGANISM: Artificial
<220> FEATURE:
<223> OTHER INFORMATION: VatpaseC RNA sense strand ("VatpaseC5'-15")
      used as a dsRNA

<400> SEQUENCE: 117

```
augacugagu auugg                                                        15
```

<210> SEQ ID NO 118
<211> LENGTH: 25
<212> TYPE: RNA
<213> ORGANISM: Artificial
<220> FEATURE:
<223> OTHER INFORMATION: VatpaseC RNA sense strand ("VatpaseC5'-25")
      used as a dsRNA

<400> SEQUENCE: 118

```
augacugagu auugguugau aucug                                             25
```

<210> SEQ ID NO 119
<211> LENGTH: 15
<212> TYPE: RNA
<213> ORGANISM: Artificial
<220> FEATURE:
<223> OTHER INFORMATION: VatpaseC RNA sense strand ("VatpaseC3'-15")
      used as a dsRNA

<400> SEQUENCE: 119

```
cuuucugaug aucug                                                        15
```

<210> SEQ ID NO 120
<211> LENGTH: 25
<212> TYPE: RNA
<213> ORGANISM: Artificial
<220> FEATURE:
<223> OTHER INFORMATION: VatpaseC RNA sense strand ("VatpaseC3'-25")
      used as a dsRNA

<400> SEQUENCE: 120
guuaguagga cuuucugaug aucug                                              25

<210> SEQ ID NO 121
<211> LENGTH: 50
<212> TYPE: DNA
<213> ORGANISM: Artificial
<220> FEATURE:
<223> OTHER INFORMATION: Primer VatpaseC-FT7

<400> SEQUENCE: 121
ttaatacgac tcactatagg gagaatgact gagtattggt tgatatctgc                   50

<210> SEQ ID NO 122
<211> LENGTH: 45
<212> TYPE: DNA
<213> ORGANISM: Artificial
<220> FEATURE:
<223> OTHER INFORMATION: Primer VatpaseC-R50T7

<400> SEQUENCE: 122
ttaatacgac tcactatagg gagatgttga caggtcttat ccccct                       45

<210> SEQ ID NO 123
<211> LENGTH: 54
<212> TYPE: DNA
<213> ORGANISM: Artificial
<220> FEATURE:
<223> OTHER INFORMATION: Primer VatpaseC-R100T7

<400> SEQUENCE: 123
ttaatacgac tcactatagg gagattgaca aattattctg tttacttgtc atat              54

<210> SEQ ID NO 124
<211> LENGTH: 51
<212> TYPE: DNA
<213> ORGANISM: Artificial
<220> FEATURE:
<223> OTHER INFORMATION: Primer VatpaseC-RT7

<400> SEQUENCE: 124
ttaatacgac tcactatagg gagacagatc atcagaaagt cctactaact g                 51

<210> SEQ ID NO 125
<211> LENGTH: 48
<212> TYPE: DNA
<213> ORGANISM: Artificial
<220> FEATURE:
<223> OTHER INFORMATION: Primer VatpaseC-F50T7

<400> SEQUENCE: 125
ttaatacgac tcactatagg gagagacttg aaagttggta ctctggat                     48

<210> SEQ ID NO 126
<211> LENGTH: 52
<212> TYPE: DNA
<213> ORGANISM: Artificial

```
<220> FEATURE:
<223> OTHER INFORMATION: Primer VatpaseC-F100T7

<400> SEQUENCE: 126
ttaatacgac tcactatagg gagagacaag taaacagaat aatttgtcaa cc        52

<210> SEQ ID NO 127
<211> LENGTH: 62
<212> TYPE: DNA
<213> ORGANISM: Artificial
<220> FEATURE:
<223> OTHER INFORMATION: VatpaseC sense strand ("VatpaseC5'-50") used as
      a template for dsRNA

<400> SEQUENCE: 127
gggagaatga ctgagtattg gttgatatct gccccagggg ataagacctg tcaacatctc    60
cc                                                                  62

<210> SEQ ID NO 128
<211> LENGTH: 112
<212> TYPE: DNA
<213> ORGANISM: Artificial
<220> FEATURE:
<223> OTHER INFORMATION: VatpaseC sense strand ("VatpaseC5'-100") used
      as a template for dsRNA

<400> SEQUENCE: 128
gggagaatga ctgagtattg gttgatatct gccccagggg ataagacctg tcaacagaca    60
tgggacacga tgaataatat gacaagtaaa cagaataatt tgtcaatctc cc          112

<210> SEQ ID NO 129
<211> LENGTH: 186
<212> TYPE: DNA
<213> ORGANISM: Artificial
<220> FEATURE:
<223> OTHER INFORMATION: VatpaseC sense strand ("VatpaseC-174") used as
      a template for dsRNA

<400> SEQUENCE: 129
gggagaatga ctgagtattg gttgatatct gccccagggg ataagacctg tcaacagaca    60
tgggacacga tgaataatat gacaagtaaa cagaataatt tgtcaaccaa ctacaagttt   120
caaatcccgg acttgaaagt tggtactctg gatcagttag taggactttc tgatgatctg   180
tctccc                                                             186

<210> SEQ ID NO 130
<211> LENGTH: 63
<212> TYPE: DNA
<213> ORGANISM: Artificial
<220> FEATURE:
<223> OTHER INFORMATION: VatpaseC sense strand ("VatpaseC3'-50") used as
      a template for dsRNA

<400> SEQUENCE: 130
gggagagact tgaaagttgg tactctggat cagttagtag gactttctga tgatctgtct    60
ccc                                                                 63

<210> SEQ ID NO 131
<211> LENGTH: 112
<212> TYPE: DNA
<213> ORGANISM: Artificial
<220> FEATURE:
<223> OTHER INFORMATION: VatpaseC sense strand ("VatpaseC3'-100") used
      as a template for dsRNA
```

<400> SEQUENCE: 131
gggagagaca agtaaacaga ataatttgtc aaccaactac aagtttcaaa tcccggactt      60
gaaagttggt actctggatc agttagtagg actttctgat gatctgtctc cc            112

<210> SEQ ID NO 132
<211> LENGTH: 20
<212> TYPE: DNA
<213> ORGANISM: Artificial
<220> FEATURE:
<223> OTHER INFORMATION: Primer MZTIPU67F

<400> SEQUENCE: 132
agccaagcca gtggtacttc                                                 20

<210> SEQ ID NO 133
<211> LENGTH: 22
<212> TYPE: DNA
<213> ORGANISM: Artificial
<220> FEATURE:
<223> OTHER INFORMATION: Primer MZTIPU67R

<400> SEQUENCE: 133
tcgcagacaa agtagcaaat gt                                              22

<210> SEQ ID NO 134
<211> LENGTH: 20
<212> TYPE: DNA
<213> ORGANISM: Artificial
<220> FEATURE:
<223> OTHER INFORMATION: Primer P5U76S

<400> SEQUENCE: 134
ttgtgatgtt ggtggcgtat                                                 20

<210> SEQ ID NO 135
<211> LENGTH: 24
<212> TYPE: DNA
<213> ORGANISM: Artificial
<220> FEATURE:
<223> OTHER INFORMATION: Primer P5U76A

<400> SEQUENCE: 135
tgttaaataa aaccccaaag atcg                                            24

<210> SEQ ID NO 136
<211> LENGTH: 189
<212> TYPE: DNA
<213> ORGANISM: Artificial
<220> FEATURE:
<223> OTHER INFORMATION: ST-LS1 intron

<400> SEQUENCE: 136
gtatgtttct gcttctacct ttgatatata tataataatt atcactaatt agtagtaata      60
tagtatttca agtatttttt tcaaaataaa agaatgtagt atatagctat tgcttttctg     120
tagtttataa gtgtgtatat tttaatttat aactttctta atatatgacc aaaacatggt     180
gatgtgcag                                                            189

<210> SEQ ID NO 137
<211> LENGTH: 48
<212> TYPE: DNA
<213> ORGANISM: Diabrotica virgifera

```
<400> SEQUENCE: 137
aaattggact aaactttttt gctcgtttwg ttaatcttat ccattaat            48

<210> SEQ ID NO 138
<211> LENGTH: 102
<212> TYPE: DNA
<213> ORGANISM: Diabrotica virgifera

<400> SEQUENCE: 138
gttacgtgtg ttaattaatt tactaagggg gacgttctgt catgatgtat tgacaagggg    60
gcttctgcat gatgtattga ctaacaaaaa taaaccccwt ta                      102
```

NUCLEIC ACID MOLECULES THAT TARGET THE RHO1 SMALL GTP-BINDING PROTEIN AND CONFER RESISTANCE TO COLEOPTERAN PESTS

PRIORITY CLAIM

This application claims the benefit of the filing date of U.S. Provisional Patent Application Ser. No. 61/428,688, filed Dec. 30, 2010, for "Nucleic Acid Molecules That Target the RHO1 Small GTP-Binding Protein and Confer Resistance to Coleopteran Pests."

FIELD OF THE DISCLOSURE

The present invention relates generally to genetic control of plant damage caused by coleopteran pests. In particular embodiments, the present invention relates to identification of target coding and non-coding sequences, and the use of recombinant DNA technologies for post-transcriptionally repressing or inhibiting expression of target coding and non-coding sequences in the cells of a coleopteran pest to provide a plant protective effect.

BACKGROUND

The western corn rootworm (WCR), *Diabrotica virgifera virgifera* LeConte, is one of the most devastating corn rootworm species in North America and is a particular concern in corn-growing areas of the Midwestern United States. The northern corn rootworm (NCR), *Diabrotica barberi* Smith and Lawrence, is a closely-related species that co-inhabits much of the same range as WCR. There are several other related subspecies of *Diabrotica* that are significant pests in North America: the Mexican corn rootworm (MCR), *D. virgifera zeae* Krysan and Smith; the southern corn rootworm (SCR), *D. undecimpunctata howardi* Barber; *D. balteata* LeConte; *D. undecimpunctata tenella*; and *D. u. undecimpunctata* Mannerheim. The United States Department of Agriculture currently estimates that corn rootworms cause $1 billion in lost revenue each year, including $800 million in yield loss and $200 million in treatment costs.

Both WCR and NCR are deposited in the soil as eggs during the summer. The insects remain in the egg stage throughout the winter. The eggs are oblong, white, and less than 0.004 inches in length. The larvae hatch in late May or early June, with the precise timing of egg hatching varying from year to year due to temperature differences and location. The newly hatched larvae are white worms that are less than 0.125 inches in length. Once hatched, the larvae begin to feed on corn roots. Corn rootworms go through three larval instars. After feeding for several weeks, the larvae molt into the pupal stage. They pupate in the soil, and then they emerge from the soil as adults in July and August. Adult rootworms are about 0.25 inches in length.

Corn rootworm larvae complete development on corn and several other species of grasses. Larvae reared on yellow foxtail emerge later and have a smaller head capsule size as adults than larvae reared on corn. Ellsbury et al. (2005) Environ. Entomol. 34:627-34. WCR adults feed on corn silk, pollen, and kernels on exposed ear tips. If WCR adults emerge before corn reproductive tissues are present, they may feed on leaf tissue, thereby slowing plant growth and occasionally killing the host plant. However, the adults will quickly shift to preferred silks and pollen when they become available. NCR adults also feed on reproductive tissues of the corn plant, but in contrast rarely feed on corn leaves.

Most of the rootworm damage in corn is caused by larval feeding. Newly hatched rootworms initially feed on fine corn root hairs and burrow into root tips. As the larvae grow larger, they feed on and burrow into primary roots. When corn rootworms are abundant, larval feeding often results in the pruning of roots all the way to the base of the corn stalk. Severe root injury interferes with the roots' ability to transport water and nutrients into the plant, reduces plant growth, and results in reduced grain production, thereby often drastically reducing overall yield. Severe root injury also often results in lodging of corn plants, which makes harvest more difficult and further decreases yield. Furthermore, feeding by adults on the corn reproductive tissues can result in pruning of silks at the ear tip. If this "silk clipping" is severe enough during pollen shed, pollination may be disrupted.

Control of corn rootworms may be attempted by crop rotation, chemical insecticides, biopesticides (e.g., the spore-forming gram-positive bacterium, *Bacillus thuringiensis*), or a combination thereof. Crop rotation suffers from the significant disadvantage of placing unwanted restrictions upon the use of farmland. Moreover, oviposition of some rootworm species may occur in soybean fields, thereby mitigating the effectiveness of crop rotation practiced with corn and soybean.

Chemical insecticides are the most heavily relied upon strategy for achieving corn rootworm control. Chemical insecticide use, though, is an imperfect corn rootworm control strategy; over $1 billion may be lost in the United States each year due to corn rootworm when the costs of the chemical insecticides are added to the costs of the rootworm damage that may occur despite the use of the insecticides. High populations of larvae, heavy rains, and improper application of the insecticide(s) may all result in inadequate corn rootworm control. Furthermore, the continual use of insecticides may select for insecticide-resistant rootworm strains, as well as raise significant environmental concerns due to the toxicity of many of them to non-target species.

RNA interference (RNAi) is a process utilizing endogenous cellular pathways, whereby an interfering RNA (iRNA) molecule (e.g., a dsRNA molecule) that is specific for all, or any portion of adequate size, of a target gene sequence results in the degradation of the mRNA encoded thereby. In recent years, RNAi has been used to perform gene "knock-down" in a number of species and experimental systems; for example, *C. elegans*, plants, insect embryos, and cells in tissue culture. See, e.g., Fire et al. (1998) Nature 391:806-11; Martinez et al. (2002) Cell 110:563-74; McManus and Sharp (2002) Nature Rev. Genetics 3:737-47.

RNAi accomplishes degradation of mRNA through an endogenous pathway including the DICER protein complex. DICER cleaves long dsRNA molecules into short fragments of approximately 20 nucleotides, termed small interfering RNA (siRNA). The siRNA is unwound into two single-stranded RNAs: the passenger strand and the guide strand. The passenger strand is degraded, and the guide strand is incorporated into the RNA-induced silencing complex (RISC). Micro inhibitory ribonucleic acid (miRNA) molecules may be similarly incorporated into RISC. Post-transcriptional gene silencing occurs when the guide strand binds specifically to a complementary sequence of an mRNA molecule and induces cleavage by Argonaute, the catalytic component of the RISC complex. This process is known to spread systemically throughout the organism despite initially limited concentrations of siRNA and/or miRNA in some eukaryotes such as plants, nematodes, and some insects.

Only transcripts complementary to the siRNA and/or miRNA are cleaved and degraded, and thus the knock-down of mRNA expression is sequence-specific. In plants, several functional groups of DICER genes exist. The gene silencing effect of RNAi persists for days and, under experimental conditions, can lead to a decline in abundance of the targeted transcript of 90% or more, with consequent reduction in levels of the corresponding protein.

U.S. Pat. No. 7,612,194 and U.S. Patent Publication Nos. US 2007/0050860, US 2010/0192265, and US 2011/0154545 disclose a library of 9112 expressed sequence tag (EST) sequences isolated from *D. v. virgifera* LeConte pupae. It is suggested in U.S. Pat. No. 7,612,194 and U.S. Patent Publication No. US 2007/0050860 to operably link to a promoter a nucleic acid molecule that is complementary to one of several particular partial sequences of *D. v. virgifera* vacuolar-type $H^+$-ATPase (V-ATPase) disclosed therein for the expression of anti-sense RNA in plant cells. U.S. Patent Publication No. US 2010/0192265 suggests operably linking a promoter to a nucleic acid molecule that is complementary to a particular partial sequence of a *D. v. virgifera* gene of unknown and undisclosed function (the partial sequence is stated to be 58% identical to C56C10.3 gene product in *C. elegans*) for the expression of anti-sense RNA in plant cells. U.S. Patent Publication No. US 2011/0154545 suggests operably linking a promoter to a nucleic acid molecule that is complementary to two particular partial sequences of *D. v. virgifera* coatomer beta subunit genes for the expression of anti-sense RNA in plant cells. Further, U.S. Pat. No. 7,943,819 discloses a library of 906 expressed sequence tag (EST) sequences isolated from *D. v. virgifera* LeConte larvae, pupae, and dissected midgets, and suggests operably linking a promoter to a nucleic acid molecule that is complementary to a particular partial sequence of a *D. v. virgifera* charged multivesicular body protein 4b gene for the expression of double-stranded RNA in plant cells.

No further suggestion is provided in U.S. Pat. No. 7,612,194, and U.S. Patent Publication Nos. US 2007/0050860, US 2010/0192265 and US 2011/0154545 to use any particular sequence of the more than nine thousand sequences listed therein for RNA interference, other than the several particular partial sequences of V-ATPase and the particular partial sequences of genes of unknown function. Furthermore, none of U.S. Pat. No. 7,612,194, and U.S. Patent Publication Nos. US 2007/0050860 and US 2010/0192265, and US 2011/0154545 provides any guidance as to which other of the over nine thousand sequences provided would be lethal, or even otherwise useful, in species of corn rootworm when used as dsRNA or siRNA. U.S. Pat. No. 7,943,819 provides no suggestion to use any particular sequence of the more than nine hundred sequences listed therein for RNA interference, other than the particular partial sequence of a charged multivesicular body protein 4b gene. Furthermore, U.S. Pat. No. 7,943,819 provides no guidance as to which other of the over nine hundred sequences provided would be lethal, or even otherwise useful, in species of corn rootworm when used as dsRNA or siRNA.

The overwhelming majority of sequences complementary to corn rootworm DNAs (such as the foregoing) are not lethal in species of corn rootworm when used as dsRNA or siRNA. For example, Baum et al. (2007), describe the effects of inhibiting several WCR gene targets by RNAi. These authors reported that the 8 of 26 target genes they tested were not able to provide experimentally significant coleopteran pest mortality at a very high iRNA (e.g., dsRNA) concentration of more than 520 ng/cm$^2$.

SUMMARY OF THE DISCLOSURE

Disclosed herein are nucleic acid molecules (e.g., target genes, DNAs, dsRNAs, siRNAs, miRNAs, and hpRNAs), and methods of use thereof, for the control of coleopteran pests, including, for example, *D. v. virgifera* LeConte (western corn rootworm, "WCR"); *D. barberi* Smith and Lawrence (northern corn rootworm, "NCR"); *D. u. howardi* Barber (southern corn rootworm, "SCR"); *D. v. zeae* Krysan and Smith (Mexican corn rootworm, "MCR"); *D. balteata* LeConte; *D. u. tenella*; and *D. u. undecimpunctata* Mannerheim. In particular examples, exemplary nucleic acid molecules are disclosed that may be homologous to at least a portion of one or more native nucleic acid sequences in a coleopteran pest.

In these and further examples, the native nucleic acid sequence may be a target gene, the product of which may be, for example and without limitation: involved in a metabolic process; involved in a reproductive process; or involved in larval development. In some examples, post-translation inhibition of the expression of a target gene by a nucleic acid molecule comprising a sequence homologous thereto may be lethal in coleopteran pests, or result in reduced growth and/or reproduction. In specific examples, at least one gene selected from the list consisting of Contig_01_Rho1_1-191_CDC42; D_vir_c47185_Caf1 180; D_vir_c1229_VatpaseC; and D_vir_c1319_VatpaseH may be selected as a target gene for post-transcriptional silencing. In particular examples, a target gene useful for post-translational inhibition is a Rho1 small GTP-binding protein comprising a nucleotide sequence referred to herein as Contig_01_Rho1_1-191_CDC42 (SEQ ID NO:4), or a homolog thereof. Isolated nucleic acid molecules comprising the sequence of Contig_01_Rho1_1-191_CDC42 (SEQ ID NO:4), its complement, and certain novel fragments of either are therefore disclosed herein.

Also disclosed are nucleic acid molecules comprising a nucleotide sequence that encodes a polypeptide that is at least 85% identical to an amino acid sequence within a target gene product (for example, the product of a gene selected from the group consisting of Contig_01_Rho1_1-191_CDC42; D_vir_c47185_Caf1 180; D_vir_c1229_VatpaseC; and D_vir_c1319_VatpaseH). In particular examples, a nucleic acid molecule comprises a nucleotide sequence encoding a polypeptide that is at least 85% identical to an amino acid sequence within a polypeptide encoded by a Rho1 small GTP-binding protein gene comprising a nucleotide sequence referred to herein as Contig_01_Rho1_1-191_CDC42 (SEQ ID NO:4), or a homolog thereof. Further disclosed are nucleic acid molecules comprising a nucleotide sequence that is the reverse complement of a nucleotide sequence that encodes a polypeptide at least 85% identical to an amino acid sequence within a target gene product.

Also disclosed are cDNA sequences that may be used for the production of iRNA (e.g., dsRNA, siRNA, miRNA, and hpRNA) molecules that are complementary to all or part of a coleopteran pest target gene, for example: Contig_01_Rho1_1-191_CDC42; D_vir_c47185 Caf1 180; D_vir_c1229_VatpaseC; or D_vir_c1319_VatpaseH. In particular embodiments, dsRNAs, siRNAs, miRNAs, and/or hpRNAs may be produced in vitro, or in vivo by a genetically-modified organism, such as a plant or bacterium. In particular examples, cDNA molecules are disclosed that may be used to produce iRNA molecules that are complementary to Contig_01_Rho1_1-191_CDC42, or certain novel fragments thereof.

Further disclosed are means for inhibiting expression of an essential gene in a coleopteran pest, and means for providing coleopteran pest resistance to a plant. A means for inhibiting expression of an essential gene in a coleopteran pest is a single- or double-stranded RNA molecule consisting of any of SEQ ID NOs:7, 8, 10, 11, 49, 50, 86, 87, 91, 92, 93, 94, 95, 96, 97, 98, 99, 100, 101, 102, 103, 104, 105, 106, 107, 108, 109, 110, 111, 112, 113, 114, 115, 116, 127, 128, 129, 130, 131, or the complement thereof. A means for providing coleopteran pest resistance to a plant is a DNA molecule comprising a nucleic acid sequence encoding a means for inhibiting expression of an essential gene in a coleopteran pest operably linked to a promoter, wherein the DNA molecule is capable of being integrated into the genome of a maize plant.

Disclosed are methods for controlling a population of a coleopteran pest, comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises all or part of a nucleotide sequence selected from the group the group consisting of: SEQ ID NO:1; the complement of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; a native coding sequence of a *Diabrotica* organism (e.g., WCR) comprising all or part of any of SEQ ID NOs:1-4; the complement of a native coding sequence of a *Diabrotica* organism comprising all or part of any of SEQ ID NOs:1-4; a native non-coding sequence of a *Diabrotica* organism that is transcribed into a native RNA molecule comprising all or part of any of SEQ ID NOs:1-4; and the complement of a native non-coding sequence of a *Diabrotica* organism that is transcribed into a native RNA molecule comprising all or part of any of SEQ ID NOs:1-4.

In particular examples, methods are disclosed for controlling a population of a coleopteran pest, comprising providing to a coleopteran pest an iRNA (e.g., dsRNA, siRNA, miRNA, and hpRNA) molecule that functions upon being taken up by the coleopteran pest to inhibit a biological function within the coleopteran pest, wherein the iRNA molecule comprises a nucleotide sequence selected from the group the group consisting of: all or part of SEQ ID NO:1; the complement of all or part of SEQ ID NO:1; SEQ ID NO:2; the complement of SEQ ID NO:2; SEQ ID NO:3; the complement of SEQ ID NO:3; SEQ ID NO:4; the complement of SEQ ID NO:4; SEQ ID NO:87; the complement of SEQ ID NO:87; all or part of SEQ ID NO:88; all or part of the complement of SEQ ID NO:88; all or part of SEQ ID NO:89; all or part of the complement of SEQ ID NO:89; all or part of SEQ ID NO:90; all or part of the complement of SEQ ID NO:90; all or part of SEQ ID NO:137; all or part of the complement of SEQ ID NO:137; all or part of SEQ ID NO:138; all or part of the complement of SEQ ID NO:138; all or part of a native coding sequence of a *Diabrotica* organism comprising SEQ ID NO:1; all or part of the complement of a native coding sequence of a *Diabrotica* organism comprising SEQ ID NO:1; all or part of a native non-coding sequence of a *Diabrotica* organism that is transcribed into a native RNA molecule comprising SEQ ID NO:1; and all or part of the complement of a native non-coding sequence of a *Diabrotica* organism that is transcribed into a native RNA molecule comprising SEQ ID NO:1.

Also disclosed herein are methods wherein dsRNAs, siRNAs, miRNAs, and/or hpRNAs may be provided to a coleopteran pest in a diet-based assay, or in genetically-modified plant cells expressing the dsRNAs, siRNAs, miRNAs, and/or hpRNAs. In these and further examples, the dsRNAs, siRNAs, miRNAs, and/or hpRNAs may be ingested by coleopteran pest larvae. Ingestion of dsRNAs, siRNA, miRNAs, and/or hpRNAs of the invention may then result in RNAi in the larvae, which in turn may result in silencing of a gene essential for viability of the coleopteran pest and leading ultimately to larval mortality. Thus, methods are disclosed wherein nucleic acid molecules comprising exemplary nucleic acid sequence(s) useful for control of coleopteran pests are provided to a coleopteran pest. In particular examples, the coleopteran pest controlled by use of nucleic acid molecules of the invention may be WCR or NCR.

The foregoing and other features will become more apparent from the following Detailed Description of several embodiments, which proceeds with reference to the accompanying Figures.

BRIEF DESCRIPTION OF THE FIGURES

FIG. 5 includes a cartoon depiction of several nucleotide sequences that may be present in certain nucleic acid molecules of the invention. Where indicated, "(sequence)," refers to a region of the depicted nucleotide sequence having any length and particular sequence, for example and without limitation, a contiguous segment of one of SEQ ID NOs:1-4. Italicized regions of the depicted nucleotide sequences are optional.

SEQUENCE LISTING

Figure 1:
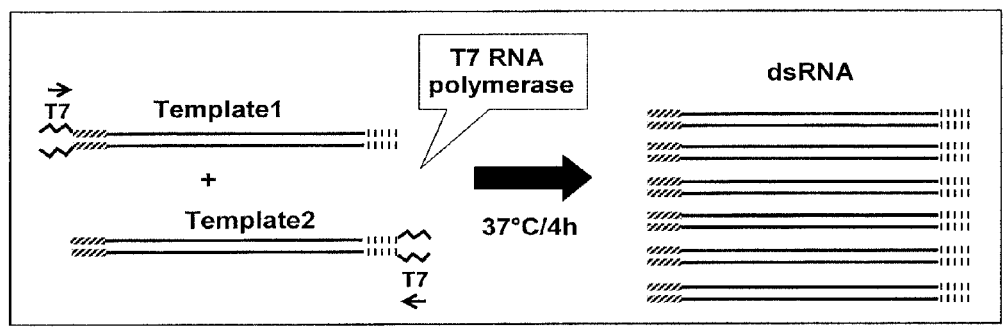
FIG. 1 includes a depiction of the strategy used to provide specific templates for dsRNA production.

The nucleic acid sequences listed in the accompanying sequence listing are shown using standard letter abbreviations for nucleotide bases, as defined in 37 C.F.R. §1.822. Only one strand of each nucleic acid sequence is shown, but the complementary strand and reverse complementary strand are understood as included by any reference to the displayed strand. In the accompanying sequence listing:

SEQ ID NO:1 shows an exemplary *Diabrotica* cDNA sequence, referred to in some places as D_vir_c47185Caf1 180, or Caf1-180.

SEQ ID NO:2 shows an exemplary *Diabrotica* cDNA sequence, referred to in some places as D_vir_c1229_VatpaseC, or VatpaseC.

SEQ ID NO:3 shows an exemplary *Diabrotica* cDNA sequence, referred to in some places as D_vir_c1319_VatpaseH, or VatpaseH.

SEQ ID NO:4 shows an exemplary *Diabrotica* cDNA sequence, referred to in some places as Contig_01_Rho1_1-191_CDC42, or Rho1.

SEQ ID NOs:5-8 show exemplary non-contiguous fragments of a *Diabrotica* vacuolar ATPase C subunit cDNA.

SEQ ID NOs:9-11 show exemplary non-contiguous fragments of a *Diabrotica* vacuolar ATPase H subunit cDNA.

SEQ ID NO:12 shows a T7 phage promoter sequence.

SEQ ID NOs:13-38 show primers used to amplify portions of coding regions of exemplary target genes by PCR.

SEQ ID NOs:39-48 show primers used to amplify gene regions of Caf1-180 and VatpaseC for hairpin RNA synthesis.

SEQ ID NO:49 shows a Caf1-180 hairpin RNA-forming DNA sequence containing an ST-LS1 intron (SEQ ID NO:136) for a version 1 expression vector that contains a maize consensus sequence.

SEQ ID NO:50 shows a VatpaseC hairpin RNA-forming DNA sequence containing an ST-LS1 intron (SEQ ID NO:136) for a version 1 hpRNA expression vector that contains a maize consensus sequence.

SEQ ID NO:51 shows a DNA sequence of annexin region 1.

SEQ ID NO:52 shows a DNA sequence of annexin region 2.

SEQ ID NO:53 shows a DNA sequence of beta spectrin 2 region 1.

SEQ ID NO:54 shows a DNA sequence of beta spectrin 2 region 2.

SEQ ID NO:55 shows a DNA sequence of mtRP-L4 region 1.

SEQ ID NO:56 shows a DNA sequence of mtRP-L4 region 2.

SEQ ID NO:57 shows a DNA sequence encoding a YFP.

SEQ ID NOs:58-85 show primers used to amplify gene regions of annexin, beta spectrin 2, mtRP-L4, and YFP for dsRNA synthesis.

SEQ ID NO:86 shows an exemplary 260 bp amplified fragment of a D_vir_c47185 Caf1-180 cDNA that was used as a template for the synthesis of a dsRNA molecule.

SEQ ID NOs:87-90 show exemplary non-contiguous fragments of a *Diabrotica* Rho1 cDNA.

SEQ ID NO:91 shows an exemplary Caf1-180 hairpin RNA-forming DNA sequence containing an ST-LS1 intron (SEQ ID NO:136), including an optional cloning site flanking the intron, for a version 1 expression vector that contains a maize consensus sequence.

SEQ ID NO:92 shows an exemplary Caf1-180 hairpin RNA-forming DNA sequence containing an ST-LS1 intron (SEQ ID NO:136) for a version 2 expression vector that does not contain the maize consensus sequence.

SEQ ID NO:93 shows an exemplary VatpaseC hairpin RNA-forming DNA sequence containing an ST-LS1 intron (SEQ ID NO:136), including an optional cloning site flanking the intron, for a version 1 hpRNA expression vector that contains a maize consensus sequence.

SEQ ID NO:94 shows an exemplary VatpaseC hairpin RNA-forming DNA sequence containing an ST-LS1 intron (SEQ ID NO:136) for a version 2 hpRNA expression vector that does not contain the maize consensus sequence.

SEQ ID NO:95 shows an exemplary segment of a Caf1-180 DNA sense strand containing an ST-LS1 intron (SEQ ID NO:136) for a version 3 expression vector.

SEQ ID NO:96 shows an exemplary segment of a Caf1-180 DNA antisense strand for a version 3 expression vector.

SEQ ID NO:97 shows an exemplary Caf1-180 hairpin RNA-forming DNA sequence containing an ST-LS1 intron (SEQ ID NO:136) for a version 3 expression vector.

SEQ ID NO:98 shows an exemplary segment of a VatpaseC DNA sense strand containing an ST-LS1 intron (SEQ ID NO:136) for a version 3 expression vector.

SEQ ID NO:99 shows an exemplary segment of a VatpaseC DNA antisense strand for a version 3 expression vector.

SEQ ID NO:100 shows an exemplary VatpaseC hairpin RNA-forming DNA sequence containing an ST-LS1 intron (SEQ ID NO:136) for a version 3 expression vector.

SEQ ID NO:101 shows an exemplary segment of a VatpaseC DNA sense strand containing an ST-LS1 intron (SEQ ID NO:136) for a version 4 expression vector.

SEQ ID NO:102 shows an exemplary segment of a VatpaseC DNA antisense strand for a version 4 expression vector.

SEQ ID NO:103 shows an exemplary VatpaseC hairpin RNA-forming DNA sequence containing an ST-LS1 intron (SEQ ID NO:136) for a version 4 expression vector.

SEQ ID NO:104 shows an exemplary segment of a VatpaseH DNA sense strand containing an ST-LS1 intron (SEQ ID NO:136) for a version 1 expression vector.

SEQ ID NO:105 shows an exemplary segment of a VatpaseH DNA antisense strand for a version 1 expression vector.

SEQ ID NO:106 shows an exemplary VatpaseH hairpin RNA-forming DNA sequence containing an ST-LS1 intron (SEQ ID NO:136) for a version 1 expression vector.

SEQ ID NO:107 shows an exemplary segment of a Rho1 DNA sense strand containing an ST-LS1 intron (SEQ ID NO:136) for a version 1 expression vector.

SEQ ID NO:108 shows an exemplary segment of a Rho1 DNA antisense strand for a version 1 expression vector.

SEQ ID NO:109 shows an exemplary Rho1 hairpin RNA-forming DNA sequence containing an ST-LS1 intron (SEQ ID NO:136) for a version 1 expression vector.

SEQ ID NO:110 shows an exemplary segment of a Caf-180 DNA used to provide a template for dsRNA synthesis in diet feeding bioassays.

SEQ ID NO:111 shows an exemplary segment of a VatpaseC region 1 DNA used to provide a template for dsRNA synthesis in diet feeding bioassays.

SEQ ID NO:112 shows an exemplary segment of a VatpaseC region 1 (short) DNA used to provide a template for dsRNA synthesis in diet feeding bioassays.

SEQ ID NO:113 shows an exemplary segment of a VatpaseC region 2 DNA used to provide a template for dsRNA synthesis in diet feeding bioassays.

SEQ ID NO:114 shows an exemplary segment of a VatpaseH region 1 DNA used to provide a template for dsRNA synthesis in diet feeding bioassays.

SEQ ID NO:115 shows an exemplary segment of a VatpaseH region 2 DNA used to provide a template for dsRNA synthesis in diet feeding bioassays.

SEQ ID NO:116 shows an exemplary segment of a Rho1 DNA used to provide a template for dsRNA synthesis in diet feeding bioassays.

SEQ ID NO:117 shows an exemplary VatpaseC RNA sense strand ("VatpaseC5'-15") used as a dsRNA in diet feeding bioassays.

SEQ ID NO:118 shows a further exemplary VatpaseC RNA sense strand ("VatpaseC5'-25") used as a dsRNA in diet feeding bioassays.

SEQ ID NO:119 shows a further exemplary VatpaseC RNA sense strand ("VatpaseC3'-15") used as a dsRNA in diet feeding bioassays.

SEQ ID NO:120 shows a further exemplary VatpaseC RNA sense strand ("VatpaseC3'-25") used as a dsRNA in diet feeding bioassays.

SEQ ID NOs:121-126 show primers used to amplify portions of a *Diabrotica* VatpaseC gene as templates for dsRNA synthesis.

SEQ ID NO:127 shows an exemplary VatpaseC sense strand ("VatpaseC5'-50") used as a template for dsRNA in diet feeding bioassays.

SEQ ID NO:128 shows an exemplary VatpaseC sense strand ("VatpaseC5'-100") used as a template for dsRNA in diet feeding bioassays.

SEQ ID NO:129 shows an exemplary VatpaseC sense strand ("VatpaseC-174") used as a template for dsRNA in diet feeding bioassays.

SEQ ID NO:130 shows an exemplary VatpaseC sense strand ("VatpaseC3'-50") used as a template for dsRNA in diet feeding bioassays.

SEQ ID NO:131 shows an exemplary VatpaseC sense strand ("VatpaseC3'-100") used as a dsRNA in diet feeding bioassays.

SEQ ID NOs:132-135 show primers used for molecular analyses of transgenic maize.

SEQ ID NO:136 shows a ST-LS1 intron that may be useful in some embodiments for forming a hairpin RNA.

SEQ ID NOs:137-138 show exemplary non-contiguous fragments of a *Diabrotica* Rho1 cDNA:

DETAILED DESCRIPTION

I. Overview of Several Embodiments

Disclosed herein are methods and compositions for genetic control of coleopteran pest infestations. Methods for identifying one or more gene(s) essential to the lifecycle of a coleopteran pest for use as a target gene for RNAi-mediated control of a coleopteran pest population are also provided. DNA plasmid vectors encoding dsRNA molecules may be designed to suppress one or more target gene(s) essential for growth, survival, development, and/or reproduction. In some embodiments, provides methods are provided for post-transcriptional repression of expression or inhibition of a target gene via nucleic acid molecules that are complementary to a coding or non-coding sequence of the target gene in a coleopteran pest. In these and further embodiments, a coleopteran pest may ingest one or more dsRNA, siRNA, miRNA, and/or hpRNA molecules transcribed from all or a portion of a nucleic acid molecule that is complementary to a coding or non-coding sequence of a target gene, thereby providing a plant-protective effect.

Thus, some embodiments involve sequence-specific inhibition of expression of target gene products, using dsRNA, siRNA, miRNA, and/or hpRNA that is complementary to coding and/or non-coding sequences of the target gene(s) to achieve at least partial control of a coleopteran pest. Disclosed is a set of isolated and purified nucleic acid molecules comprising a nucleotide sequence, for example, as set forth in one of SEQ ID NOs:1-4, 87-90, 137, and 138. In some embodiments, a stabilized dsRNA molecule may be expressed from these sequences, fragments thereof, or a gene comprising one of these sequences, for the post-transcriptional silencing or inhibition of a target gene. In certain embodiments, isolated and purified nucleic acid molecules comprise SEQ ID NO:4 and/or all or part of any of SEQ ID NOs:88-90, 137, and 138.

Some embodiments involve a recombinant host cell (e.g., a plant cell) having in its genome at least one recombinant DNA sequence encoding at least one iRNA (e.g., dsRNA) molecule(s). In particular embodiments, the dsRNA molecule(s) may be expressed when ingested by a coleopteran pest to post-transcriptionally silence or inhibit the expression of a target gene in the coleopteran pest. The recombinant DNA sequence may comprise, for example, any of SEQ ID NOs:1-4, 87-90, 137, and 138, fragments of any of SEQ ID NOs:1-4, 87-90, 137, and 138, or a partial sequence of a gene comprising one of SEQ ID NOs:1-4, 87-90, 137, and 138, or complements thereof.

Particular embodiments involve a recombinant host cell having in its genome a recombinant DNA sequence encoding at least one iRNA (e.g., dsRNA) molecule(s) comprising SEQ ID NO:4 and/or all or part of any of SEQ ID NOs:88-90, 137, and 138. When ingested by a coleopteran pest, the iRNA molecule(s) may silence or inhibit the expression of a target Rho1 small GTP-binding protein gene comprising SEQ ID NOs:4, 87-90, 137, and 138 in the coleopteran pest, and thereby result in cessation of growth, development, reproduction, and/or feeding in the coleopteran pest.

In some embodiments, a recombinant host cell having in its genome at least one recombinant DNA sequence encoding at least one dsRNA molecule may be a transformed plant cell. Some embodiments involve transgenic plants comprising such a transformed plant cell. In addition to such transgenic plants, progeny plants of any transgenic plant generation, transgenic seeds, and transgenic plant products, are all provided, each of which comprises recombinant DNA sequence(s). In particular embodiments, a dsRNA molecule of the invention may be expressed in a transgenic plant cell. Therefore, in these and other embodiments, a dsRNA molecule of the invention may be isolated from a transgenic plant cell. In particular embodiments, the transgenic plant is a plant selected from the group comprising corn (*Zea mays*), soybean (*Glycine max*), and plants of the family Poaceae.

Some embodiments involve a method for modulating the expression of a target gene in a coleopteran pest cell. In these and other embodiments, a nucleic acid molecule may be provided, wherein the nucleic acid molecule comprises a nucleotide sequence encoding a dsRNA molecule. In particular embodiments, a nucleotide sequence encoding a dsRNA molecule may be operatively linked to a promoter, and may also be operatively linked to a transcription termination sequence. In particular embodiments, a method for modulating the expression of a target gene in a coleopteran pest cell may comprise: (a) transforming a plant cell with a vector comprising a nucleotide sequence encoding a dsRNA molecule; (b) culturing the transformed plant cell under conditions sufficient to allow for development of a plant cell culture comprising a plurality of transformed plant cells; (c) selecting for a transformed plant cell that has integrated the vector into its genome; and (d) determining that the selected transformed plant cell comprises the dsRNA molecule encoded by the nucleotide sequence of the vector. A plant may be regenerated from a plant cell that has the vector integrated in its genome and comprises the dsRNA molecule encoded by the nucleotide sequence of the vector.

Thus, also disclosed is a transgenic plant comprising a vector having a nucleotide sequence encoding a dsRNA molecule integrated in its genome, wherein the transgenic plant comprises the dsRNA molecule encoded by the nucleotide sequence of the vector. In particular embodiments, expression of a dsRNA molecule in the plant is sufficient to modulate the expression of a target gene in a cell of a coleopteran pest that contacts the transformed plant or plant cell, for example, by feeding on the transformed plant, a part of the plant (e.g., root) or plant cell. Transgenic plants disclosed herein may display resistance and/or enhanced tolerance to coleopteran pest infestations. Particular transgenic plants may display resistance and/or enhanced tolerance to one or more coleopteran pests selected from the group consisting of: WCR; NCR; SCR; MCR; *D. balteata* LeConte; *D. u. tenella*; and *D. u. undecimpunctata* Mannerheim.

Also disclosed herein are methods for delivery of control agents, such as an iRNA molecule, to a coleopteran pest. Such control agents may cause, directly or indirectly, an impairment in the ability of the coleopteran pest to feed, grow or otherwise cause damage to a host. In some embodiments, a method is provided comprising delivery of a stabilized dsRNA molecule to a coleopteran pest to suppress at least one target gene in the coleopteran pest, thereby reducing or eliminating plant damage by a coleopteran pest. In some embodiments, a method of inhibiting expression of a target gene in a coleopteran pest may result in the cessation of growth, development, reproduction, and/or feeding in the coleopteran pest. In some embodiments, the method may eventually result in death of the coleopteran pest.

In some embodiments, compositions (e.g., a topical composition) are provided that comprise an iRNA (e.g., dsRNA) molecule of the invention for use in plants, animals, and/or the environment of a plant or animal to achieve the elimination or reduction of a coleopteran pest infestation. In particular embodiments, the composition may be a nutritional composition or food source to be fed to the coleopteran pest. Some embodiments comprise making the nutritional composition or food source available to the coleopteran pest. Ingestion of a composition comprising iRNA molecules may result in the uptake of the molecules by one or more cells of the coleopteran pest, which may in turn result in the inhibition of expression of at least one target gene in cell(s) of the coleopteran pest. Ingestion of or damage to a plant or plant cell by a coleopteran pest may be limited or eliminated in or on any host tissue or environment in which the coleopteran pest is present by providing one or more compositions comprising an iRNA molecule of the invention in the host of the coleopteran pest.

The compositions and methods disclosed herein may be used together in combinations with other methods and compositions for controlling damage by coleopteran pests. For example, an iRNA molecule as described herein for protecting plants from coleopteran pests may be used in a method comprising the additional use of one or more chemical agents effective against a coleopteran pest, biopesticides effective against a coleopteran pest, crop rotation, or recombinant genetic techniques that exhibit features different from the features of the RNAi-mediated methods and RNAi compositions of the invention (e.g., recombinant production of proteins in plants that are harmful to a coleopteran pest (e.g., Bt toxins)).

II. Abbreviations

- dsRNA double-stranded ribonucleic acid
- GI growth inhibition
- NCBI National Center for Biotechnology Information
- gDNA genomic DNA
- iRNA inhibitory ribonucleic acid
- ORF open reading frame
- RNAi ribonucleic acid interference
- miRNA micro inhibitory ribonucleic acid
- siRNA small inhibitory ribonucleic acid
- hpRNA hairpin ribonucleic acid
- UTR untranslated region
- WCR western corn rootworm (*Diabrotica virgifera virgifera* LeConte)
- NCR northern corn rootworm (*Diabrotica barberi* Smith and Lawrence)
- MCR Mexican corn rootworm (*Diabrotica virgifera zeae* Krysan and Smith)
- PCR Polymerase chain reaction
- RISC RNA-induced Silencing Complex
- SCR southern corn rootworm (*Diabrotica undecimpunctata howardi* Barber)

III. Terms

In the description and tables which follow, a number of terms are used. In order to provide a clear and consistent understanding of the specification and claims, including the scope to be given such terms, the following definitions are provided:

Coleopteran pest: As used herein, the term "coleopteran pest" refers to insects of the genus *Diabrotica* that feed upon corn and other true grasses. In particular examples, a coleopteran pest is selected from the list comprising *D. v. virgifera* LeConte (WCR); *D. barberi* Smith and Lawrence (NCR); *D. u. howardi* (SCR); *D. v. zeae* (MCR); *D. balteata* LeConte; *D. u. tenella*; and *D. u. undecimpunctata* Mannerheim.

Contact (with an organism): As used herein, the term "contact with" or "uptake by" an organism (e.g., a coleopteran pest), with regard to a nucleic acid molecule, includes internalization of the nucleic acid molecule into the organism, for example and without limitation: ingestion of the molecule by the organism (e.g., by feeding); contacting the organism with a composition comprising the nucleic acid molecule; and soaking of organisms with a solution comprising the nucleic acid molecule.

Contig: As used herein the term "contig" refers to a DNA sequence that is reconstructed from a set of overlapping DNA segments derived from a single genetic source.

Corn plant: As used herein, the term "corn plant" refers to a plant of the species, *Zea mays* (maize).

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Genetic material: As used herein, the term "genetic material" includes all genes, and nucleic acid molecules, such as DNA and RNA.

Inhibition: As used herein, the term "inhibition," when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is approximately eliminated. "Specific inhibition" refers to the inhibition of a target coding sequence without consequently affecting expression of other coding sequences (e.g., genes) in the cell wherein the specific inhibition is being accomplished.

Isolated: An "isolated" biological component (such as a nucleic acid or protein) has been substantially separated, produced apart from, or purified away from other biological components in the cell of the organism in which the component naturally occurs, i.e., other chromosomal and extra-chromosomal DNA and RNA, and proteins. Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of DNA and RNA (reverse transcribed into a cDNA) sequences. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

Genome: As used herein, the term "genome" refers to chromosomal DNA found within the nucleus of a cell, and also refers to organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell. The term "genome" as it applies to bacteria refers to both the chromosome and plasmids within the bacterial cell. In some embodiments of the invention, a DNA molecule may be introduced into a bacterium such that the DNA molecule is integrated into the genome of the bacterium. In these and further embodiments, the DNA molecule may be either chromosomally-integrated or located as or in a stable plasmid.

Sequence identity: The term "sequence identity" or "identity," as used herein in the context of two nucleic acid or polypeptide sequences, refers to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity. A sequence that is identical at every position in comparison to a reference sequence is said to be 100% identical to the reference sequence, and vice-versa.

Methods for aligning sequences for comparison are well-known in the art. Various programs and alignment algorithms are described in, for example: Smith and Waterman (1981) Adv. Appl. Math. 2:482; Needleman and Wunsch (1970) J.

Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default BLOSUM62 matrix set to default parameters. Nucleic acid sequences with even greater similarity to the reference sequences will show increasing percentage identity when assessed by this method.

Specifically hybridizable/Specifically complementary: As used herein, the terms "specifically hybridizable" and "specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times and the compositions of wash buffers also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2nd ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology—Hybridization with Nucleic Acid Probes*, Part I, Chapter 2, Elsevier, N.Y., 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 80% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5×SSC buffer at 65° C. for 20 minutes each.

Moderate Stringency condition (detects sequences that share at least 20% sequence identity): Hybridization in 5×-6× SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a contiguous nucleic acid sequence, refers to contiguous nucleotide sequences that hybridize under stringent conditions to the reference nucleic acid sequence. For example, nucleic acid sequences that are substantially homologous to a reference nucleic acid sequence of any of SEQ ID NOs:1-7 are those nucleic acid sequences that hybridize under stringent conditions (e.g., the Moderate Stringency conditions set forth, supra) to the reference nucleic acid sequence of any of SEQ ID NOs:1-7. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most cell or tissue types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:0421).

Exemplary constitutive promoters include, but are not limited to: Promoters from plant viruses, such as the $^{35}$S promoter from cauliflower mosaic virus (CaMV); promoters from rice actin genes; ubiquitin promoters; pEMU; MAS; maize H3 histone promoter; and the ALS promoter, Xba1/NcoI fragment 5' to the *Brassica napus* ALS3 structural gene (or a nucleotide sequence similarity to said Xba1/NcoI fragment) (International PCT Publication No. WO 96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: A root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Transformation: As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Felgner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous nucleic acid sequence. In some examples, a transgene may be a sequence that encodes one or both strand(s) of a dsRNA molecule that comprises a nucleotide sequence that is complementary to a nucleic acid molecule found in a coleopteran pest. In further examples, a transgene may be an antisense nucleic acid sequence, wherein expression of the antisense nucleic acid sequence inhibits expression of a target nucleic acid sequence. In still further examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences operably linked to a coding sequence of the transgene (e.g., a promoter).

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense sequences, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Yield: A stabilized yield of about 100% or greater relative to the yield of check varieties in the same growing location growing at the same time and under the same conditions. In particular embodiments, "improved yield" or "improving yield" means a cultivar having a stabilized yield of 105% to 115% or greater relative to the yield of check varieties in the same growing location containing significant densities of coleopteran pests that are injurious to that crop growing at the same time and under the same conditions.

Unless specifically indicated or implied, the terms "a," "an," and "the" signify "at least one" as used herein.

Unless otherwise specifically explained, all technical and scientific terms used herein have the same meaning as commonly understood by those of ordinary skill in the art to which this disclosure belongs. Definitions of common terms in molecular biology can be found in, for example, Lewin B., *Genes V*, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers R. A. (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

IV. Nucleic Acid Molecules Comprising a Coleopteran Pest Sequence

A. Overview

Described herein are nucleic acid molecules useful for the control of coleopteran pests. Described nucleic acid molecules include target sequences (e.g., native genes, and non-coding sequences), dsRNAs, siRNAs, hpRNAs, and miRNAs. For example, dsRNA, siRNA, miRNA and/or hpRNA molecules are described in some embodiments that may be specifically complementary to all or part of one or more native nucleic acid sequences in a coleopteran pest. In these and further embodiments, the native nucleic acid sequence(s) may be one or more target gene(s), the product of which may be, for example and without limitation: involved in a metabolic process; involved in a reproductive process; or involved in larval development. Nucleic acid molecules described herein, when introduced into a cell comprising at least one native nucleic acid sequence(s) to which the nucleic acid molecules are specifically complementary, may initiate RNAi in the cell, and consequently reduce or eliminate expression of the native nucleic acid sequence(s). In some examples, reduction or elimination of the expression of a target gene by a nucleic acid molecule comprising a sequence specifically complementary thereto may be lethal in coleopteran pests, or result in reduced growth and/or reproduction.

In some embodiments, at least one target gene in a coleopteran pest may be selected, wherein the target gene comprises a nucleotide sequence selected from the list comprising D_vir_c47185_Caf1 180 (SEQ ID NO:1); D_vir_c1229_VatpaseC (SEQ ID NO:2); D_vir_c1319_VatpaseH (SEQ ID NO:3); and Contig_01_Rho1_1-191_CDC42 (SEQ ID NO:4). In particular examples, a target gene in a coleopteran pest is selected, wherein the target gene encodes a Rho1 small GTP-binding protein and comprises SEQ ID NO:4.

In some embodiments, a target gene may be a nucleic acid molecule comprising a nucleotide sequence that encodes a polypeptide comprising a contiguous amino acid sequence that is at least 85% identical (e.g., about 90%, about 95%, about 96%, about 97%, about 98%, about 99%, about 100%, or 100% identical) to the amino acid sequence of the protein product of one of D_vir_c47185_Caf1 180 (SEQ ID NO:1); D_vir_c1229_VatpaseC (SEQ ID NO:2); D_vir_c1319_VatpaseH (SEQ ID NO:3); and Contig_01_Rho1_1-191_CDC42 (SEQ ID NO:4). A target gene may be any nucleic acid sequence in a coleopteran pest, the post-transcriptional inhibition of which has a deleterious effect on the coleopteran pest, or provides a protective benefit against the coleopteran pest to a plant. In particular examples, a target gene is a nucleic acid molecule comprising a nucleotide sequence that encodes a Rho1 small GTP-binding protein comprising a contiguous amino acid sequence that is at least 85% identical, about 90% identical, about 95% identical, about 96% identical, about 97% identical, about 98% identical, about 99% identical, about 100% identical, or 100% identical to the amino acid sequence of the protein product of SEQ ID NO:4.

Provided according to the invention are nucleotide sequences, the expression of which results in an RNA molecule comprising a nucleotide sequence that is specifically complementary to all or part of a native RNA molecule that is encoded by a coding sequence in a coleopteran pest. In some embodiments, after ingestion of the expressed RNA molecule by a coleopteran pest, down-regulation of the coding sequence in cells of the coleopteran pest may be obtained. In particular embodiments, down-regulation of the coding sequence in cells of the coleopteran pest may result in a deleterious effect on the growth, viability, proliferation, and/or reproduction of the coleopteran pest.

In some embodiments, target sequences include transcribed non-coding RNA sequences, such as 5'UTRs; 3'UTRs; spliced leader sequences; intron sequences; outron sequences (e.g., 5'UTR RNA subsequently modified in trans splicing); donatron sequences (e.g., non-coding RNA required to provide donor sequences for trans splicing); and other non-coding transcribed RNA of target coleopteran pest genes. Such sequences may be derived from both mono-cistronic and poly-cistronic genes.

Thus, also described herein in connection with some embodiments are iRNA molecules (e.g., dsRNAs, siRNAs, miRNAs and hpRNAs) that comprise at least one nucleotide sequence that is specifically complementary to all or part of a target sequence in a coleopteran pest. In some embodiments an iRNA molecule may comprise nucleotide sequence(s) that are complementary to all or part of a plurality of target sequences; for example, 2, 3, 4, 5, 6, 7, 8, 9, 10, or more target sequences. In particular embodiments, an iRNA molecule may be produced in vitro, or in vivo by a genetically-modified organism, such as a plant or bacterium. Also disclosed are cDNA sequences that may be used for the production of dsRNA molecules, siRNA molecules, miRNA and/or hpRNA molecules that are specifically complementary to all or part of a target sequence in a coleopteran pest. Further described are recombinant DNA constructs for use in achieving stable transformation of particular host targets. Transformed host targets may express effective levels of dsRNA, siRNA, miRNA and/or hpRNA molecules from the recombinant DNA constructs. Therefore, also described is a plant transformation vector comprising at least one nucleotide sequence operably linked to a heterologous promoter functional in a plant cell, wherein expression of the nucleotide sequence(s) results in an RNA molecule comprising a nucleotide sequence that is specifically complementary to all or part of a target sequence in a coleopteran pest.

In some embodiments, nucleic acid molecules useful for the control of coleopteran pests may include: the native nucleic acid sequence isolated from *Diabrotica*, D Contig_01_Rho1_1-191_CDC42 (SEQ ID NO:4); nucleotide sequences that when expressed result in a RNA molecule comprising a nucleotide sequence that is specifically complementary to a native RNA molecule that is encoded by Contig_01_Rho1_1-191_CDC42 (SEQ ID NO:4); iRNA molecules (e.g., dsRNAs, siRNAs, miRNAs and hpRNAs) that comprise at least one nucleotide sequence that is specifically complementary to Contig_01_Rho1_1-191_CDC42 (SEQ ID NO:4); cDNA sequences that may be used for the production of dsRNA molecules, siRNA molecules, miRNA and/or hpRNA molecules that are specifically complementary to Contig_01_Rho1_1-191_CDC42 (SEQ ID NO:4); and recombinant DNA constructs for use in achieving stable transformation of particular host targets, wherein a transformed host target comprises one or more of the foregoing nucleic acid molecules.

In these and further embodiments, nucleic acid molecules useful for the control of coleopteran pests may include: a fragment of a *Diabrotica* Rho1 small GTP-binding protein comprising all or part of any of SEQ ID NOs:88-90, 137, and 138; nucleotide sequences that when expressed result in a RNA molecule comprising a nucleotide sequence that is specifically complementary to a native *Diabrotica* RNA molecule comprising all or part of any of SEQ ID NOs:88-90, 137, and 138; iRNA molecules (e.g., dsRNAs, siRNAs, miRNAs and hpRNAs) that comprise at least one nucleotide sequence that is specifically complementary to all or part of any of SEQ ID NOs:88-90, 137, and 138; cDNA sequences that may be used for the production of dsRNA molecules, siRNA molecules, miRNA and/or hpRNA molecules that are specifically complementary to all or part of any of SEQ ID NOs:88-90, 137, and 138; and recombinant DNA constructs for use in achieving stable transformation of particular host targets, wherein a transformed host target comprises one or more of the foregoing nucleic acid molecules.

In these and further embodiments, additional nucleic acid molecules useful for the control of coleopteran pests may include: D_vir_c47185_Caf1 180 (SEQ ID NO:1); D_vir_c1229_VatpaseC (C subunit of vacuolar ATPase) (SEQ ID NO:2); and D_vir_c1319_VatpaseH (H subunit of vacuolar ATPase) (SEQ ID NO:3); nucleotide sequences that when expressed result in an RNA molecule comprising a nucleotide sequence that is specifically complementary to a native RNA molecule that is encoded by D_vir_c47185_Caf1 180 (SEQ ID NO:1); D_vir_c1229_VatpaseC (SEQ ID NO:2); or D_vir_c1319_VatpaseH (SEQ ID NO:3); iRNA molecules (e.g., dsRNAs, siRNAs, miRNAs and hpRNAs) that comprise at least one nucleotide sequence that is specifically complementary to D_vir_c47185_Caf1 180 (SEQ ID NO:1); D_vir_c1229_VatpaseC (SEQ ID NO:2); or D_vir_c1319_VatpaseH (SEQ ID NO:3); cDNA sequences that may be used for the production of dsRNA molecules, siRNA molecules, miRNA and/or hpRNA molecules that are specifically complementary to D_vir_c47185_Caf1 180 (SEQ ID NO:1); D_vir_c1229_VatpaseC (SEQ ID NO:2); or D_vir_c1319_VatpaseH (SEQ ID NO:3); and recombinant DNA constructs for use in achieving stable transformation of particular host targets, wherein a transformed host target comprises one or more of the foregoing nucleic acid molecules.

B. Nucleic Acid Molecules

The present invention provides, inter alia, iRNA (e.g., dsRNA, siRNA, miRNA and hpRNA) molecules that inhibit target gene expression in a cell, tissue, or organ of a coleopteran pest; and DNA molecules capable of being expressed as an iRNA molecule in a cell or microorganism to inhibit target gene expression in a cell, tissue, or organ of a coleopteran pest.

Some embodiments of the invention provide an isolated nucleic acid molecule comprising at least one (e.g., one, two, three, or more) nucleotide sequence(s) selected from the group consisting of SEQ ID NO:4; the complement of SEQ ID NO:4; SEQ ID NO:87; the complement of SEQ ID NO:87; SEQ ID NO:88; the complement of SEQ ID NO:88; SEQ ID NO:89; the complement of SEQ ID NO:89; SEQ ID NO:90; the complement of SEQ ID NO:90; SEQ ID NO:137; the complement of SEQ ID NO:137; SEQ ID NO:138; the complement of SEQ ID NO:138; a fragment of at least 19 contiguous nucleotides comprising all or part of any of SEQ ID NOs:88-90, 137, and 138; the complement of a fragment of at least 19 contiguous nucleotides comprising all or part of any of SEQ ID NOs: 88-90, 137, and 138; a native coding sequence of a *Diabrotica* organism (e.g., WCR) comprising any of SEQ ID NOs:4, 87-90, 137, and 138; the complement of a native coding sequence of a *Diabrotica* organism comprising any of SEQ ID NOs:4, 87-90, 137, and 138; a native non-coding sequence of a *Diabrotica* organism that is transcribed into a native RNA molecule comprising any of SEQ ID NOs:4, 87-90, 137, and 138; the complement of a native non-coding sequence of a *Diabrotica* organism that is transcribed into a native RNA molecule comprising any of SEQ ID NOs:4, 87-90, 137, and 138; a fragment of at least 19 contiguous nucleotides of a native coding sequence of a *Diabrotica* organism comprising all or part of any of SEQ ID NOs:88-90, 137, and 138; the complement of a fragment of at least 19 contiguous nucleotides of a native coding sequence of a *Diabrotica* organism comprising all or part of any of SEQ ID NOs: 88-90, 137, and 138; a fragment of at least 19 contiguous nucleotides of a native non-coding sequence of a *Diabrotica* organism that is transcribed into a native RNA molecule comprising all or part of any of SEQ ID NOs: 88-90, 137, and 138; and the complement of a fragment of at least 19 contiguous nucleotides of a native non-coding sequence of a *Diabrotica* organism that is transcribed into a native RNA molecule comprising all or part of any of SEQ ID NOs: 88-90, 137, and 138. In particular embodiments, contact with or uptake by a coleopteran pest of the isolated nucleic acid sequence inhibits the growth, development, reproduction and/or feeding of the coleopteran pest.

In some embodiments, an isolated nucleic acid molecule of the invention may further comprise at least one (e.g., one, two, three, or more) nucleotide sequence(s) selected from the group consisting of: all or part of SEQ ID NO:1; all or part of the complement of SEQ ID NO:1; SEQ ID NO:2; the complement of SEQ ID NO:2; SEQ ID NO:3; the complement of SEQ ID NO:3; a fragment of at least 19 contiguous nucleotides of any of SEQ ID NOs:1-3; the complement of a fragment of at least 19 contiguous nucleotides of any of SEQ ID NOs:1-3; a native coding sequence of a *Diabrotica* organism (e.g., WCR) comprising any of SEQ ID NOs:1-3; the complement of a native coding sequence of a *Diabrotica* organism comprising any of SEQ ID NOs:1-3; a native non-coding sequence of a *Diabrotica* organism that is transcribed into a native RNA molecule comprising any of SEQ ID NOs: 1-3; the complement of a native non-coding sequence of a *Diabrotica* organism that is transcribed into a native RNA molecule comprising any of SEQ ID NOs:1-3; a fragment of at least 19 contiguous nucleotides of a native coding sequence of a *Diabrotica* organism comprising any of SEQ ID NOs:1-3; the complement of a fragment of at least 19 contiguous nucleotides of a native coding sequence of a *Diabrotica* organism comprising any of SEQ ID NOs:1-3; a fragment of at least 19 contiguous nucleotides of a native non-coding sequence of a *Diabrotica* organism that is transcribed into a native RNA molecule comprising any of SEQ ID NOs:1-3; and the complement of a fragment of at least 19 contiguous nucleotides of a native non-coding sequence of a *Diabrotica* organism that is transcribed into a native RNA molecule comprising any of SEQ ID NOs:1-3. In particular embodiments, contact with or uptake by a coleopteran pest of the isolated nucleic acid sequence inhibits the growth, development, reproduction and/or feeding of the coleopteran pest.

In some embodiments, a nucleic acid molecule of the invention may comprise at least one (e.g., one, two, three, or more) DNA sequence(s) capable of being expressed as an iRNA molecule in a cell or microorganism to inhibit target gene expression in a cell, tissue, or organ of a coleopteran pest. Such DNA sequence(s) may be operably linked to a promoter sequence that functions in a cell comprising the DNA molecule to initiate or enhance the transcription of the encoded dsRNA molecule(s). In one embodiment, the at least one (e.g., one, two, three, or more) DNA sequence(s) may be derived from SEQ ID NO:4. Derivatives of SEQ ID NO:4 include fragments of SEQ ID NO:4. In some embodiments, a fragment of SEQ ID NO:4 may comprise, for example, at least about 19 contiguous nucleotides of any of SEQ ID NOs:88-90, 137, and 138, or a complement of any of the foregoing. Thus, a fragment of SEQ ID NO:4 may comprise, for example, 19, 20, 21, 22, 23, 24, 25, 26, 27, 28, 29, or 30 contiguous nucleotides of SEQ ID NO:4, or a complement thereof, and comprise all or part of any of SEQ ID NOs:88-90, 137, and 138, or a complement thereof. In these and further embodiments, a fragment of SEQ ID NO:4 may comprise, for example, more than about 19 contiguous nucleotides of SEQ ID NO:4, or a complement thereof. Thus, a fragment of SEQ ID NO:4 may comprise, for example, 19, 20, 21, about 25 (e.g., 22, 23, 24, 25, 26, 27, 28, and 29), about 30, about 40 (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200, or more contiguous nucleotides of one or more of SEQ ID NOs:88-90, 137, and 138, or a complement thereof.

In particular embodiments, at least one DNA sequence(s) capable of being expressed as an iRNA molecule in a cell or microorganism to inhibit target gene expression in a cell, tissue, or organ of a coleopteran pest may further comprise DNA sequence(s) that are derived from a nucleotide sequence selected from the group comprising SEQ ID NOs:1-3. Derivatives of a nucleotide sequence selected from the group comprising SEQ ID NOs:1-3 include fragments of one or more of SEQ ID NOs:1-3. In some embodiments, a fragment of one or more of SEQ ID NOs:1-3 may comprise, for example, at least about 19 contiguous nucleotides of any of SEQ ID NOs:1-3, or a complement thereof. Thus, a fragment of one or more of SEQ ID NOs:1-3 may comprise, for example, 19, 20, 21, 22, 23, 24, 25, 26, 27, 28, 29, or 30 contiguous nucleotides of any of the sequences in SEQ ID NOs:1-3, or a complement thereof. In these and further embodiments, a fragment of one or more of SEQ ID NOs:1-3 may comprise, for example, more than about 19 contiguous nucleotides of any of SEQ ID NOs:1-3, or a complement thereof. Thus, a fragment of one or more of SEQ ID NOs:1-3 may comprise, for example, 19, 20, 21, about 25 (e.g., 22, 23, 24, 25, 26, 27, 28, and 29), about 30, about 40 (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200, or more contiguous nucleotides of any of SEQ ID NOs:1-3, or a complement thereof.

Some embodiments comprise introducing partial- or fully-stabilized dsRNA molecules into a coleopteran pest to inhibit expression of a target gene in a cell, tissue, or organ of the coleopteran pest. When expressed as an iRNA molecule (e.g., dsRNA, siRNA, miRNA, and hpRNA) and taken up by a coleopteran pest, nucleic acid sequences comprising one or more fragments of any of SEQ ID NOs:1-4 may cause one or more of death, growth inhibition, change in sex ratio, reduction in brood size, cessation of infection, and/or cessation of feeding by a coleopteran pest. For example, in some embodiments, a dsRNA molecule comprising a nucleotide sequence including about 19 to about 300 nucleotides that are substantially homologous to a coleopteran pest target gene sequence and comprising SEQ ID NO:4 or all or part of any of SEQ ID NOs:88-90, 137, and 138 is provided. Specific examples of dsRNA molecules comprising at least one nucleotide sequence that is substantially homologous to a coleopteran pest target gene sequence and comprising SEQ ID NO:4 or all or part of any of SEQ ID NOs:88-90, 137, and 138 may be, without limitation, at least 19, 20, 21, about 25 (e.g., 22, 23, 24, 25, 26, 27, 28, and 29), about 30, about 40 (e.g., 35, 36, 37, 38, 39, 40, 41, 42, 43, 44, and 45), about 50, about 60, about 70, about 80, about 90, about 100, about 110, about 120, about 130, about 140, about 150, about 160, about 170, about 180, about 190, about 200, or more nucleotides in length. Such dsRNA molecules may further comprise one or more fragments of SEQ ID NOs:1-3. Expression of such a dsRNA molecule may, for example, lead to mortality in a coleopteran pest that takes up the dsRNA molecule.

In certain embodiments, dsRNA molecules provided by the invention comprise nucleotide sequences complementary to a target gene comprising SEQ ID NO:4 and/or nucleotide sequences complementary to all or part of any of SEQ ID NOs:88-90, the inhibition of which target gene in a coleopteran pest results in the reduction or removal of a protein or nucleotide sequence agent that is essential for the coleopteran pest's growth, development, or other biological function. A selected nucleotide sequence may exhibit from about 80% to about 100% sequence identity to SEQ ID NO:4; a contiguous fragment of the nucleotide sequence set forth in SEQ ID NO:4 comprising all or part of any of SEQ ID NOs:88-90, 137, and 138; or the complement of any of the foregoing. For example, a selected nucleotide sequence may exhibit about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; or about 100% sequence identity to SEQ ID NO:4; a contiguous fragment of the nucleotide sequence set forth in SEQ ID NO:4 comprising all or part of any of SEQ ID NOs:88-90, 137, and 138; or the complement of any of the foregoing. In particular embodiments, a dsRNA molecule provided by the invention may further comprise one or more nucleotide sequences complementary to a target gene comprising one of SEQ ID NOs:1-3, the inhibition of which target gene in a coleopteran pest results in the reduction or removal of a protein or nucleotide sequence agent that is essential for the coleopteran pest's growth, development, or other biological function.

In some embodiments, a DNA molecule capable of being expressed as an iRNA molecule in a cell or microorganism to inhibit target gene expression may comprise a single nucleotide sequence that is specifically complementary to all or part of a native nucleic acid sequence found in one or more target coleopteran pest species, or the DNA molecule can be constructed as a chimera from a plurality of such specifically complementary sequences.

In some embodiments, a nucleic acid molecule may comprise a first and a second nucleotide sequence separated by a "spacer sequence." A spacer sequence may be a region comprising any sequence of nucleotides that facilitates secondary structure formation between the first and second nucleotide sequences, where this is desired. In one embodiment, the spacer sequence is part of a sense or antisense coding sequence for mRNA. The spacer sequence may alternatively comprise any combination of nucleotides or homologues thereof that are capable of being linked covalently to a nucleic acid molecule.

For example, in some embodiments, the DNA molecule may comprise a nucleotide sequence coding for one or more different RNA molecules, wherein each of the different RNA molecules comprises a first nucleotide sequence and a second nucleotide sequence, wherein the first and second nucleotide sequences are complementary to each other. The first and second nucleotide sequences may be connected within an RNA molecule by a spacer sequence. The spacer sequence may constitute part of the first nucleotide sequence or the second nucleotide sequence. Expression of an RNA molecule comprising the first and second nucleotide sequences may lead to the formation of a dsRNA molecule of the present invention, by specific hybridization of the first and second nucleotide sequences. The first nucleotide sequence or the second nucleotide sequence may be substantially identical to a nucleic acid sequence native to a coleopteran pest (e.g., a target gene, or transcribed non-coding sequence), a derivative thereof, or a complementary sequence thereto.

dsRNA nucleic acid molecules comprise double strands of polymerized ribonucleotide sequences, and may include modifications to either the phosphate-sugar backbone or the nucleoside. Modifications in RNA structure may be tailored to allow specific inhibition. In one embodiment, dsRNA molecules may be modified through a ubiquitous enzymatic process so that siRNA molecules may be generated. This enzymatic process may utilize an RNAse III enzyme, such as DICER in eukaryotes, either in vitro or in vivo. See Elbashir et al. (2001) Nature 411:494-8; and Hamilton and Baulcombe (1999) Science 286(5441):950-2. DICER or functionally-equivalent RNAse III enzymes cleave larger dsRNA strands and/or hpRNA molecules into smaller oligonucleotides (e.g., siRNAs), each of which is about 19-25 nucleotides in length. The siRNA molecules produced by these enzymes have 2 to 3 nucleotide 3' overhangs, and 5' phosphate and 3' hydroxyl termini. The siRNA molecules generated by RNAse III enzymes are unwound and separated into single-stranded RNA in the cell. The siRNA molecules then specifically hybridize with RNA sequences transcribed from a target gene, and both RNA molecules are subsequently degraded by an inherent cellular RNA-degrading mechanism. This process may result in the effective degradation or removal of the RNA sequence encoded by the target gene in the target organism. The outcome is the post-transcriptional silencing of the targeted gene. In some embodiments, siRNA molecules produced by endogenous RNAse III enzymes from heterologous nucleic acid molecules may efficiently mediate the down-regulation of target genes in coleopteran pests.

In some embodiments, a nucleic acid molecule of the invention may include at least one non-naturally occurring nucleotide sequence that can be transcribed into a single-stranded RNA molecule capable of forming a dsRNA molecule in vivo through intermolecular hybridization. Such dsRNA sequences typically self-assemble, and can be provided in the nutrition source of a coleopteran pest to achieve the post-transcriptional inhibition of a target gene. In these and further embodiments, a nucleic acid molecule of the invention may comprise two different non-naturally occurring nucleotide sequences, each of which is specifically complementary to a different target gene in a coleopteran pest. When such a nucleic acid molecule is provided as a dsRNA molecule to a coleopteran pest, the dsRNA molecule inhibits the expression of at least two different target genes in the coleopteran pest.

C. Obtaining Nucleic Acid Molecules

A variety of native sequences in coleopteran pests may be used as target sequences for the design of nucleic acid molecules of the invention, such as iRNAs and DNA molecules encoding iRNAs. Selection of native sequences is not, however, a straight-forward process. Only a small number of native sequences in the coleopteran pest will be effective targets. For example, it cannot be predicted with certainty whether a particular native sequence can be effectively down-regulated by nucleic acid molecules of the invention, or whether down-regulation of a particular native sequence will have a detrimental effect on the growth, viability, proliferation, and/or reproduction of the coleopteran pest. The vast majority of native coleopteran pest sequences, such as ESTs isolated therefrom (for example, as listed in U.S. Pat. No. 7,612,194 and U.S. Pat. No. 7,943,819), do not have a detrimental effect on the growth, viability, proliferation, and/or reproduction of the coleopteran pest, such as WCR or NCR. Neither is it predictable which of the native sequences which may have a detrimental effect on a coleopteran pest are able to be used in recombinant techniques for expressing nucleic acid molecules complementary to such native sequences in a host plant and providing the detrimental effect on the coleopteran pest upon feeding without causing harm to the host plant.

In some embodiments, nucleic acid molecules of the invention (e.g., dsRNA molecules to be provided in the host plant of a coleopteran pest) are selected to target cDNA sequences encoding proteins or parts of proteins essential for coleopteran pest survival, such as amino acid sequences involved in metabolic or catabolic biochemical pathways, cell division, reproduction, energy metabolism, digestion, parasitism and the like. As described herein, ingestion of compositions by a target organism containing one or more dsRNAs, at least one segment of which is specifically complementary to at least a substantially identical segment of RNA produced in the cells of the target pathogen, can result in the death or other inhibition of the target. A nucleotide sequence, either DNA or RNA, derived from a coleopteran pest can be used to construct plant cells resistant to infestation by the coleopteran pests. The host plant of the coleopteran pest (e.g., Z. mays or G. max), for example, can be transformed to contain one or more of the nucleotide sequences derived from the coleopteran pest as provided herein. The nucleotide sequence transformed into the host may encode one or more RNAs that form into a dsRNA sequence in the cells or biological fluids within the transformed host, thus making the dsRNA available if/when the coleopteran pest forms a nutritional relationship with the transgenic host. This may result in the suppression of expression of one or more genes in the cells of the coleopteran pest, and ultimately death or inhibition of its growth or development.

Thus, in some embodiments, a gene is targeted that is essentially involved in the growth, development and reproduction of a coleopteran pest. Other target genes for use in the present invention may include, for example, those that play important roles in coleopteran pest viability, movement, migration, growth, development, infectivity, establishment of feeding sites and reproduction. A target gene may therefore be a housekeeping gene or a transcription factor. Additionally, a native coleopteran pest nucleotide sequence for use in the present invention may also be derived from a homolog (e.g., an ortholog), of a plant, viral, bacterial or insect gene, the function of which is known to those of skill in the art, and the nucleotide sequence of which is specifically hybridizable with a target gene in the genome of the target coleopteran pest. Methods of identifying a homolog of a gene with a known nucleotide sequence by hybridization are known to those of skill in the art.

In some embodiments, the invention provides methods for obtaining a nucleic acid molecule comprising a nucleotide sequence for producing an iRNA (e.g., dsRNA, siRNA, miRNA, and hpRNA) molecule. One such embodiment comprises: (a) analyzing one or more target gene(s) for their expression, function, and phenotype upon dsRNA-mediated gene suppression in a coleopteran pest; (b) probing a cDNA or gDNA library with a probe comprising all or a portion of a nucleotide sequence or a homolog thereof from a targeted coleopteran pest that displays an altered (e.g., reduced) growth or development phenotype in a dsRNA-mediated suppression analysis; (c) identifying a DNA clone that specifically hybridizes with the probe; (d) isolating the DNA clone identified in step (b); (e) sequencing the cDNA or gDNA fragment that comprises the clone isolated in step (d), wherein the sequenced nucleic acid molecule transcribes all or a substantial portion of the RNA sequence or a homolog thereof; and (f) chemically synthesizing all or a substantial portion of a gene sequence, or a siRNA or miRNA or hpRNA or mRNA or dsRNA.

In further embodiments, a method for obtaining a nucleic acid fragment comprising a nucleotide sequence for producing a substantial portion of an iRNA (e.g., dsRNA, siRNA, miRNA, and hpRNA) molecule includes: (a) synthesizing first and second oligonucleotide primers specifically complementary to a portion of a native nucleotide sequence from a targeted coleopteran pest; and (b) amplifying a cDNA or gDNA insert present in a cloning vector using the first and second oligonucleotide primers of step (a), wherein the amplified nucleic acid molecule transcribes a substantial portion of a siRNA or miRNA or hpRNA or mRNA or dsRNA molecule.

Nucleic acids of the invention can be isolated, amplified, or produced by a number of approaches. For example, an iRNA (e.g., dsRNA, siRNA, miRNA, and hpRNA) molecule may be obtained by PCR amplification of a target nucleic acid sequence (e.g., a target gene or a target transcribed non-coding sequence) derived from a gDNA or cDNA library, or portions thereof. DNA or RNA may be extracted from a target organism, and nucleic acid libraries may be prepared therefrom using methods known to those ordinarily skilled in the art and. gDNA or cDNA libraries generated from a target organism may be used for PCR amplification and sequencing of target genes. A confirmed PCR product may be used as a template for in vitro transcription to generate sense and antisense RNA with minimal promoters. Alternatively, nucleic acid molecules may be synthesized by any of a number of techniques (See, e.g., Ozaki et al. (1992) Nucleic Acids Research, 20: 5205-5214; and Agrawal et al. (1990) Nucleic Acids Research, 18: 5419-5423), including use of an automated DNA synthesizer (for example, a P.E. Biosystems, Inc. (Foster City, Calif.) model 392 or 394 DNA/RNA Synthesizer), using standard chemistries, such as phosphoramidite chemistry. See, e.g., Beaucage et al. (1992) Tetrahedron, 48: 2223-2311; U.S. Pat. Nos. 4,980,460, 4,725,677, 4,415,732, 4,458,066, and 4,973,679. Alternative chemistries resulting in non-natural backbone groups, such as phosphorothioate, phosphoramidate, and the like, can also be employed.

A RNA, dsRNA, siRNA, miRNA, or hpRNA molecule of the present invention may be produced chemically or enzymatically by one skilled in the art through manual or automated reactions, or in vivo in a cell comprising a nucleic acid molecule comprising a sequence encoding the RNA, dsRNA, siRNA, miRNA, or hpRNA molecule. RNA may also be produced by partial or total organic synthesis—any modified ribonucleotide can be introduced by in vitro enzymatic or organic synthesis. An RNA molecule may be synthesized by a cellular RNA polymerase or a bacteriophage RNA polymerase (e.g., T3 RNA polymerase, T7 RNA polymerase, and SP6 RNA polymerase). Expression constructs useful for the cloning and expression of nucleotide sequences are known in the art. See, e.g., International PCT Publication No. WO 97/32016; and U.S. Pat. Nos. 5,593,874, 5,698,425, 5,712,135, 5,789,214, and 5,804,693. RNA molecules that are synthesized chemically or by in vitro enzymatic synthesis may be purified prior to introduction into a cell. For example, RNA molecules can be purified from a mixture by extraction with a solvent or resin, precipitation, electrophoresis, chromatography, or a combination thereof. Alternatively, RNA molecules that are synthesized chemically or by in vitro enzymatic synthesis may be used with no or a minimum of purification, for example, to avoid losses due to sample processing. The RNA molecules may be dried for storage or dissolved in an aqueous solution. The solution may contain buffers or salts to promote annealing, and/or stabilization of dsRNA molecule duplex strands.

In embodiments, a dsRNA molecule may be formed by a single self-complementary RNA strand or from two complementary RNA strands. dsRNA molecules may be synthesized either in vivo or in vitro. An endogenous RNA polymerase of the cell may mediate transcription of the one or two RNA strands in vivo, or cloned RNA polymerase may be used to mediate transcription in vivo or in vitro. Post-transcriptional inhibition of a target gene in a coleopteran pest may be host-targeted by specific transcription in an organ, tissue, or cell type of the host (e.g., by using a tissue-specific promoter); stimulation of an environmental condition in the host (e.g., by using an inducible promoter that is responsive to infection, stress, temperature, and/or chemical inducers); and/or engineering transcription at a developmental stage or age of the host (e.g., by using a developmental stage-specific promoter). RNA strands that form a dsRNA molecule, whether transcribed in vitro or in vivo, may or may not be polyadenylated, and may or may not be capable of being translated into a polypeptide by a cell's translational apparatus.

D. Recombinant Vectors and Host Cell Transformation

In some embodiments, the invention also provides a DNA molecule for introduction into a cell (e.g., a bacterial cell, a yeast cell, or a plant cell), wherein the DNA molecule comprises a nucleotide sequence that, upon expression to RNA and ingestion by a coleopteran pest, achieves suppression of a target gene in a cell, tissue, or organ of the coleopteran pest. Thus, some embodiments provide a recombinant nucleic acid molecule comprising a nucleic acid sequence capable of being expressed as an iRNA (e.g., dsRNA, siRNA, miRNA, and hpRNA) molecule in a plant cell to inhibit target gene expression in a coleopteran pest. In order to initiate or enhance expression, such recombinant nucleic acid molecules may comprise one or more regulatory sequences, which regulatory sequences may be operably linked to the nucleic acid sequence capable of being expressed as an iRNA. Methods to express a gene suppression molecule in plants are known, and may be used to express a nucleotide sequence of the present invention. See, e.g., International PCT Publication No. WO06073727; and U.S. Patent Publication No. 2006/0200878 A1)

In specific embodiments, a recombinant DNA molecule of the invention may comprise a nucleic acid sequence encoding a dsRNA molecule. Such recombinant DNA molecules may encode dsRNA molecules capable of inhibiting the expression of endogenous target gene(s) in a coleopteran pest cell upon ingestion. In many embodiments, a transcribed dsRNA molecule may be provided in a stabilized form; e.g., as a hairpin and stem and loop structure.

In these and further embodiments, one strand of a dsRNA molecule may be formed by transcription from a nucleotide sequence which is substantially homologous to a nucleotide sequence selected from the group consisting of: SEQ ID NO:4; the complement of SEQ ID NO:4; SEQ ID NO:87; the complement of SEQ ID NO:87; SEQ ID NO:88; the complement of SEQ ID NO:88; SEQ ID NO:89; the complement of SEQ ID NO:89; SEQ ID NO:90; the complement of SEQ ID NO:90; SEQ ID NO:137; the complement of SEQ ID NO:137; SEQ ID NO:138; the complement of SEQ ID NO:138; a fragment of at least 19 contiguous nucleotides comprising all or part of any of SEQ ID NOs:88-90, 137, and 138; the complement of a fragment of at least 19 contiguous nucleotides comprising all or part of any of SEQ ID NOs: 88-90, 137, and 138; a native coding sequence of a *Diabrotica* organism (e.g., WCR) comprising any of SEQ ID NOs:4, 87-90, 137, and 138; the complement of a native coding sequence of a *Diabrotica* organism comprising any of SEQ ID NOs: 4, 87-90, 137, and 138; a native non-coding sequence of a *Diabrotica* organism that is transcribed into a native RNA molecule comprising any of SEQ ID NOs: 4, 87-90, 137, and 138; the complement of a native non-coding sequence of a *Diabrotica* organism that is transcribed into a native RNA molecule comprising any of SEQ ID NOs: 4, 87-90, 137, and 138; a fragment of at least 19 contiguous nucleotides of a native coding sequence of a *Diabrotica* organism comprising all or part of any of SEQ ID NOs: 88-90, 137, and 138; the complement of a fragment of at least 19 contiguous nucleotides of a native coding sequence of a *Diabrotica* organism comprising all or part of any of SEQ ID NOs: 88-90, 137, and 138; a fragment of at least 19 contiguous nucleotides of a native non-coding sequence of a *Diabrotica* organism that is transcribed into a native RNA molecule comprising all or part of any of SEQ ID NOs: 88-90, 137, and 138; and the complement of a fragment of at least 19 contiguous nucleotides of a native non-coding sequence of a *Diabrotica* organism that is transcribed into a native RNA molecule comprising all or part of any of SEQ ID NOs: 88-90, 137, and 138.

One strand of a dsRNA molecule may also be formed by transcription from a nucleotide sequence which is substantially homologous to a nucleotide sequence selected from the group consisting of: SEQ ID NO:1; the complement of SEQ ID NO:1; SEQ ID NO:2; the complement of SEQ ID NO:2; SEQ ID NO:3; the complement of SEQ ID NO:3; a fragment of at least 19 contiguous nucleotides of any of SEQ ID NOs: 1-3; the complement of a fragment of at least 19 contiguous nucleotides of any of SEQ ID NOs:1-3; a native coding sequence of a *Diabrotica* organism (e.g., WCR) comprising any of SEQ ID NOs:1-3; the complement of a native coding sequence of a *Diabrotica* organism comprising any of SEQ ID NOs:1-3; a native non-coding sequence of a *Diabrotica* organism that is transcribed into a native RNA molecule comprising any of SEQ ID NOs:1-3; the complement of a native non-coding sequence of a *Diabrotica* organism that is transcribed into a native RNA molecule comprising any of SEQ ID NOs:1-3; a fragment of at least 19 contiguous nucleotides of a native coding sequence of a *Diabrotica* organism comprising any of SEQ ID NOs:1-3; the complement of a fragment of at least 19 contiguous nucleotides of a native coding sequence of a *Diabrotica* organism comprising any of SEQ ID NOs:1-3; a fragment of at least 19 contiguous nucleotides of a native non-coding sequence of a *Diabrotica* organism that is transcribed into a native RNA molecule comprising any of SEQ ID NOs:1-3; and the complement of a fragment of at least 19 contiguous nucleotides of a native non-coding sequence of a *Diabrotica* organism that is transcribed into a native RNA molecule comprising any of SEQ ID NOs:1-3.

In particular embodiments, a recombinant DNA molecule encoding a dsRNA molecule may comprise at least two nucleotide sequences with a coding sequence arranged such that one nucleotide sequence is in a sense orientation, and the other nucleotide sequence is in an antisense orientation, relative to at least one promoter, wherein the sense nucleotide sequence and the antisense nucleotide sequence are linked or connected by a spacer sequence of from about five (~5) to about one thousand (~1000) nucleotides. The spacer sequence may form a loop between the sense and antisense sequences. The sense nucleotide sequence or the antisense nucleotide sequence may be substantially homologous to the nucleotide sequence of a target gene (e.g., a gene comprising one of SEQ ID NOs:1-4) or fragment thereof. In some embodiments, however, a recombinant DNA molecule may encode a dsRNA molecule without a spacer sequence. In embodiments, a sense coding sequence and an antisense coding sequence may be different lengths.

Sequences identified as having a deleterious effect on coleopteran pests or a plant-protective effect with regard to coleopteran pests may be readily incorporated into expressed dsRNA molecules through the creation of appropriate expression cassettes in a recombinant nucleic acid molecule of the invention. For example, such sequences may be expressed as a hairpin with stem and loop structure by taking a first segment corresponding to a target gene sequence (e.g., SEQ ID NO:4 and sequences comprising all or part of one of SEQ ID NOs:88-90); linking this sequence to a second segment spacer region that is not homologous or complementary to the first segment; and linking this to a third segment, wherein at least a portion of the third segment is substantially complementary to the first segment. Such a construct forms a stem and loop structure by hybridization of the first segment with the third segment, wherein the loop structure forms comprising the second segment. See, e.g., U.S. Patent Publication Nos. US 2002/0048814 and US 2003/0018993; and International PCT Publication Nos. WO94/01550 and WO98/05770. A dsRNA molecule may be generated, for example, in the form of a double-stranded structure such as a stem-loop structure (e.g., hairpin), whereby production of siRNA targeted for a native coleopteran pest sequence is enhanced by co-expression of a fragment of the targeted gene, for instance on an additional plant expressible cassette, that leads to enhanced siRNA production, or reduces methylation to prevent transcriptional gene silencing of the dsRNA hairpin promoter.

Embodiments of the invention include introduction of a recombinant nucleic acid molecule of the present invention into a plant (i.e., transformation) to achieve coleopteran pest-inhibitory levels of expression of one or more iRNA molecules. A recombinant DNA molecule may, for example, be a vector, such as a linear or a closed circular plasmid. The vector system may be a single vector or plasmid, or two or more vectors or plasmids that together contain the total DNA to be introduced into the genome of a host. In addition, a vector may be an expression vector. Nucleic acid sequences of the invention can, for example, be suitably inserted into a vector under the control of a suitable promoter that functions in one or more hosts to drive expression of a linked coding sequence or other DNA sequence. Many vectors are available for this purpose, and selection of the appropriate vector will depend mainly on the size of the nucleic acid to be inserted into the vector and the particular host cell to be transformed with the vector. Each vector contains various components depending on its function (e.g., amplification of DNA or expression of DNA) and the particular host cell with which it is compatible.

To impart coleopteran pest resistance to a transgenic plant, a recombinant DNA may, for example, be transcribed into an iRNA molecule (e.g., an RNA molecule that forms a dsRNA molecule) within the tissues or fluids of the recombinant plant. An iRNA molecule may comprise a nucleotide sequence that is substantially homologous and specifically hybridizable to a corresponding transcribed nucleotide sequence within a coleopteran pest that may feed upon the host plant species. The coleopteran pest may contact the iRNA molecule that is transcribed in cells of the transgenic host plant, for example, by ingesting cells or fluids of the transgenic host plant that comprise the iRNA molecule. Thus, expression of a target gene is suppressed by the iRNA molecule within coleopteran pests that infest the transgenic host plant. In some embodiments, suppression of expression of the target gene in the target coleopteran pest may result in the plant being resistant to the pest.

In order to enable delivery of iRNA molecules to a coleopteran pest in a nutritional relationship with a plant cell that has been transformed with a recombinant nucleic acid molecule of the invention, expression (i.e., transcription) of iRNA molecules in the plant cell is required. Thus, a recombinant nucleic acid molecule may comprise a nucleotide sequence of the invention operably linked to one or more regulatory sequences, such as a heterologous promoter sequence that functions in a host cell, such as a bacterial cell wherein the nucleic acid molecule is to be amplified, or a plant cell wherein the nucleic acid molecule is to be expressed.

Promoters suitable for use in nucleic acid molecules of the invention include those that are inducible, viral, synthetic, or constitutive, all of which are well known in the art. Non-limiting examples describing such promoters include U.S. Pat. No. 6,437,217 (maize RS81 promoter); U.S. Pat. No. 5,641,876 (rice actin promoter); U.S. Pat. No. 6,426,446 (maize RS324 promoter); U.S. Pat. No. 6,429,362 (maize PR-1 promoter); U.S. Pat. No. 6,232,526 (maize A3 promoter); U.S. Pat. No. 6,177,611 (constitutive maize promoters); U.S. Pat. Nos. 5,322,938, 5,352,605, 5,359,142, and 5,530,196 (35S promoter); U.S. Pat. No. 6,433,252 (maize L3 oleosin promoter); U.S. Pat. No. 6,429,357 (rice actin 2 promoter, and rice actin 2 intron); U.S. Pat. No. 6,294,714 (light-inducible promoters); U.S. Pat. No. 6,140,078 (salt-inducible promoters); U.S. Pat. No. 6,252,138 (pathogen-inducible promoters); U.S. Pat. No. 6,175,060 (phosphorous deficiency-inducible promoters); U.S. Pat. No. 6,388,170 (bidirectional promoters); U.S. Pat. No. 6,635,806 (gamma-coixin promoter); and U.S. patent application Ser. No. 09/757,089 (maize chloroplast aldolase promoter). Additional promoters include the nopaline synthase (NOS) promoter (Ebert et al. (1987) Proc. Natl. Acad. Sci. USA 84(16):5745-9) and the octopine synthase (OCS) promoter (both of which are carried on tumor-inducing plasmids of *Agrobacterium tumefaciens*); the caulimovirus promoters such as the cauliflower mosaic virus (CaMV) 19S promoter (Lawton et al. (1987) Plant Mol. Biol. 9:315-24); the CaMV $^{35}$S promoter (Odell et al. (1985) Nature 313:810-2; the figwort mosaic virus 35S-promoter (Walker et al. (1987) Proc. Natl. Acad. Sci. USA 84(19): 6624-8); the sucrose synthase promoter (Yang and Russell (1990) Proc. Natl. Acad. Sci. USA 87:4144-8); the R gene complex promoter (Chandler et al. (1989) Plant Cell 1:1175-83); the chlorophyll a/b binding protein gene promoter; CaMV35S (U.S. Pat. Nos. 5,322,938, 5,352,605, 5,359,142, and 5,530,196); FMV35S (U.S. Pat. Nos. 6,051,753, and 5,378,619); a PC1SV promoter (U.S. Pat. No. 5,850,019); the SCP1 promoter (U.S. Pat. No. 6,677,503); and AGRtu.nos promoters (GenBank Accession No. V00087; Depicker et al. (1982) J. Mol. Appl. Genet. 1:561-73; Bevan et al. (1983) Nature 304:184-7).

In particular embodiments, nucleic acid molecules of the invention comprise a tissue-specific promoter, such as a root-specific promoter. Root-specific promoters drive expression of operably-linked sequences exclusively or preferentially in root tissue. Examples of root-specific promoters are known in the art. See, e.g., U.S. Pat. Nos. 5,110,732; 5,459,252 and 5,837,848; and Opperman et al. (1994) Science 263:221-3; and Hirel et al. (1992) Plant Mol. Biol. 20:207-18. In some embodiments, a nucleotide sequence or fragment for coleopteran pest control according to the invention may be cloned between two root-specific promoters, which are operable in a transgenic plant cell and expressed therein to produce RNA molecules in the transgenic plant cell that subsequently may form dsRNA molecules, as described, supra. The iRNA molecules expressed in plant tissues may be ingested by a coleopteran pest so that suppression of target gene expression is achieved.

Additional regulatory sequences that may optionally be operably linked to a nucleic acid molecule of interest include 5' UTRs located between a promoter sequence and a coding sequence that function as a translation leader sequence. The translation leader sequence is present in the fully-processed mRNA, and it may affect processing of the primary transcript, and/or RNA stability. Examples of translation leader sequences include maize and petunia heat shock protein leaders (U.S. Pat. No. 5,362,865), plant virus coat protein leaders, plant rubisco leaders, and others. See, e.g., Turner and Foster (1995) Molecular Biotech. 3(3):225-36. Non-limiting examples of 5' UTRs include GmHsp (U.S. Pat. No. 5,659,122); PhDnaK (U.S. Pat. No. 5,362,865); AtAnt1; TEV (Carrington and Freed (1990) J. Virol. 64:1590-7); and AGRtunos (GenBank Accession No. V00087; and Bevan et al. (1983) Nature 304:184-7).

Additional regulatory sequences that may optionally be operably linked to a nucleic acid molecule of interest also include 3' non-translated sequences, 3' transcription termination regions, or poly-adenylation regions. These are genetic elements located downstream of a nucleotide sequence, and include polynucleotides that provide polyadenylation signal, and/or other regulatory signals capable of affecting transcription or mRNA processing. The polyadenylation signal functions in plants to cause the addition of polyadenylate nucleotides to the 3' end of the mRNA precursor. The polyadenylation sequence can be derived from a variety of plant genes, or from T-DNA genes. A non-limiting example of a 3' transcription termination region is the nopaline synthase 3' region (nos 3'; Fraley et al. (1983) Proc. Natl. Acad. Sci. USA 80:4803-7). An example of the use of different 3' nontranslated regions is provided in Ingelbrecht et al., (1989) Plant Cell 1:671-80. Non-limiting examples of polyadenylation signals include one from a *Pisum sativum* RbcS2 gene (Ps.RbcS2-E9; Coruzzi et al. (1984) EMBO J. 3:1671-9) and AGRtu.nos (GenBank Accession No. E01312).

Some embodiments may include a plant transformation vector that comprises an isolated and purified DNA molecule comprising at least one of the above-described regulatory sequences operatively linked to one or more nucleotide sequences of the present invention. When expressed, the one or more nucleotide sequences result in one or more RNA molecule(s) comprising a nucleotide sequence that is specifically complementary to all or part of a native RNA molecule in a coleopteran pest. Thus, the nucleotide sequence(s) may comprise a segment encoding all or part of a ribonucleotide sequence present within a targeted coleopteran pest RNA transcript, and may comprise inverted repeats of all or a part of a targeted coleopteran pest transcript. A plant transformation vector may contain sequences specifically complementary to more than one target sequence, thus allowing production of more than one dsRNA for inhibiting expression of two or more genes in cells of one or more populations or species of target coleopteran pests. Segments of nucleotide sequence specifically complementary to nucleotide sequences present in different genes can be combined into a single composite nucleic acid molecule for expression in a transgenic plant. Such segments may be contiguous or separated by a spacer sequence.

In some embodiments, a plasmid of the present invention already containing at least one nucleotide sequence(s) of the invention can be modified by the sequential insertion of additional nucleotide sequence(s) in the same plasmid, wherein the additional nucleotide sequence(s) are operably linked to the same regulatory elements as the original at least one nucleotide sequence(s). In some embodiments, a nucleic acid molecule may be designed for the inhibition of multiple target genes. In some embodiments, the multiple genes to be inhibited can be obtained from the same coleopteran pest species, which may enhance the effectiveness of the nucleic acid molecule. In other embodiments, the genes can be derived from different coleopteran pests, which may broaden the range of coleopteran pests against which the agent(s) is/are effective. When multiple genes are targeted for suppression or a combination of expression and suppression, a polycistronic DNA element can be fabricated.

A recombinant nucleic acid molecule or vector of the present invention may comprise a selectable marker that confers a selectable phenotype on a transformed cell, such as a plant cell. Selectable markers may also be used to select for plants or plant cells that comprise recombinant nucleic acid molecule of the invention. The marker may encode biocide resistance, antibiotic resistance (e.g., kanamycin, Geneticin (G418), bleomycin, hygromycin, etc.), or herbicide resistance (e.g., glyphosate, etc.). Examples of selectable markers include, but are not limited to: a neo gene which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulfonylurea resistance; and a methotrexate resistant DHFR gene. Multiple selectable markers are available that confer resistance to ampicillin, bleomycin, chloramphenicol, gentamycin, hygromycin, kanamycin, lincomycin, methotrexate, phosphinothricin, puromycin, spectinomycin, rifampicin, streptomycin and tetracycline, and the like. Examples of such selectable markers are illustrated in, e.g., U.S. Pat. Nos. 5,550,318; 5,633,435; 5,780,708 and 6,118,047.

A recombinant nucleic acid molecule or vector of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson et al. (1987) Plant Mol. Biol. Rep. 5:387-405); an R-locus gene, which encodes a product that regulates the production of anthocyanin pigments (red color) in plant tissues (Dellaporta et al. (1988) "Molecular cloning of the maize R-nj allele by transposon tagging with Ac." In 18$^{th}$ Stadler Genetics Symposium, P. Gustafson and R. Appels, eds. (New York: Plenum), pp. 263-82); a β-lactamase gene (Sutcliffe et al. (1978) Proc. Natl. Acad. Sci. USA 75:3737-41); a gene which encodes an enzyme for which various chromogenic substrates are known (e.g., PADAC, a chromogenic cephalosporin); a luciferase gene (Ow et al. (1986) Science 234: 856-9); a xylE gene that encodes a catechol dioxygenase that can convert chromogenic catechols (Zukowski et al. (1983) Gene 46(2-3):247-55); an amylase gene (Ikatu et al. (1990) Bio/Technol. 8:241-2); a tyrosinase gene which encodes an enzyme capable of oxidizing tyrosine to DOPA and dopaquinone which in turn condenses to melanin (Katz et al. (1983) J. Gen. Microbiol. 129:2703-14); and an α-galactosidase.

In some embodiments, recombinant nucleic acid molecules, as described, supra, may be used in methods for the creation of transgenic plants and expression of heterologous nucleic acids in plants to prepare transgenic plants that exhibit reduced susceptibility to coleopteran pests. Plant transformation vectors can be prepared, for example, by inserting nucleic acid molecules encoding iRNA molecules into plant transformation vectors and introducing these into plants.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by Agrobacterium-mediated transformation (See, e.g., U.S. Pat. Nos. 5,563,055; 5,591, 616; 5,693,512; 5,824,877; 5,981,840; and 6,384,301) and by acceleration of DNA-coated particles (See, e.g., U.S. Pat. Nos. 5,015,580; 5,550,318; 5,538,880; 6,160,208; 6,399,861; and 6,403,865), etc. Techniques that are particularly useful for transforming corn are described, for example, in U.S. Pat. Nos. 7,060,876 and 5,591,616; and International PCT Publication WO 95/06722. Through the application of techniques such as these, the cells of virtually any species may be stably transformed. In some embodiments, transforming DNA is integrated into the genome of the host cell. In the case of multicellular species, transgenic cells may be regenerated into a transgenic organism. Any of these techniques may be used to produce a transgenic plant, for example, comprising one or more nucleic acid sequences encoding one or more iRNA molecules in the genome of the transgenic plant.

The most widely utilized method for introducing an expression vector into plants is based on the natural transformation system of Agrobacterium. A. tumefaciens and A. rhizogenes are plant pathogenic soil bacteria which genetically transform plant cells. The Ti and Ri plasmids of A. tumefaciens and A. rhizogenes, respectively, carry genes responsible for genetic transformation of the plant. The Ti (tumor-inducing)-plasmids contain a large segment, known as T-DNA, which is transferred to transformed plants. Another segment of the Ti plasmid, the vir region, is responsible for T-DNA transfer. The T-DNA region is bordered by terminal repeats. In modified binary vectors, the tumor-inducing genes have been deleted, and the functions of the vir region are utilized to transfer foreign DNA bordered by the T-DNA border sequences. The T-region may also contain a selectable marker for efficient recovery of transgenic plants and cells, and a multiple cloning site for inserting sequences for transfer such as a dsRNA encoding nucleic acid.

Thus, in some embodiments, a plant transformation vector is derived from a Ti plasmid of A. tumefaciens (See, e.g., U.S.

Pat. Nos. 4,536,475, 4,693,977, 4,886,937, and 5,501,967; and European Patent EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent EP 0 120 516, and those derived from any of the foregoing. Other bacteria such as *Sinorhizobium*, *Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic medium with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturation.

To confirm the presence of a nucleic acid molecule of interest (for example, a DNA sequence encoding one or more iRNA molecules that inhibit target gene expression in a coleopteran pest) in the regenerating plants, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant DNA sequence inserted into one chromosome. The single recombinant DNA sequence is referred to as a "transgenic event" or "integration event." Such transgenic plants are hemizygous for the inserted exogenous sequence. In some embodiments, a transgenic plant homozygous with respect to a transgene may be obtained by sexually mating (selfing) an independent segregant transgenic plant that contains a single exogenous gene sequence to itself, for example an $F_0$ plant, to produce $F_1$ seed. One fourth of the $F_1$ seed produced will be homozygous with respect to the transgene. Germinating $F_1$ seed results in plants that can be tested for heterozygosity, typically using an SNP assay or a thermal amplification assay that allows for the distinction between heterozygotes and homozygotes (i.e., a zygosity assay).

In particular embodiments, at least 2, 3, 4, 5, 6, 7, 8, 9 or 10 or more different iRNA molecules are produced in a plant cell that have a coleopteran pest-inhibitory effect. The iRNA molecules (e.g., dsRNA molecules) may be expressed from multiple nucleic acid sequences introduced in different transformation events, or from a single nucleic acid sequence introduced in a single transformation event. In some embodiments, a plurality of iRNA molecules are expressed under the control of a single promoter. In other embodiments, a plurality of iRNA molecules are expressed under the control of multiple promoters. Single iRNA molecules may be expressed that comprise multiple nucleic acid sequences that are each homologous to different loci within one or more coleopteran pests (for example, the loci defined by SEQ ID NO:4 and one or more of SEQ ID NOs:1-3), both in different populations of the same species of coleopteran pest, or in different species of coleopteran pests.

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising a nucleotide sequence that encodes an iRNA molecule may be introduced into a first plant line that is amenable to transformation to produce a transgenic plant, which transgenic plant may be crossed with a second plant line to introgress the nucleotide sequence that encodes the iRNA molecule into the genetic background of the second plant line.

Some embodiments of the invention also include commodity products containing one or more of the sequences of the present invention that are produced from a recombinant plant or seed containing one or more of the nucleotide sequences of the present invention. A commodity product containing one or more of the sequences of the present invention is intended to include, but not be limited to, meals, oils, crushed or whole grains or seeds of a plant, or any food product comprising any meal, oil, or crushed or whole grain of a recombinant plant or seed containing one or more of the sequences of the present invention. The detection of one or more of the sequences of the present invention in one or more commodity or commodity products contemplated herein is de facto evidence that the commodity or commodity product is composed of a transgenic plant designed to express one or more of the nucleotides sequences of the present invention for the purpose of controlling plant disease using dsRNA-mediated gene suppression methods.

In some aspects, seeds and commodity products produced by transgenic plants derived from transformed plant cells are included, wherein the seeds or commodity products comprise a detectable amount of a nucleic acid sequence of the invention. In some embodiments, such commodity products may be produced, for example, by obtaining transgenic plants and preparing food or feed from them. Commodity products comprising one or more of the nucleic acid sequences of the invention includes, for example and without limitation: meals, oils, crushed or whole grains or seeds of a plant, and any food product comprising any meal, oil, or crushed or whole grain of a recombinant plant or seed comprising one or more of the nucleic acid sequences of the invention. The detection of one or more of the sequences of the invention in one or more commodity or commodity products is de facto evidence that the commodity or commodity product is composed of a transgenic plant designed to express one or more of the iRNA molecules of the invention for the purpose of controlling coleopteran pests.

In some embodiments, a transgenic plant or seed comprising a nucleic acid molecule of the invention also may comprise at least one other transgenic event in its genome, including without limitation: a transgenic event from which is transcribed an iRNA molecule targeting a locus in a coleopteran pest other than the ones defined by SEQ ID NOs:1-4; a transgenic event from which is transcribed an iRNA molecule targeting a gene in an organism other than a coleopteran pest (e.g., a plant-parasitic nematode); a gene encoding an insecticidal protein (e.g., an *Bacillus thuringiensis* insecticidal protein); an herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility). In particular embodiments, sequences encoding iRNA molecules of the invention may be combined with disease control traits and other insect control traits in a plant to achieve desired traits for enhanced control of plant disease and insect damage. Combining insect control traits that employ distinct modes-of-action may provide protected transgenic plants with superior durability over plants harboring a single control trait, for example, because of the reduced probability that resistance to the trait(s) will develop in the field.

V. Target Gene Suppression in a Coleopteran Pest

A. Overview

In some embodiments of the invention, at least one nucleic acid molecule useful for the control of coleopteran pests may be provided to a coleopteran pest, wherein the nucleic acid molecule leads to RNAi-mediated gene silencing in the coleopteran pest. In particular embodiments, an iRNA molecule (e.g., dsRNA, siRNA, miRNA, and hpRNA) may be provided to the coleopteran host. In some embodiments, a nucleic acid molecule useful for the control of coleopteran pests may be provided to a coleopteran pest by contacting the nucleic acid molecule with the coleopteran pest. In these and further embodiments, a nucleic acid molecule useful for the control of coleopteran pests may be provided in a feeding substrate of the coleopteran pest, for example, a nutritional composition. In these and further embodiments, a nucleic acid molecule useful for the control of coleopteran pests may be provided through ingestion of plant material comprising the nucleic acid molecule that is ingested by the coleopteran pest. In certain embodiments, the nucleic acid molecule is present in plant material through expression of a recombinant nucleic acid sequence introduced into the plant material, for example, by transformation of a plant cell with a vector comprising the recombinant nucleic acid sequence and regeneration of a plant material or whole plant from the transformed plant cell.

B. RNAi-mediated Target Gene Suppression

In embodiments, the invention provides iRNA molecules (e.g., dsRNA, siRNA, miRNA, and hpRNA) that may be designed to target essential native nucleotide sequences (e.g., essential genes) in the genome and/or a cDNA library of a coleopteran pest (e.g., WCR or NCR), for example, by designing an iRNA molecule that comprises at least one strand comprising a nucleotide sequence that is specifically complementary to the target sequence. The sequence of an iRNA molecule so designed may be identical to the target sequence, or may incorporate mismatches that do not prevent specific hybridization between the iRNA molecule and its target sequence.

iRNA molecules of the invention may be used in methods for gene suppression in a coleopteran pest, thereby reducing the level or incidence of damage caused by the pest on a plant (for example, a protected transformed plant comprising an iRNA molecule). As used herein the term "gene suppression" refers to any of the well-known methods for reducing the levels of protein produced as a result of gene transcription to mRNA and subsequent translation of the mRNA, including the reduction of protein expression from a gene or a coding sequence including post-transcriptional inhibition of expression and transcriptional suppression. Post-transcriptional inhibition is mediated by specific homology between all or a part of an mRNA transcribed from a gene or coding sequence targeted for suppression and the corresponding iRNA molecule used for suppression. And, post-transcriptional inhibition refers to the substantial and measurable reduction of the amount of mRNA available in the cell for binding by ribosomes.

In embodiments wherein an iRNA molecule is a dsRNA molecule, the dsRNA molecule may be cleaved by the enzyme, DICER, into short siRNA molecules (approximately 20 nucleotides in length). The double-stranded siRNA molecule generated by DICER activity upon the dsRNA molecule may be separated into two single-stranded siRNAs; the "passenger strand" and the "guide strand." The passenger strand may be degraded, and the guide strand may be incorporated into RISC. Post-transcriptional inhibition occurs by specific hybridization of the guide strand with a specifically complementary sequence of an mRNA molecule, and subsequent cleavage by the enzyme, Argonaute (catalytic component of the RISC complex).

In embodiments of the invention, any form of iRNA molecule may be used. Those of skill in the art will understand that dsRNA molecules typically are more stable during preparation and during the step of providing the iRNA molecule to a cell than single-stranded RNA molecules, and are typically also more stable in a cell. Thus, while siRNA and miRNA molecules, for example, may be equally effective in some embodiments, a dsRNA molecule may be chosen due to its stability.

In particular embodiments, a nucleic acid molecule is provided that comprises a nucleotide sequence, which nucleotide sequence may be expressed in vitro to produce an iRNA molecule that is substantially homologous to a nucleic acid molecule encoded by a nucleotide sequence within the genome of a coleopteran pest. In certain embodiments, the in vitro transcribed iRNA molecule may be a stabilized dsRNA molecule that comprises a stem-loop structure. After a coleopteran pest contacts the in vitro transcribed iRNA molecule, post-transcriptional inhibition of a target gene in the coleopteran pest (for example, an essential gene) may occur.

In some embodiments of the invention, expression of a nucleic acid molecule comprising at least 19 contiguous nucleotides of a nucleotide sequence are used in a method for post-transcriptional inhibition of a target gene in a coleopteran pest, wherein the nucleotide sequence is selected from the group consisting of: SEQ ID NO:4; the complement of SEQ ID NO:4; a fragment of at least 19 contiguous nucleotides of SEQ ID NO:4; the complement of a fragment of at least 19 contiguous nucleotides of SEQ ID NO:4; a native coding sequence of a *Diabrotica* organism (e.g., WCR) comprising SEQ ID NO:4; the complement of a native coding sequence of a *Diabrotica* organism comprising SEQ ID NO:4; a native non-coding sequence of a *Diabrotica* organism that is transcribed into a native RNA molecule comprising SEQ ID NO:4; the complement of a native non-coding sequence of a *Diabrotica* organism that is transcribed into a native RNA molecule comprising SEQ ID NO:4; a fragment of at least 19 contiguous nucleotides of a native coding sequence of a *Diabrotica* organism comprising SEQ ID NO:4; the complement of a fragment of at least 19 contiguous nucleotides of a native coding sequence of a *Diabrotica* organism comprising SEQ ID NO:4; a fragment of at least 19 contiguous nucleotides of a native non-coding sequence of a *Diabrotica* organism that is transcribed into a native RNA molecule comprising SEQ ID NO:4; and the complement of a fragment of at least 19 contiguous nucleotides of a native non-coding sequence of a *Diabrotica* organism that is transcribed into a native RNA molecule comprising SEQ ID NO:4. In certain embodiments, the nucleic acid molecule comprises all or part of one or more of SEQ ID NOs:87-90, 137, and 138 (for example, all or part of any of SEQ ID NOs:88-90, 137, and 138). In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

In these and further embodiments, expression of at least one further nucleic acid molecule comprising at least 19 contiguous nucleotides of a nucleotide sequence may be used in a method for post-transcriptional inhibition of a target gene in a coleopteran pest, wherein the nucleotide sequence is selected from the group consisting of: SEQ ID NO:1; the complement of SEQ ID NO:1; SEQ ID NO:2; the complement of SEQ ID NO:2; SEQ ID NO:3; the complement of SEQ ID NO:3; a fragment of at least 19 contiguous nucleotides of any of SEQ ID NOs:1-3; the complement of a fragment of at least 19 contiguous nucleotides of any of SEQ ID NOs:1-3; a native coding sequence of a *Diabrotica* organism (e.g., WCR) comprising any of SEQ ID NOs:1-3; the complement of a native coding sequence of a *Diabrotica* organism comprising any of SEQ ID NOs:1-3; a native non-coding sequence of a *Diabrotica* organism that is transcribed into a native RNA molecule comprising any of SEQ ID NOs: 1-3; the complement of a native non-coding sequence of a *Diabrotica* organism that is transcribed into a native RNA molecule comprising any of SEQ ID NOs:1-3; a fragment of at least 19 contiguous nucleotides of a native coding sequence of a *Diabrotica* organism comprising any of SEQ ID NOs:1-3; the complement of a fragment of at least 19 contiguous nucleotides of a native coding sequence of a *Diabrotica* organism comprising any of SEQ ID NOs:1-3; a fragment of at least 19 contiguous nucleotides of a native non-coding sequence of a *Diabrotica* organism that is transcribed into a native RNA molecule comprising any of SEQ ID NOs:1-3; and the complement of a fragment of at least 19 contiguous nucleotides of a native non-coding sequence of a *Diabrotica* organism that is transcribed into a native RNA molecule comprising any of SEQ ID NOs:1-3. In certain embodiments, expression of a nucleic acid molecule that is at least 80% identical (e.g., 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 100%, and 100%) with any of the foregoing may be used. In these and further embodiments, a nucleic acid molecule may be expressed that specifically hybridizes to an RNA molecule present in at least one cell of a coleopteran pest.

It is an important feature of some embodiments of the invention that the RNAi post-transcriptional inhibition system is able to tolerate sequence variations among target genes that might be expected due to genetic mutation, strain polymorphism, or evolutionary divergence. The introduced nucleic acid molecule may not need to be absolutely homologous to either a primary transcription product or a fully-processed mRNA of a target gene, so long as the introduced nucleic acid molecule is specifically hybridizable to either a primary transcription product or a fully-processed mRNA of the target gene. Moreover, the introduced nucleic acid molecule may not need to be full-length, relative to either a primary transcription product or a fully processed mRNA of the target gene.

Inhibition of a target gene using the iRNA technology of the present invention is sequence-specific; i.e., nucleotide sequences substantially homologous to the iRNA molecule(s) are targeted for genetic inhibition. In some embodiments, an RNA molecule comprising a nucleotide sequence identical to a portion of a target gene sequence may be used for inhibition. In these and further embodiments, an RNA molecule comprising a nucleotide sequence with one or more insertion, deletion, and/or point mutations relative to a target gene sequence may be used. In particular embodiments, an iRNA molecule and a portion of a target gene may share, for example, at least from about 80%, at least from about 81%, at least from about 82%, at least from about 83%, at least from about 84%, at least from about 85%, at least from about 86%, at least from about 87%, at least from about 88%, at least from about 89%, at least from about 90%, at least from about 91%, at least from about 92%, at least from about 93%, at least from about 94%, at least from about 95%, at least from about 96%, at least from about 97%, at least from about 98%, at least from about 99%, at least from about 100%, and 100% sequence identity. Alternatively, the duplex region of a dsRNA molecule may be specifically hybridizable with a portion of a target gene transcript. In specifically hybridizable molecules, a less than full length sequence exhibiting a greater homology compensates for a longer, less homologous sequence. The length of the nucleotide sequence of a duplex region of a dsRNA molecule that is identical to a portion of a target gene transcript may be at least about 25, 50, 100, 200, 300, 400, 500, or at least about 1000 bases. In some embodiments, a sequence of greater than 20-100 nucleotides may be used. In particular embodiments, a sequence of greater than about 200-300 nucleotides may be used. In particular embodiments, a sequence of greater than about 500-1000 nucleotides may be used, depending on the size of the target gene.

In certain embodiments, expression of a target gene in a coleopteran pest may be inhibited by at least 10%; at least 33%; at least 50%; or at least 80% within a cell of the coleopteran pest, such that a significant inhibition takes place. Significant inhibition refers to inhibition over a threshold that results in a detectable phenotype (e.g., cessation of growth, cessation of feeding, cessation of development, and insect mortality, etc.), or a detectable decrease in RNA and/or gene product corresponding to the target gene being inhibited. Although in certain embodiments of the invention inhibition occurs in substantially all cells of the coleopteran pest, in other embodiments inhibition occurs only in a subset of cells expressing the target gene.

In some embodiments, transcriptional suppression is mediated by the presence in a cell of a dsRNA molecule exhibiting substantial sequence identity to a promoter DNA sequence or the complement thereof to effect what is referred to as "promoter trans suppression." Gene suppression may be effective against target genes in a coleopteran pest that may ingest or contact such dsRNA molecules, for example, by ingesting or contacting plant material containing the dsRNA molecules. dsRNA molecules for use in promoter trans suppression may be specifically designed to inhibit or suppress the expression of one or more homologous or complementary sequences in the cells of the coleopteran pest. Post-transcriptional gene suppression by antisense or sense oriented RNA to regulate gene expression in plant cells is disclosed in U.S. Pat. Nos. 5,107,065; 5,759,829; 5,283,184; and 5,231,020.

C. Expression of iRNA Molecules Provided to a Coleopteran Pest

Expression of iRNA molecules for RNAi-mediated gene inhibition in a coleopteran pest may be carried out in any one of many in vitro or in vivo formats. The iRNA molecules may then be provided to a coleopteran pest, for example, by contacting the iRNA molecules with the pest, or by causing the pest to ingest or otherwise internalize the iRNA molecules. Some embodiments of the invention include transformed host plants of a coleopteran pests, transformed plant cells, and progeny of transformed plants. The transformed plant cells and transformed plants may be engineered to express one or more of the iRNA molecules, for example, under the control of a heterologous promoter, to provide a pest-protective effect. Thus, when a transgenic plant or plant cell is consumed by a coleopteran pest during feeding, the pest may ingest iRNA molecules expressed in the transgenic plants or cells. The nucleotide sequences of the present invention may also be introduced into a wide variety of prokaryotic and eukaryotic microorganism hosts to produce iRNA molecules. The term "microorganism" includes prokaryotic and eukaryotic species, such as bacteria and fungi.

Modulation of gene expression may include partial or complete suppression of such expression. In another embodiment, a method for suppression of gene expression in a coleopteran pest comprises providing in the tissue of the host of the pest a gene-suppressive amount of at least one dsRNA molecule transcribed from a nucleotide sequence as described herein, at least one segment of which is complementary to an mRNA sequence within the cells of the coleopteran pest. A dsRNA molecule, including its modified form such as an siRNA, miRNA, or hpRNA molecule, ingested by a pathogenic microorganism in accordance with the invention may be at least from about 80%, 81%, 82%, 83%, 84%, 85%, 86%, 87%, 88%, 89%, 90%, 91%, 92%, 93%, 94%, 95%, 96%, 97%, 98%, 99%, or about 100% identical to an RNA molecule transcribed from a nucleic acid molecule comprising a nucleotide sequence selected from the group consisting of SEQ ID NOs:1-4. Isolated and substantially purified nucleic acid molecules including, but not limited to, non-naturally occurring nucleotide sequences and recombinant DNA constructs for transcribing dsRNA molecules of the present invention are therefore provided, which suppress or inhibit the expression of an endogenous coding sequence or a target coding sequence in the coleopteran pest when introduced thereto.

Particular embodiments provide a delivery system for the delivery of mRNA molecules for the post-transcription inhibition of one or more target gene(s) in a plant parasitic coleopteran pest and control of a population of the plant parasitic coleopteran pest. In some embodiments, the delivery system comprises ingestion of a host transgenic plant cell or contents of the host cell comprising RNA molecules transcribed in the host cell. In these and further embodiments, a transgenic plant cell or a transgenic plant is created that contains a recombinant DNA construct transcribing a stabilized dsRNA molecule of the invention. Transgenic plant cells and transgenic plants comprising nucleic acid sequences encoding a particular iRNA molecule may be produced by employing recombinant DNA technologies (which basic technologies are well-known in the art) to construct a plant transformation vector comprising a nucleotide sequence encoding an iRNA molecule of the invention (e.g., a stabilized dsRNA molecule); to transform a plant cell or plant; and to generate the transgenic plant cell or the transgenic plant that contains the transcribed iRNA molecule.

To impart coleopteran pest resistance to a transgenic plant, a recombinant DNA molecule may, for example, be transcribed into an iRNA molecule, such as a dsRNA molecule, an siRNA molecule, an miRNA molecule, or an hpRNA molecule. In some embodiments, an RNA molecule transcribed from a recombinant DNA molecule may form a dsRNA molecule within the tissues or fluids of the recombinant plant. Such a dsRNA molecule may be comprised in part of a nucleotide sequence that is identical to a corresponding nucleotide sequence transcribed from a DNA sequence within a coleopteran pest of a type that may parasitize the host plant. Expression of a target gene within the coleopteran pest is suppressed by the dsRNA molecule, and the suppression of expression of the target gene in the coleopteran pest results in the transgenic plant being resistant to the coleopteran pest. The modulatory effects of dsRNA molecules have been shown to be applicable to a variety of genes expressed in pests, including, for example, endogenous genes responsible for cellular metabolism or cellular transformation, including house-keeping genes; transcription factors; molting-related genes; and other genes which encode polypeptides involved in cellular metabolism or normal growth and development.

For transcription from a transgene in vivo or an expression construct, a regulatory region (e.g., promoter, enhancer, silencer, and polyadenylation signal) may be used in some embodiments to transcribe the RNA strand (or strands). Therefore, in some embodiments, as set forth, supra, a nucleotide sequence for use in producing iRNA molecules may be operably linked to one or more promoter sequences functional in a plant host cell. The promoter may be an endogenous promoter, normally resident in the host genome. The nucleotide sequence of the present invention, under the control of an operably linked promoter sequence, may further be flanked by additional sequences that advantageously affect its transcription and/or the stability of a resulting transcript. Such sequences may be located upstream of the operably linked promoter, downstream of the 3' end of the expression construct, and may occur both upstream of the promoter and downstream of the 3' end of the expression construct.

Some embodiments provide methods for reducing the damage to a host plant (e.g., a corn plant) caused by a coleopteran pest that feeds on the plant, wherein the method comprises providing in the host plant a transformed plant cell expressing at least one nucleic acid molecule of the invention, wherein the nucleic acid molecule(s) functions upon being taken up by the coleopteran pest to inhibit the expression of a target sequence within the coleopteran pest, which inhibition of expression results in mortality, reduced growth, and/or reduced reproduction of the coleopteran pest, thereby reducing the damage to the host plant caused by the coleopteran pest. In some embodiments, the nucleic acid molecule(s) comprise dsRNA molecules. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consist of one nucleotide sequence that is specifically hybridizable to a nucleic acid molecule expressed in a coleopteran pest cell.

In some embodiments, a method for increasing the yield of a corn crop is provided, wherein the method comprises introducing into a corn plant at least one nucleic acid molecule of the invention; cultivating the corn plant to allow the expression of an iRNA molecule comprising the nucleic acid sequence, wherein expression of an iRNA molecule comprising the nucleic acid sequence inhibits coleopteran pest damage and/or growth, thereby reducing or eliminating a loss of yield due to coleopteran pest infestation. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consist of one nucleotide sequence that is specifically hybridizable to a nucleic acid molecule expressed in a coleopteran pest cell.

In some embodiments, a method for modulating the expression of a target gene in a coleopteran pest is provided, the method comprising: transforming a plant cell with a vector comprising a nucleic acid sequence encoding at least one nucleic acid molecule of the invention, wherein the nucleotide sequence is operatively-linked to a promoter and a transcription termination sequence; culturing the transformed plant cell under conditions sufficient to allow for development of a plant cell culture including a plurality of transformed plant cells; selecting for transformed plant cells that have integrated the nucleic acid molecule into their genomes; screening the transformed plant cells for expression of an iRNA molecule encoded by the integrated nucleic acid molecule; selecting a transgenic plant cell that expresses the iRNA molecule; and feeding the selected transgenic plant cell to the coleopteran pest. Plants may also be regenerated from transformed plant cells that express an iRNA molecule encoded by the integrated nucleic acid molecule. In some embodiments, the iRNA molecule is a dsRNA molecule. In these and further embodiments, the nucleic acid molecule(s) comprise dsRNA molecules that each comprise more than one nucleotide sequence that is specifically hybridizable to a nucleic acid molecule expressed in a coleopteran pest cell. In some embodiments, the nucleic acid molecule(s) consist of one nucleotide sequence that is specifically hybridizable to a nucleic acid molecule expressed in a coleopteran pest cell.

iRNA molecules of the invention can be incorporated within or on the seeds of a plant species (e.g., corn), either as a product of expression from a recombinant gene incorporated into a genome of the plant cells, or as incorporated into a coating or seed treatment that is applied to the seed before planting. A plant cell comprising a recombinant gene is considered to be a transgenic event. Also included are delivery systems for the delivery of iRNA molecules to coleopteran pests. For example, the iRNA molecules of the invention may be directly introduced into the cells of a coleopteran pest. Methods for introduction may include direct mixing of iRNA with plant tissue from a host for the coleopteran pest, as well as application of compositions comprising iRNA molecules of the invention to host plant tissue. For example, iRNA molecules may be sprayed onto a plant surface. Alternatively, an iRNA molecule may be expressed by a microorganism, and the microorganism may be applied onto the plant surface, or introduced into a root or stem by a physical means such as an injection. As discussed, supra, a transgenic plant may also be genetically engineered to express at least one iRNA molecule in an amount sufficient to kill the coleopteran pests known to infest the plant. iRNA molecules produced by chemical or enzymatic synthesis may also be formulated in a manner consistent with common agricultural practices, and used as spray-on products for controlling plant disease. The formulations may include the appropriate stickers and welters required for efficient foliar coverage, as well as UV protectants to protect iRNA molecules (e.g., dsRNA molecules) from UV damage. Such additives are commonly used in the bioinsecticide industry, and are well known to those skilled in the art. Such applications may be combined with other spray-on insecticide applications (biologically based or otherwise) to enhance plant protection from coleopteran pests.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

The following Examples are provided to illustrate certain particular features and/or aspects. These Examples should not be construed to limit the disclosure to the particular features or aspects described.

EXAMPLES

Example 1

Materials and Methods

Sample Preparation and Bioassays

A number of dsRNA molecules (including Caf1-180; vacuolar-ATPase (v-ATPase) subunit C region 1; v-ATPase subunit C region 2; v-ATPase subunit H region 1; v-ATPase subunit H region 2; and Rho1) were synthesized and purified using a MEGAscript® RNAi kit (AMBION, Foster City, Calif.). The purified dsRNA molecules were prepared in TE buffer, and all bioassays contained a control treatment consisting of this buffer, which served as a background check for mortality or growth inhibition of WCR. The concentrations of dsRNA molecules in the bioassay buffer were measured using a Nanoprop™ 8000 spectrophotometer (Thermo Scientific, Wilmington, Del.).

Samples were tested for insect activity in bioassays conducted with neonate insect larvae on artificial insect diet. WCR eggs were obtained from Crop Characteristics, Inc. (Farmington, Minn.).

The bioassays were conducted in 128-well plastic trays specifically designed for insect bioassays (C-D International, Pitman, N.J.). Each well contained approximately 1.0 mL of a diet designed for growth of coleopteran insects. A 60 µL aliquot of protein sample was delivered by pipette onto the 1.5 cm² diet surface of each well (40 µL/cm²). dsRNA sample concentrations were calculated as the amount of dsRNA per square centimeter (ng/cm²) of surface area in the well. The treated trays were held in a fume hood until the liquid on the diet surface evaporated or was absorbed into the diet.

Within a few hours of eclosion, individual larvae were picked up with a moistened camel hair brush and deposited on the treated diet (one or two larvae per well). The infested wells of the 128-well plastic trays were then sealed with adhesive sheets of clear plastic, and vented to allow gas exchange. Bioassay trays were held under controlled environmental conditions (28° C., ~40% Relative Humidity, 16:8 [Light:Dark]) for 9 days, after which the total number of insects exposed to each sample, the number of dead insects, and the weight of surviving insects were recorded. Percent mortality, average live weights, and growth inhibition were calculated for each treatment. Stunting was defined as a decrease in average live weights. Growth inhibition (GI) was calculated as follows:

$$GI=[1-(TWIT/TNIT)/(TWIBC/TNIBC)]$$

where TWIT is the Total Weight of live Insects in the Treatment;

TNIT is the Total Number of Insects in the Treatment;

TWIBC is the Total Weight of live Insects in the Background Check (Buffer control); and TNIBC is the Total Number of Insects in the Background Check (Buffer control).

The $GI_{50}$ is determined to be the concentration of sample in the diet at which the GI value is 50%. The $LC_{50}$ (50% Lethal Concentration) is recorded as the concentration of sample in the diet at which 50% of test insects are killed. Statistical analysis was done using JMP™ software (SAS, Cary, N.C.).

Replicated bioassays demonstrated that ingestion of samples result in a surprising and unexpected mortality and growth inhibition of corn rootworm larvae.

Example 2

Identification of Candidate Target Genes

First-instar WCR larvae were selected for transcriptome analysis because control at this growth stage by transgenic insect resistance technology would be advantageous.

Total RNA was isolated from about 0.9 gm whole first-instar WCR larvae (*Diabrotica virgifera virgifera* LeConte; 4 to 5 days post-hatch, held at 16° C.) and purified using the following phenol/TRI REAGENT®-based method (Molecular Research Center, Cincinnati, Ohio; Cat. No. TR 118):

Larvae were homogenized at room temperature in a 15 mL homogenizer with 10 mL of TRI REAGENT® until a homogenous suspension was obtained. Following 5 min. incubation at room temperature, the homogenate was dispensed into 1.5 mL microfuge tubes (1 mL per tube), 200 µL of chloroform was added, and the mixture was vigorously shaken for 15 seconds. After allowing the extraction to sit at room temperature for 10 min, the phases were separated by centrifugation at 12,000×g at 4° C. The upper phase (comprising about 0.6 mL) was carefully transferred into another sterile 1.5 mL tube, and an equal volume (0.6 mL) of room temperature isopropanol was added. After incubation at room temperature for 5 to 10 min, the mixture was centrifuged 8 min at 12,000×g (4° C. or 25° C.).

The supernatant was carefully removed and discarded, and the RNA pellet was washed twice by vortexing with 75% ethanol, with recovery by centrifugation for 5 mM at 7,500×g (4° C. or 25° C.) after each wash. The ethanol was carefully removed, the pellet was allowed to air-dry for 3 to 5 min, and then was dissolved in nuclease-free sterile water. RNA concentration was determined by measuring the absorbance (A) at 260 nm and 280 nm. A typical extraction from about 0.9 g of larvae yielded over 1 mg of total RNA, with an A260/A280 ratio of 1.9. The RNA thus extracted was stored at −80° C. until further processed.

RNA quality was determined by running an aliquot through a 1% agarose gel. The agarose gel solution was made using autoclaved 10×TAE buffer (Tris-acetate EDTA, 1× concentration is 0.04M Tris-acetate, 1 mM EDTA (ethylenediamine tetra-acetic acid sodium salt, pH 8.0) diluted with DEPC (diethyl pyrocarbonate)-treated water in an autoclaved container. 1×TAE was used as the running buffer. Before use, the electrophoresis tank and the well-forming comb were cleaned with RNAseAway™ (Invitrogen Inc., Carlsbad, Calif.). Two µL of RNA sample were mixed with 8 µL of TE buffer (10 mM Tris HCl pH 7.0; 1 mM EDTA) and 10 µL of RNA sample buffer (Novagen® Catalog No 70606; EMD4 Bioscience, Gibbstown, N.J.). The sample was heated at 70° C. for 3 min, cooled to room temperature, and 5 µL were loaded per well (containing 1 to 2 µg RNA). Commercially available RNA molecular weight markers were simultaneously run in separate wells for molecular size comparison. The gel was run at 60 v for 2 hr.

A normalized cDNA library was prepared from the larval total RNA by a commercial service provider (Eurofins MWG Operon, Huntsville, Ala.), using random priming.

The normalized larval cDNA library was sequenced at ½ plate scale by GS FLX 454 Titanium™ series chemistry at Eurofins MWG Operon, which resulted in over 600,000 reads with an average read length of 348 bp. 350,000 reads were assembled into over 50,000 contigs. Both the unassembled reads and the contigs were converted into BLASTable databases using the publicly available program, FORMATDB (available from the National Center for Biological Information (NCBI)).

Candidate genes for RNAi targeting were selected using information regarding lethal RNAi effects of particular genes in other insects such as *Drosophila* and *Tribolium*. These genes were hypothesized to be essential for survival and growth in coleopteran insects. Selected target gene homologs were identified in the transcriptome sequence database as described below. Full-length or partial sequences of the target genes were amplified by PCR to prepare templates for double-stranded RNA (dsRNA) production.

TBLASTN searches using candidate protein coding sequences were run against BLASTable databases containing the unassembled *Diabrotica* sequence reads or the assembled contigs. Significant hits to a *Diabrotica* sequence (defined as better than $e^{-20}$ for contigs homologies and better than $e^{-10}$ for unassembled sequence reads homologies) were confirmed using BLASTX against the NCBI non-redundant database. The results of this BLASTX search confirmed that the *Diabrotica* homolog candidate gene sequences identified in the TBLASTN search indeed comprised *Diabrotica* genes, or were the best hit available in the *Diabrotica* sequences to the non-*Diabrotica* candidate gene sequence. In most cases, *Tribolium* candidate genes which were annotated as encoding a protein gave an unambiguous sequence homology to a sequence or sequences in the *Diabrotica* transcriptome sequences. In a few cases, it was clear that some of the *Diabrotica* contigs or unassembled sequence reads selected by homology to a non-*Diabrotica* candidate gene overlapped, and that the assembly of the contigs had failed to join these overlaps. In those cases, Sequencher™ v4.9 (Gene Codes Corporation, Ann Arbor, Mich.) was used to assemble the sequences into longer contigs.

A plurality of candidate target genes were identified as genes that may lead to coleopteran pest mortality or growth, development, or reproduction inhibition in WCR, including SEQ ID NOs:1-4. Full-length or partial clones of sequences of *Diabrotica* candidate gene homologs were used to generate PCR amplicons for dsRNA synthesis.

SEQ ID NO:1 corresponds to D_vir_c47185, which is a homolog of Caf1-180, and is herein referred to as Caf1-180. *Drosophila* Caf1-180 has been shown to function in delivering histones onto newly synthesized DNA, and Caf1-180. Loss of function mutations in *Drosophila* Caf1-180 have been shown to cause arrest of larval growth and development, and larval mortality (Klapholz et al. (2009) Chromosoma 118(2):235-48; Tyler et al. (2001) Mol. Cell. Biol. 21(19): 6574-84; Song et al. (2007) Dev. Biol. 311(1):213-22).

SEQ ID NO:2 corresponds to D_vir_c1229, which is a homolog of vacuolar ATPase subunit C, and is herein referred to as VatpaseC. SEQ ID NOs:5-8 are non-contiguous sequence fragments of VatpaseC.

SEQ ID NO:3 corresponds to D_vir_c1319, which is a homolog of vacuolar ATPase subunit H, and is herein referred to as VatpaseH. SEQ ID NOs:9-11 are non-contiguous sequence fragments of VatpaseH.

*Drosophila* vacuolar ATPase is a multi-subunit proton transporter involved in Notch signaling (Vaccari et al. (2010) Development 137(10):1825-32). Loss of function mutations in *Drosophila* vacuolar ATPase subunits have been shown to be recessive lethal (Allan et al. (2005) Physiol. Genomics 22(2):128-38; and Davies et al. (1996) J. Biol. Chem. 271 (48):30677-84). VATPaseC (Vha44) and VATPaseH (VhaSFD) are two of the subunits of *Drosophila* vacuolar ATPase.

SEQ ID NO:4 is Contig_01_Rho1_1-191_CDC42, herein referred to as Rho1. *Drosophila* Rho1 functions in regulating assembly and disassembly of actin filaments, and loss of function mutations in *Drosophila* Rho1 have a significant impact on cellular component movement, synapse remodeling, larval development, and response to stress (Fox et al. (2005) Development 132(21):4819-31; Kadandale et al. (2010) Proc. Natl. Acad. Sci. U.S.A. 107(23):10502-7; Rosales-Nieves et al. (2006) Nat. Cell Biol. 8(4):367-76; Magie and Parkhurst (2005) Dev. Biol. 278(1):144-54; and Xu et al. (2008) Dev. Biol. 321(1):88-100).

Example 3

Amplification of Target Genes

Primers were designed to amplify portions of coding regions of each target gene by PCR. See Table 1. Where appropriate, a T7 phage promoter sequence (TTAATAC-GACTCACTATAGGGAGA (SEQ ID NO:12)) was incorporated into the 5' end of the amplified sense or antisense strands. See Table 1. Genomic DNA was extracted from WCR, and the PCR primers were used to amplify all or part of the native target gene sequence from the genomic DNA via a PCR reaction.

TABLE 1

Sequences and pairings of PCR primers used to prepare templates for dsRNA production.

| | Gene (Region) | Primer ID | SEQ ID NO: | Sequence |
|---|---|---|---|---|
| Pair 1 | Caf1-180 (1) | Caf-FT7 | SEQ ID NO: 13 | TTAATACGACTCACTATAGGGAGATTCGGAAGCTT CATATTTAAAAGATC |
| | Caf1-180 (1) | Caf-R | SEQ ID NO: 14 | TATCTTCAGCCAAAGGTTTTCTTG |
| Pair 2 | Caf1-180 (1) | Caf-F | SEQ ID NO: 15 | TTCGGAAGCTTCATATTTAAAAGATC |
| | Caf1-180 (1) | Caf-RT7 | SEQ ID NO: 16 | TTAATACGACTCACTATAGGGAGATATCTTCAGCC AAAGGTTTTCTTG |
| Pair 3 | VatpaseC (1) | Atp.C-F1T7 | SEQ ID NO: 17 | TTAATACGACTCACTATAGGGAGAAGAAGAAATG ACTGAGTATTGG |
| | VatpaseC (1) | Atp.C-R1 | SEQ ID NO: 18 | CTGAAGACTTCCTTTCAAGT |
| Pair 4 | VatpaseC (1) | Atp.C-F1 | SEQ ID NO: 19 | AGAAGAAATGACTGAGTATTGG |
| | VatpaseC (1) | Atp.C-R1T7 | SEQ ID NO: 20 | TTAATACGACTCACTATAGGGAGACTGAAGACTTC CTTTCAAGT |
| Pair 5 | VatpaseC (1) | Atp.C-F1 | SEQ ID NO: 19 | AGAAGAAATGACTGAGTATTGG |
| | VatpaseC (1) | Atp.C-R1shortT7 | SEQ ID NO: 21 | TTAATACGACTCACTATAGGGAGAGATGGGATATT TGGCGATGTCCCA |
| Pair 6 | VatpaseC (1) | Atp.C-F1T7 | SEQ ID NO: 17 | TTAATACGACTCACTATAGGGAGAAGAAGAAATG ACTGAGTATTGG |
| | VatpaseC (1) | Atp.C-R1short | SEQ ID NO: 22 | GATGGGATATTTGGCGATGTCCCA |
| Pair 7 | VatpaseC (2) | Atp.C-F2T7 | SEQ ID NO: 23 | TTAATACGACTCACTATAGGGAGAAGAAACAGAC AGGAAGTTTACT |
| | VatpaseC (2) | Atp.C-R2 | SEQ ID NO: 24 | GGATTAAAATAGCTTGGAAATTGAC |
| Pair 8 | VatpaseC (2) | Atp.C-F2 | SEQ ID NO: 25 | AGAAAcAGAcAGGAAGmAcT |
| | VatpaseC (2) | Atp.C-R2T7 | SEQ ID NO: 26 | TTAATACGACTCACTATAGGGAGAGGATTAAAATA GCTTGGAAATTGAC |
| Pair 9 | VatpaseH (1) | Atp.H-F1T7 | SEQ ID NO: 27 | TTAATACGACTCACTATAGGGAGA TCATGATTGTTCCAGATATGTTGG |
| | VatpaseH (1) | Atp.H-R1 | SEQ ID NO: 28 | AGTGTCTGCGACCAACAAGC |

TABLE 1-continued

Sequences and pairings of PCR primers used to prepare templates for dsRNA production.

| | Gene (Region) | Primer ID | SEQ ID NO: | Sequence |
|---|---|---|---|---|
| Pair 10 | VatpaseH (1) | Atp.H-F1 | SEQ ID NO: 29 | TCATGATTGTTCCAGATATGTTGG |
| | VatpaseH (1) | Atp.H-R1T7 | SEQ ID NO: 30 | TTAATACGACTCACTATAGGGAGAAGTGTCTGCGACCAACAAGC |
| Pair 11 | VatpaseH (2) | Atp.H-F2T7 | SEQ ID NO: 31 | TTAATACGACTCACTATAGGGAGAAGAACATTGTATAGCTATGGTG |
| | VatpaseH (2) | Atp.H-R2 | SEQ ID NO: 32 | ATTTACGCCTTGCCTGCGAC |
| Pair 12 | VatpaseH (2) | Atp.H-F2 | SEQ ID NO: 33 | AGAACATTGTATAGCTATGGTG |
| | VatpaseH (2) | Atp.H-R2T7 | SEQ ID NO: 34 | TTAATACGACTCACTATAGGGAGAATTTACGCCTTGCCTGCGAC |
| Pair 13 | Rho1 (1) | Rho1-FT7 | SEQ ID NO: 35 | TTAATACGACTCACTATAGGGAGACAGGTCCGATGGCTGCAATAAG |
| | Rho1 (1) | Rho1-R | SEQ ID NO: 36 | GACTTGCAGTGCAGCTCGGG |
| Pair 14 | Rho1 (1) | Rho1-F | SEQ ID NO: 37 | CAGGTCCGATGGCTGCAATAAG |
| | Rho1 (1) | Rho1-RT7 | SEQ ID NO: 38 | TTAATACGACTCACTATAGGGAGAGACTTGCAGTGCAGCTCGGG |

Example 4

RNAi Constructs

Template Preparation by PCR and dsRNA Synthesis.

The strategy used to provide specific templates for in vitro dsRNA production is shown in FIG. 1. Template DNAs intended for use in dsRNA synthesis were prepared by PCR using the primer pairs in Table 1 and (as PCR template) first-strand cDNA prepared from total RNA isolated from WCR first-instar larvae. For each selected target gene region, two separate PCR amplifications were performed. The first PCR amplification introduced a T7 promoter sequence at the 5' end of the amplified sense strands. The second reaction incorporated the T7 promoter sequence at the 5' ends of the antisense strands. The two PCR amplified fragments for each region of the target genes were then mixed in approximately equal amounts, and the mixture was used as transcription template for dsRNA production. FIG. 1. Double-stranded RNA was synthesized and purified using an Ambion® MEGAscript® RNAi kit following the manufacturer's instructions (Foster City, Calif.). The sequences of the dsRNA templates amplified with the particular primers were: SEQ ID NO:86 (Caf1-180); SEQ ID NOs:7 and 8 (VatpaseC); SEQ ID NOs:10 and 11 (VatpaseH); and SEQ ID NO:87 (Rho1). The concentrations of dsRNAs were measured using a Nanoprop™ 8000 spectrophotometer (Thermo Scientific, Wilmington, Del.).

Construction of Plant Transformation Vectors—Method 1

Standard Multi-site Gateway® (Invitrogen) cloning methods were used to construct hairpin RNA (hpRNA) expression vectors for WHISKERS™-mediated maize cell transformation. Separate entry vectors were constructed for the two marker genes utilized for screening/selection of maize cells after transformation; a yellow fluorescent protein gene (YFP, Shagin et al. (2004) Mol. Biol. Evol. 21(5):841-50) and a herbicide tolerance gene (phosphinothricin acetyl transferase (PAT), Wehrmann et al. (1996) Nat. Biotechnol. 14(10):1274-8). The expression of each of these was controlled by a copy of a rice actin1 promoter (OsAct1, U.S. Pat. No. 5,641,876). A fragment comprising a 3' untranslated region from a maize peroxidase 5 gene (ZmPer5 3' UTR v2, U.S. Pat. No. 6,699,984) was used to terminate transcription of the genes.

A third type of entry vector, designed for hpRNA production, was also constructed utilizing fragments of the Caf1-180 gene or the VatpaseC gene. Target gene regions for Caf1-180 and VatpaseC were amplified for hairpin synthesis using the primers set forth in Table 2. Intramolecular hairpin formation by RNA primary transcripts was facilitated by arranging (within a single transcription unit) two copies of the target gene fragment in opposite orientation to one another, the two fragments being separated by an ST-LS1 intron sequence (Vancanneyt et al., (1990) Mol. Gen. Genet. 220(2):245-50). Production of the primary mRNA transcript was driven by a copy of the maize ubiquitin 1 promoter (U.S. Pat. No. 5,510,474). Thus, the primary mRNA transcript contains the two gene fragment sequences as large inverted repeats of one another, separated by the intron sequence. A fragment comprising a 3' untranslated region from a maize lipase gene (ZmLip 3' UTR, U.S. Pat. No. 7,179,902) was used to terminate transcription of the genes.

TABLE 2

Sequences and pairings of primers used to prepare hairpin constructs for maize transformation.

| | Gene | Primer ID | SEQ ID NO: | Sequence |
|---|---|---|---|---|
| Pair 15 | Caf1-180 | hpCaf-F | SEQ ID NO: 39 | GAGAGGTACCTCGGAAGCTTCATATTTAAAAGATCTGTC |
| | Caf1-180 | hpCaf-R | SEQ ID NO: 40 | CTCTGGATCCAAAATGTTTTTTATCTTCAGCCAAAGGTTTTC |
| Pair 16 | Caf1-180 | hp-invCaf-F | SEQ ID NO: 41 | AGAGCCATGGAAAATGTTTTTTATCTTCAGCCAAAGGTTTTC |

TABLE 2-continued

Sequences and pairings of primers used to prepare hairpin constructs for maize transformation.

| | Gene | Primer ID | SEQ ID NO: | Sequence |
|---|---|---|---|---|
| | Caf1-180 | hp-invCaf-R | SEQ ID NO: 42 | CTCTGAGCTCTCGGAAGCTTCATATTTAAAAGATCTGTC |
| Pair 17 | ST-SL1 | ST-LS1-F | SEQ ID NO: 43 | AGAGGGATCCAGGCCTAGGTATGTTTCTGCTTCTACCTTTGAT |
| | ST-SL1 | ST-LS1-R | SEQ ID NO: 44 | CTCTCCATGGACCGGTATTTAAATACCTGCACATCACCATGTTTTGG |
| Pair 18 | VatpaseC | hpATPaseC-F | SEQ ID NO: 45 | AGAGGGTACCAGAAGAAATGACTGAGTATTGGTTGATATC |
| | VatpaseC | hpATPaseC-R | SEQ ID NO: 46 | CTCTGGATCCGATGGGATATTTGGCGATGTCC |
| Pair 19 | VatpaseC | hp-invATPaseC-F | SEQ ID NO: 47 | AGAGCCATGGGATGGGATATTTGGCGATGTCC |
| | VatpaseC | hp-invATPaseC-R | SEQ ID NO: 48 | GCTGAGCTCAGAAGAAATGACTGAGTATTGGTTGATATC |

SEQ ID NO:49 presents a Caf1-180 hairpin-forming sequence, and SEQ ID NO:50 presents a VatpaseC hairpin-forming sequence.

Two versions of hpRNA expression entry vectors were constructed for each of Caf1-180 and VatpaseC. In a first version of the entry vectors, a maize consensus translational start context sequence was present in the mRNA 5' untranslated leader sequence, adjacent to the 5' end of the first target gene fragment sequence, which was present in the "direct" orientation (that is in the sense orientation relative to the promoter). The maize consensus translational start sequence was omitted in a second version.

A standard GATEWAY® recombination reaction was performed with 3 entry vectors and a destination vector (pDAB104124) using LR CLONASE II PLUS™ from Invitrogen. In a completed hpRNA expression vector, the hpRNA cassette was flanked by the YFP and PAT gene expression cassettes.

Fragment purification for WHISKERS™-mediated transformation was accomplished on a preparative scale by high pressure liquid chromatography (HPLC) after the YFP/hpRNA/PAT expression vector DNAs had been digested with either Bcl I (for Caf1-180 constructs) or Bbs I plus Afe I (for VatpaseC constructs) to remove the bacterial spectinomycin resistance gene present in the vector backbone.

Construction of Plant Transformation Vectors—Method 2

WHISKERS™ Destination Vector:

Standard one-site GATEWAY® (INVITROGEN) cloning methodology was used to construct a hairpin RNA (hpRNA) expression vector for WHISKERS™-mediated maize cell transformation. Two marker genes were incorporated into a destination vector (named pDAB108916) and were utilized for screening and selection of maize cells after transformation. A yellow fluorescent protein gene (YFP, Shagin et al. (2004) Mol. Biol. Evol. 21(5):841-50) was used for visual screening, and an herbicide tolerance gene (phosphinothricin acetyl transferase (PAT), Wehrmann et al. (1996) Nat. Biotechnol. 14(10):1274-8) was used for selection of transformants. The expression of each of the two marker genes was controlled by separate copies of a sugarcane bacilliform badnavirus (SCBV) promoter (U.S. Pat. No. 6,489,462) comprising a chimeric 5'UTR sequence assembled from a portion of the 5'UTR of the maize streak virus coat protein gene (GENBANK Accession X01633) and intron1 from a maize alcohol dehydrogenase 1 gene (GENBANK Accession X04049). A fragment comprising a 3'UTR from a maize lipase gene (Zm-Lip 3' UTR; U.S. Pat. No. 7,179,902) and a fragment comprising a 3'UTR from potato (Solanum tuberosum) StPinII 3'UTR (An et al. (1989) Plant Cell. 1:115-122) were used to terminate transcription of the YFP and PAT genes, respectively.

A first entry vector designed for hpRNA production was constructed utilizing DNA fragments bearing a Caf1-180 v3 sense (+ST-LS1 intron) (SEQ ID NO:95) and fragments bearing a Caf1-180 v3 antisense sequence (SEQ ID NO:96). These fragments were separately synthesized by a commercial vendor (DNA2.0; Menlo Park, Calif.). The synthetic pieces were joined in appropriate orientation by standard cloning methods to form the hairpin-forming construct of SEQ ID NO:97, and the construct was cloned between a promoter and 3'UTR sequence in the entry vector. Production of the primary mRNA transcript was driven by a copy of the maize ubiquitin 1 promoter (U.S. Pat. No. 5,510,474), while a sequence comprising a 3' untranslated region from a maize peroxidase 5 gene (ZmPer5 3' UTR v2, U.S. Pat. No. 6,699,984) was used to terminate transcription of the target gene fragment. Intramolecular hairpin formation by RNA primary transcripts was facilitated by arranging (within a single transcription unit) two copies of the target gene fragment in opposite orientation to one another, the two fragments being separated by an ST-LS1 intron sequence (Vancanneyt et al., (1990) Mol. Gen. Genet. 220(2):245-50). Thus, the primary mRNA transcript contains the two gene fragment sequences as large inverted repeats of one another, separated by the intron sequence.

A standard GATEWAY® recombination reaction was performed with the constructed Caf-180 v3 hairpin entry vector and destination vector pDAB108916, using LR CLONASE II PLUS™ from INVITROGEN. In a completed Caf-180 v3 hpRNA expression vector (pDAB109830), the YFP gene expression cassette was flanked by the hpRNA and PAT gene expression cassettes.

In similar fashion, standard one-site GATEWAY® cloning methods were used to construct other hairpin RNA (hpRNA) expression vectors for WHISKERS™-mediated maize cell transformation. These additional vectors comprised hpRNA constructs for VatpaseC v3, VatpaseC v4, VatpaseH v1 and Rho1 v1.

A second entry vector designed for hpRNA production was constructed utilizing synthetic fragments comprising a VatpaseC v3 sense (+ST-LS1 intron) sequence (SEQ ID NO:98) and a VatpaseC v3 antisense sequence (SEQ ID NO:99), joined in appropriate orientation (SEQ ID NO:100) by standard cloning methods. The VaptaseC v3 entry vector was used for GATEWAY® cloning with the destination vector (pDAB108916) to construct VatpaseC v3 hpRNA expression vector pDAB 109828.

A third entry vector designed for hpRNA production was constructed utilizing synthetic fragments comprising a VatpaseC v4 sense (+ST-LS1 intron) sequence (SEQ ID NO:101) and a VatpaseC v4 antisense sequence (SEQ ID NO:102), joined in appropriate orientation (SEQ ID NO:103) by standard cloning methods. The VatpaseC v4 entry vector was used for GATEWAY® cloning with the destination vector (pDAB108916) to construct VatpaseC v4 hpRNA expression vector pDAB 109838.

A fourth entry vector designed for hpRNA production was constructed utilizing synthetic fragments comprising a VatpaseH v1 sense (+ST-LS1 intron) sequence (SEQ ID NO:104) and a Vatpase H v1 antisense sequence (SEQ ID NO:105), joined in appropriate orientation (SEQ ID NO:106) by standard cloning methods. The VatpaseH v1 entry vector was used for GATEWAY® cloning with the destination vector (pDAB108916) to construct VatpaseH v1 hpRNA expression vector pDAB 109829.

A fifth entry vector designed for hpRNA production was constructed utilizing synthetic fragments comprising a Rho1 v1 sense (+ST-LS1 intron) sequence (SEQ ID NO:107) and a Rho1 v1 antisense sequence (SEQ ID NO:108), joined in appropriate orientation (SEQ ID NO:109) by standard cloning methods. The Rho1 v1 entry vector was used for GATEWAY® cloning with the destination vector (pDAB108916) to construct Rho1 v1 hpRNA expression vector pDAB109834.

WHISKERS™-mediated transformation was accomplished using purified circular plasmid DNA. EXAMPLE 9. *Agrobacterium* Destination Vector:

Standard GATEWAY® (INVITROGEN) cloning methods were used to construct hairpin RNA (hpRNA) expression vectors for *Agrobacterium*-mediated maize embryo transformation. Entry vectors prepared above for production of hpRNAs for Caf-180 v3, VatpaseC v3, VatpaseH v1 and Rho1 v1 were used for GATEWAY® cloning with a destination vector (pDAB 108915) constructed as an *Agrobacterium* plant transformation binary vector. Between the left and right T-DNA border repeat sequences was included a plant selectable marker/herbicide tolerance gene comprising the coding sequence for the AAD1 protein (U.S. Pat. No. 7,838,733) under the transcriptional control of the SCBV promoter as described above. Termination of transcription and polyadenylation of the aad1 mRNAs were determined by a maize lipase 3'UTR, essentially as disclosed as bases 921 to 1277 of GENBANK™ Accession No. gb|L35913.1|MZELIPASE and in U.S. Pat. No. 7,179,902. The resulting hpRNA binary expression vectors were named pDAB109817 (for Caf-180 v3), pDAB109815 (for VatpaseC v3), pDAB109816 (for VatpaseH v1) and pDAB109821 (for Rho1 v1).

For transformation of maize, the hpRNA binary expression vectors were introduced into disarmed *Agrobacterium tumefaciens* strain DAt13192, as described in PCT International Application No. PCT/US11/046,028 filed Jul. 29, 2011, which is hereby incorporated herein in its entirety.

Example 5

Screening of Candidate Target Genes

Synthetic dsRNA designed to inhibit some, but not all, target gene sequences identified in Example 2 caused mortality and growth inhibition when administered to WCR in diet-based assays. Caf1-180; VatpaseC; VatpaseH; and Rho1 were observed to exhibit greatly increased efficacy in this assay over other dsRNAs screened.

Figure 2:
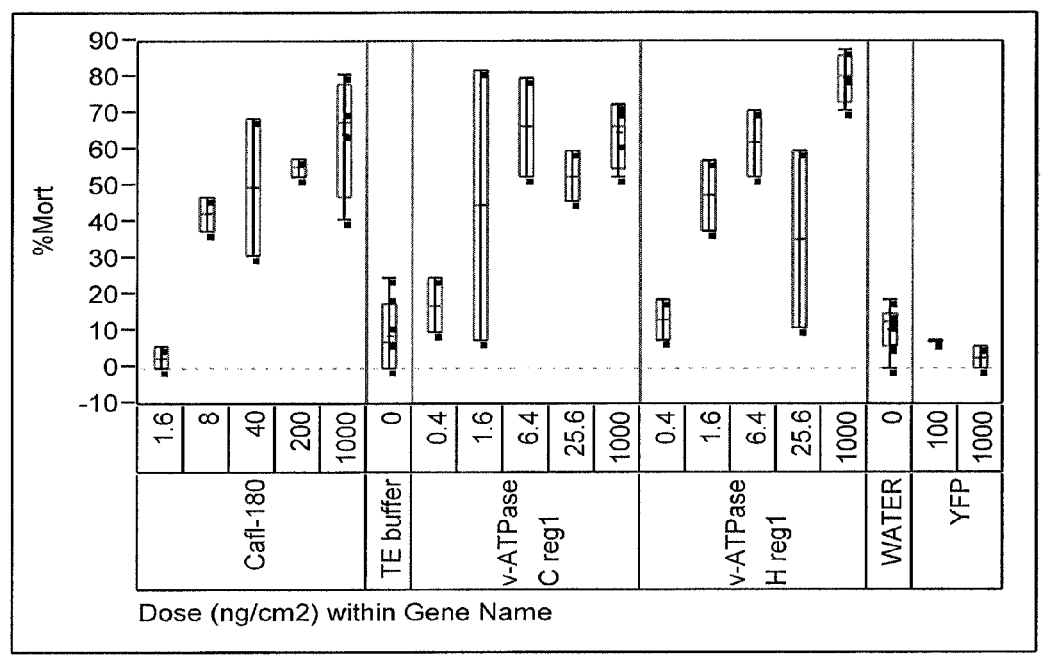
FIG. 2 includes a variability chart for the growth inhibition of coleopteran pests treated with exemplary nucleic acid molecules.
Figure 3:
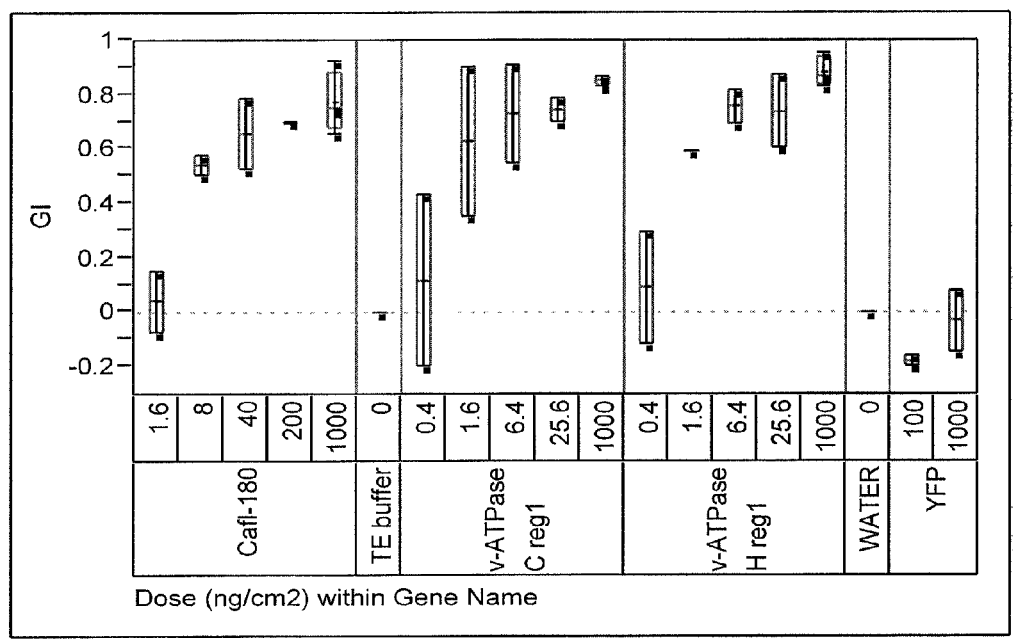
FIG. 3 includes a variability chart for the mortality of coleopteran pests treated with exemplary nucleic acid molecules.
Figure 4:
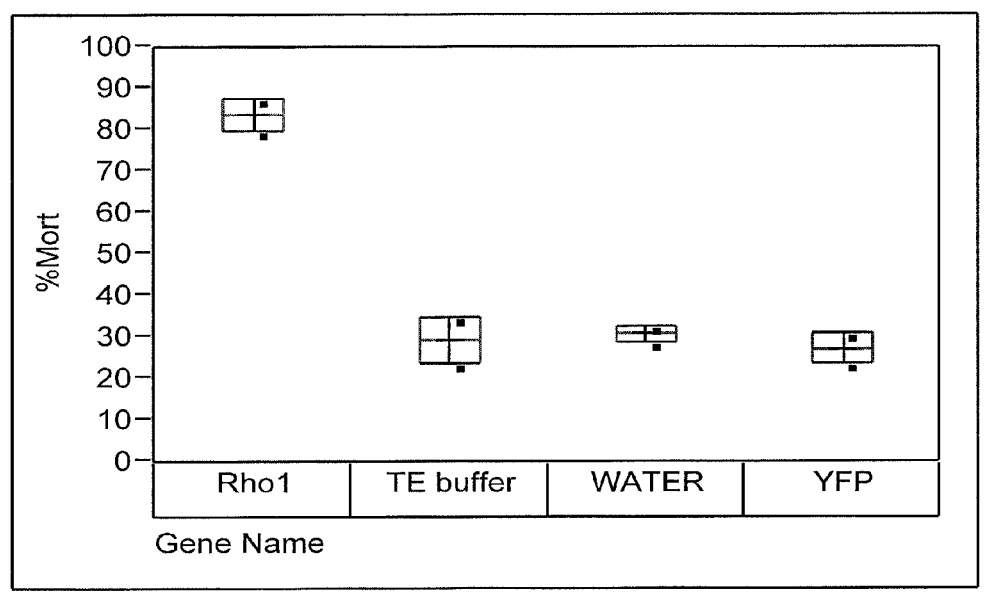
FIG. 4 includes a further variability chart for the growth inhibition of coleopteran pests treated with exemplary nucleic acid molecules.

Replicated bioassays demonstrated that ingestion of constructs transcribed into Caf1-180 (SEQ ID NO:110) dsRNA; VatpaseC region 1 (SEQ ID NO:111) dsRNA; VatpaseC region 1 short (SEQ ID NO:112) dsRNA; VatpaseC region 2 (SEQ ID NO:113) dsRNA; VatpaseH region 1 (SEQ ID NO:114) dsRNA; VatpaseH region 2 (SEQ ID NO:115) dsRNA; and Rho1 (SEQ ID NO:116) dsRNA each resulted in surprisingly robust mortality and growth inhibition of western corn rootworm larvae. Tables 3 and 4 show the results of diet-based feeding bioassays of WCR larvae following 9-day exposure to these dsRNAs. FIGS. 2-4 show variability charts for the mortality and growth inhibition of coleopteran pests treated with exemplary nucleic acid molecules.

TABLE 3

Results of western corn rootworm diet-feeding bioassays (after 9 days of feeding).

| Sample Name | $LC_{50}$ | $LC_{50}$ Range | $LC_{80}$ | $LC_{80}$ Range | $GI_{50}$ | $GI_{50}$ Range | $GI_{80}$ | $GI_{80}$ Range |
|---|---|---|---|---|---|---|---|---|
| Caf1-180 | 106* | 38-308 | ND** | ND | 22 | 6-79 | 558 | 72-1000+ |
| VatpaseC region 1 | 9 | 0.14-83 | ND | ND | 1.8 | 0.4-9.3 | 20 | 1.2-344 |
| VatpaseC region 1 short | 13.4 | 3.6-45 | ND | ND | <1.0 | | 33 | 2-250+ |
| VatpaseC region 2 | 2.7 | 0.18-11.5 | >1000 | ND | 5.1 | 0.4-68.4 | 87 | 0.53-1000+ |
| VatpaseH region 1 | 2 | 0.5-4.6 | 357 | 91-1000+ | 1.7 | 0.9-3.0 | 11 | 4.0-30 |
| VatpaseH region 2 | 0.70 | 0.04-2.83 | 168 | 40-10000 | 3.2 | 1.3-7.7 | 13.9 | 2.6-72.7 |

*Dose units are ng/cm$^2$
**ND = not determined

TABLE 4

Results of western corn rootworm diet-feeding bioassays (after 9 days of feeding).

| Sample Name | Dose (ng/cm$^2$) | Mean % Mortality | Mean GI |
|---|---|---|---|
| Rho1 | 1000 | 84* | 0.824 |
| TE buffer | 0 | 29.5 | 0 |
| Water | 0 | 31 | 0 |

| | $LC_{50}$ | $LC_{50}$ Range | $GI_{50}$ |
|---|---|---|---|
| Rho1 | 302 | 92-1000+ | <4.0 |

*Rho1 mortality counts significantly different from TE buffer or Water counts (Likelihood ratio P < 0.0001)

It has previously been suggested that certain genes of *Diabrotica* spp. may be exploited for RNAi-mediated insect control. See U.S. Patent Publication No. 2007/0124836, which discloses 906 sequences, and U.S. Pat. No. 7,614,924, which discloses 9,112 sequences. However, it was determined that many genes suggested to have utility for RNAi-mediated insect control are not efficacious in controlling *Diabrotica*. It was also determined that Caf1-180, VatpaseC, VatpaseH, and Rho1 each provide surprising and unexpected superior control of *Diabrotica*, compared to other genes suggested to have utility for RNAi-mediated insect control.

Annexin, beta spectrin 2, and mtRP-L4 were each suggested in U.S. Pat. No. 7,614,924 to be efficacious in RNAi-mediated insect control. SEQ ID NO:51 is the DNA sequence of Annexin region 1, and SEQ ID NO:52 is the DNA sequence of Annexin region 2. SEQ ID NO:53 is the DNA sequence of beta spectrin 2 region 1, and SEQ ID NO:54 is the DNA sequence of beta spectrin 2 region 2. SEQ ID NO:55 is the DNA sequence of mtRP-L4 region 1, and SEQ ID NO:56 is the DNA sequence of mtRP-L4 region 2. A YFP sequence (SEQ ID NO:57) was also used to produce dsRNA as a negative control.

Each of these sequences was used to produce dsRNA by the methods of Example 4, and the dsRNAs were each tested by the same diet-based bioassay methods described above. Table 5 lists the sequences of the primers used to produce the annexin, beta spectrin 2, and mtRP-L4 dsRNA molecules. Table 6 presents the results of diet-based feeding bioassays of WCR larvae following 9-day exposure to these dsRNA molecules. Replicated bioassays demonstrated that ingestion of these dsRNAs resulted in no mortality or growth inhibition of western corn rootworm larvae above that seen with control samples of TE buffer, YFP, or water.

TABLE 5

Sequences and pairings of primers used to amplify gene regions of annexin, beta spectrin 2, mtRP-L4, and YFP for dsRNA synthesis.

| | Gene (Region) | Primer ID | SEQ ID NO: | Sequence |
|---|---|---|---|---|
| Pair 20 | Annexin (1) | Ann-F1T7 | SEQ ID NO: 58 | TTAATACGACTCACTATAGGGAGAGCTCCAACAGTGGTTCCTTATC |
| | Annexin (1) | Ann-R1 | SEQ ID NO: 59 | CTAATAATTCTTTTTTAATGTTCCTGAGG |
| Pair 21 | Annexin (1) | Ann-F1 | SEQ ID NO: 60 | GCTCCAACAGTGGTTCCTTATC |
| | Annexin (1) | Ann-R1T7 | SEQ ID NO: 61 | TTAATACGACTCACTATAGGGAGACTAATAATTCTTTTTTAATGTTCCTGAGG |
| Pair 22 | Annexin (2) | Ann-F2T7 | SEQ ID NO: 62 | TTAATACGACTCACTATAGGGAGATTGTTACAAGCTGGAGAACTTCTC |
| | Annexin (2) | Ann-R2 | SEQ ID NO: 63 | CTTAACCAACAACGGCTAATAAGG |
| Pair 23 | Annexin (2) | Ann-F2 | SEQ ID NO: 64 | TTGTTACAAGCTGGAGAACTTCTC |
| | Annexin (2) | Ann-R2T7 | SEQ ID NO: 65 | TTAATACGACTCACTATAGGGAGACTTAACCAACAACGGCTAATAAGG |
| Pair 24 | B-spect2 (1) | Betasp2-F1T7 | SEQ ID NO: 66 | TTAATACGACTCACTATAGGGAGAAGATGTTGGCTGCATCTAGAGAA |
| | B-spect2 (1) | Betasp2-R1 | SEQ ID NO: 67 | GTCCATTCGTCCATCCACTGCA |
| Pair 25 | B-spect2 (1) | Betasp2-F1 | SEQ ID NO: 68 | AGATGTTGGCTGCATCTAGAGAA |
| | B-spect2 (1) | Betasp2-R1T7 | SEQ ID NO: 69 | TTAATACGACTCACTATAGGGAGAGTCCATTCGTCCATCCACTGCA |
| Pair 26 | B-spect2 (2) | Betasp2-F2T7 | SEQ ID NO: 70 | TTAATACGACTCACTATAGGGAGAGCAGATGAACACCAGCGAGAAA |
| | B-spect2 (2) | Betasp2-R2 | SEQ ID NO: 71 | CTGGGCAGCTTCTTGTTTCCTC |
| Pair 27 | B-spect2 (2) | Betasp2-F2 | SEQ ID NO: 72 | GCAGATGAACACCAGCGAGAAA |
| | B-spect2 (2) | Betasp2-R2T7 | SEQ ID NO: 73 | TTAATACGACTCACTATAGGGAGACTGGGCAGCTTCTTGTTTCCTC |
| Pair 28 | mtRP-L4 (1) | L4-F1T7 | SEQ ID NO: 74 | TTAATACGACTCACTATAGGGAGAAGTGAAATGTTAGCAAATATAACATCC |
| | mtRP-L4 (1) | L4-R1 | SEQ ID NO: 75 | ACCTCTCACTTCAAATCTTGACTTTG |
| Pair 29 | mtRP-L4 (1) | L4-F1 | SEQ ID NO: 76 | AGTGAAATGTTAGCAAATATAACATCC |
| | mtRP-L4 (1) | L4-R1T7 | SEQ ID NO: 77 | TTAATACGACTCACTATAGGGAGAACCTCTCACTTCAAATCTTGACTTTG |
| Pair 30 | mtRP-L4 (2) | L4-F2T7 | SEQ ID NO: 78 | TTAATACGACTCACTATAGGGAGACAAAGTCAAGATTTGAAGTGAGAGGT |
| | mtRP-L4 (2) | L4-R2 | SEQ ID NO: 79 | CTACAAATAAAACAAGAAGGACCCC |
| Pair 31 | mtRP-L4 (2) | L4-F2 | SEQ ID NO: 80 | CAAAGTCAAGATTTGAAGTGAGAGGT |
| | mtRP-L4 (2) | L4-R2T7 | SEQ ID NO: 81 | TTAATACGACTCACTATAGGGAGACTACAAATAAAACAAGAAGGACCCC |
| Pair 32 | YFP | YFP-FT7 | SEQ ID NO: 82 | TTAATACGACTCACTATAGGGAGACACCATGGGCTCCAGCGGCGCCC |
| | YFP | YFP-R | SEQ ID NO: 83 | AGATCTTGAAGGCGCTCTTCAGG |

TABLE 5-continued

Sequences and pairings of primers used to amplify gene regions of annexin, beta spectrin 2, mtRP-L4, and YFP for dsRNA synthesis.

| | Gene (Region) | Primer ID | SEQ ID NO: | Sequence |
|---|---|---|---|---|
| Pair 33 | YFP | YFP-F | SEQ ID NO: 84 | CACCATGGGCTCCAGCGGCGCCC |
| | YFP | YFP-RT7 | SEQ ID NO: 85 | TTAATACGACTCACTATAGGGAGAAGATCT TGAAGGCGCTCTTCAGG |

TABLE 6

Results of western corn rootworm larvae dsRNA diet-feeding bioassays (after 9 days of feeding).

| GENE NAME | DOSE (NG/CM$^2$) | MEAN WEIGHT PER INSECT (MG) | MEAN % MORTALITY | MEAN GROWTH INHIBITION |
|---|---|---|---|---|
| Annexin-region 1 | 1000 | 0.545 | 0 | −0.262 |
| Annexin-region 2 | 1000 | 0.565 | 0 | −0.301 |
| Beta spectrin2 region 1 | 1000 | 0.340 | 12 | −0.014 |
| Beta spectrin2 region 2 | 1000 | 0.465 | 18 | −0.367 |
| mtRP-L4 region 1 | 1000 | 0.305 | 4 | −0.168 |
| mtRP-L4 region 2 | 1000 | 0.305 | 7 | −0.180 |
| TE buffer | 0 | 0.430 | 13 | 0.000 |
| Water | 0 | 0.535 | 12 | 0.000 |
| YFP | 1000 | 0.480 | 9 | −0.386 |

Example 6

Effects of Sequence Length on VatpaseC dsRNA Efficacy dsRNAs of vacuolar-ATPase subunit C (VatpaseC) ranging in size from 349 to 500 bp were active in diet feeding assays against western corn rootworm larvae. Table 3. To determine the length-dependence of the efficacy of dsRNA molecules, the lengths of Vatpase C dsRNAs were varied and tested. Sequences were chosen to represent the 5' terminal 15-, 25-, 50- and 100-bases, and the 3' terminal 100-, 50-, 25-, and 15-bases of a segment of 174 base pairs of the VatpaseC coding sequence (SEQ ID NO:2).

dsRNA fragments representing the 15-bp and 25-bp 5' and 3' VatpaseC sequences were synthesized by a commercial vendor (INTEGRATED DNA TECHNOLOGIES; Coralville, Iowa). Table 7. The 50-bp and 100-bp 5' and 3' dsRNA fragments, and the full length 174-bp dsRNA fragment, were generated from PCR-amplified DNA templates using T7 RNA polymerase following the instructions of a MEGAscript™ RNAi kit (AMBION®, Foster City, Calif.) using the primers listed in Table 8. The combinations of primers used to amplify the various lengths of DNA templates are listed in Table 9.

TABLE 7

Synthetic RNAs designed to serve as 15-bp and 25-bp (blunt-ended) VatpaseC dsRNAs.

| dsRNA Name | Sense strand sequence (5' to 3') | Sequence identifier |
|---|---|---|
| VatpaseC5'-15 | AUGACUGAGUAUUGG | SEQ ID NO: 117 |
| VatpaseC5'-25 | AUGACUGAGUAUUGGUUGAUAUCUG | SEQ ID NO: 118 |
| VatpaseC3'-15 | CUUUCUGAUGAUCUG | SEQ ID NO: 119 |
| VatpaseC3'-25 | GUUAGUAGGACUUUCUGAUGAUCUG | SEQ ID NO: 120 |

TABLE 8

PCR primers used to generate various lengths of VatpaseC DNA templates comprising a T7 promoter sequence (underlined) for dsRNA synthesis.

| Primer Name | Primer Sequence | SEQ ID NO. | Strand |
|---|---|---|---|
| VatpaseC-FT7 | TTAATACGACTCACTATAGGGAGAATGACTG AGTATTGGTTGATATCTGC | SEQ ID NO: 121 | sense |
| VatpaseC-R50T7 | TTAATACGACTCACTATAGGGAGATGTTGAC AGGTCTTATCCCCT | SEQ ID NO: 122 | antisense |
| VatpaseC-R100T7 | TTAATACGACTCACTATAGGGAGATTGACAA ATTATTCTGTTTACTTGTCATAT | SEQ ID NO: 123 | antisense |
| VatpaseC-RT7 | TTAATACGACTCACTATAGGGAGACAGATCA TCAGAAAGTCCTACTAACTG | SEQ ID NO: 124 | antisense |
| VatpaseC-F50T7 | TTAATACGACTCACTATAGGGAGAGACTTGA AAGTTGGTACTCTGGAT | SEQ ID NO: 125 | sense |

TABLE 8-continued

PCR primers used to generate various lengths of VatpaseC DNA templates comprising a T7 promoter sequence (underlined) for dsRNA synthesis.

| Primer Name | Primer Sequence | SEQ ID NO. | Strand |
|---|---|---|---|
| VatpaseC-F100T7 | <u>TTAATACGACTCACTATAGGGAGA</u>GACAAGT AAACAGAATAATTTGTCAACC | SEQ ID NO: 126 | sense |

TABLE 9

Primer combinations used in PCR to generate VatpaseC DNA templates for synthesis of various lengths of dsRNA.

| dsRNA Name | Primer Pair | Amplicon Length (bp)* | dsRNA Length (bp)** | Starting point for length |
|---|---|---|---|---|
| VatpaseC5'-50 | VatpaseC-FT7 & VatpaseC-R50T7 | 50 + 48 = 98 | 50 + 12 = 62 | 5' end |
| VatpaseC5'-100 | VatpaseC-FT7 & VatpaseC-R100T7 | 100 + 48 = 148 | 100 + 12 = 112 | 5' end |
| VatpaseC-174 | VatpaseC-FT7 & VatpaseC-RT7 | 174 + 48 = 222 | 174 + 12 = 186 | 5' end |
| VatpaseC3'-50 | VatpaseC-F50T7 & VatpaseC-RT7 | 51 + 48 = 99 | 51 + 12 = 63 | 3' end |
| VatpaseC3'-100 | VatpaseC-F100T7 & atpaseC-RT7 | 100 + 48 = 148 | 100 + 12 = 112 | 3' end |

*T7 promoter sequence (24 bp) added at the 5' end of both primers, resulting in the addition of 48-bp to the amplicons.
**GGGAGA from the T7 promoter sequence is added at the 5' end of both strands of dsRNA during transcription, resulting in the addition of 12-bp to the transcripts.

VatpaseC dsRNAs (i.e., VatpaseC 5'-15, VatpaseC 5'-25, VatpaseC 5'-50, VatpaseC 5'-100, VatpaseC 3'-15, VatpaseC 3'-25, VatpaseC 3'-50, VatpaseC 3'-100, and VatpaseC-174) were each tested at a single dose (1000 ng/cm$^2$) for activity (lethality) using diet feeding assays with western corn rootworm larvae. As shown in Table 10, activities of these dsRNA samples (as measured by percent larval mortality on day 9 of feeding) are different. Feeding of the 15-bp and 25-bp VatpaseC dsRNA samples (both 5' and 3') did not induce significant larval mortality, which is a result similar to the negative control using YFP dsRNA. However, both 5'- and 3'-VaptaseC dsRNAs of 100 bp, and 5'- and 3'-VaptaseC dsRNAs of 174 bp, resulted in similarly unexpected high larval mortality. The two 50-bp dsRNA samples showed different results in the feeding assays; the VatpaseC5'-50 dsRNA sample did not result in significant larval mortality, but showed significant stunting, whereas the VaptaseC3'-50 dsRNA sample caused almost 60% mortality, which is a level almost as high as the values obtained with the samples of 100-bp and 174-bp dsRNAs. Table 10.

Further, the activities of the VatpaseC dsRNAs were determined at six test doses (1.0, 3.9, 62.5, 250, and 1000 ng/cm$^2$) to obtain relative $LC_{50}$ and $GI_{50}$ values. Table 11. The $LC_{50}$ value obtained with the VatpaseC 3'-100 sample was 3.01 ng/cm$^2$, which was the lowest value observed (i.e., the highest potency). Of particular note is the $LC_{50}$ value of 9.81 ng/cm$^2$ obtained with the VatpaseC-174 sample. The construct designed to produce a VatpaseC v4 hairpin in corn plants showed activity when tested with greenhouse-grown plants. Example 10; Table 18. That VaptaseC v4 sequence fragment (166 bp) is nearly identical to the VatpaseC-174 sequence described here; the VatpaseC-174 sequence described here lacks only 8 bp (ATGACTGA) at the 5' end of the 166 bp VaptaseC v4 sequence fragment.

TABLE 10

Results of western corn rootworm larvae dsRNA diet-feeding bioassays (after 9 days of feeding) utilizing different lengths of VatpaseC dsRNA at 1000 ng/cm$^2$.

| Sample | Replicates | Mean % Mortality | Mean % Growth Inhibition (GI) |
|---|---|---|---|
| VatpaseC 3'-15 | 4 | 12.33 B* | 10.28 BC** |
| VatpaseC 3'-25 | 4 | 6.07 B | −28.85 C |
| VatpaseC 3'-50 | 4 | 59.38 A | 83.60 A |
| VatpaseC 3'-100 | 4 | 69.76 A | 84.43 A |
| VatpaseC-174 | 2 | 67.65 A | 84.70 A |
| VatpaseC 5'-15 | 4 | 2.94 B | 11.50 BC |
| VatpaseC 5'-25 | 4 | 5.00 B | 6.90 BC |
| VatpaseC 5'-50 | 4 | 19.12 B | 54.75 AB |
| VatpaseC 5'-100 | 4 | 73.53 A | 88.75 A |
| VatpaseC-174 | 4 | 71.60 A | 83.00 A |
| YFP (neg. control) | 6 | 10.12 B | 0.09 BC |

*Mean % mortality values followed by the same letter are not significantly different from one another at the P = 0.05 level (as calculated ANOVA/Tukey comparison of means). Mortality values for negative controls without dsRNA (TE buffer, and water) were less than 20% and are not shown.
**Mean % GI values followed by the same letter(s) are not significantly different from one another at the P = 0.05 (calculated by ANOVA/Tukey comparison of means). The larval weight of the negative control YFP dsRNA-fed larvae was used as the basis for the GI calculation.

TABLE 11

$LC_{50}$ and $GI_{50}$ values for different lengths of VatpaseC dsRNA provided at 1.0, 3.9, 62.5, 250, and 1000 ng/cm$^2$ to western corn rootworm larvae (after 9 days of feeding).

| Sample | Replicates | $LC_{50}$ (ng/cm$^2$) | $GI_{50}$ (ng/cm$^2$) |
|---|---|---|---|
| VatpaseC3'-50 | 4 | 144.88 | 9.56 |
| VatpaseC3'-100 | 4 | 3.01 | 0.25 |
| VatpaseC5'-100 | 4 | 17.49 | 0.85 |
| VatpaseC-174 | 4 | 9.81 | 0.23 |

Example 7

Effects of dsRNA Sequence Variation on VatpaseC dsRNA Efficacy dsRNA molecules that are not perfectly complementary to a target sequence (for example, having only 95% identity to the target mRNA) are effective to control coleopteran pests. Non-complementary bases were introduced into the sense strand or the antisense strand of VatpaseC dsRNAs, resulting in mismatches between the sense and antisense strands of the dsRNA (and consequently, resulting in mismatches between the dsRNA and the in vivo target mRNA). The effects on the insecticidal activity of the imperfectly matched dsRNAs against western corn rootworm larvae were measured in diet bioassays.

Only one of the two DNA strands encoding a VatpaseC dsRNA was mutated at a time, and a single non-complementary nucleotide was artificially introduced at each mutation site. The mutation sites were arbitrarily positioned at 20 nucleotide intervals along the entire length of the mutated strand of a DNA encoding a VatpaseC dsRNA. The identity of the nucleotide chosen to replace the native one was made from the proximal nucleotides on either side of the mutation site that did not complement the nucleotide on the non-mutated strand opposite the mutation site. In the event that three or more nucleotides were the same in a given location, the nearest different nucleotide was selected to replace the native one.

Two imperfectly complementary, substantially homologous VatpaseC (v4) dsRNAs v4.1 and v4.2) were designed, generated, and tested for insecticidal activity. Both dsRNAs comprised 166 bp of a VatpaseC v4 sequence, plus six nucleotides (GGGAGA) on the 5' end of each RNA strand that are artifacts of transcription by the T7 promoter. Thus, the total length of each dsRNA was 178 bp.

The VatpaseC v4.1 substantially homologous dsRNA was designed and generated with non-complementary bases introduced into the antisense strand. This dsRNA was achieved by the following steps: (1) An antisense strand sequence was designed to have a mutation introduced at every 20 nucleotides; (2) DNA fragments comprising the mutated antisense strand DNA sequence or a native sense strand DNA sequence (i.e., without mutations) were chemically synthesized (IDT); (3) DNA oligonucleotides comprising the mutated antisense strand and oligonucleotides comprising the sense strand were annealed to form double-stranded molecules; (3) PCR amplification employing primers comprising 5' terminal T7 promoter sequences was used to incorporate the T7 promoter sequence into the 5' ends of both strands, thereby providing a sufficient template for dsRNA synthesis; and (4) dsRNA synthesis was accomplished using T7 RNA polymerase and an AMBION® MEGAscript™ RNAi kit, according to the supplier's instructions.

The VatpaseC v4.2 substantially homologous dsRNA, having mutations introduced at intervals of 20 bases in the sense strand sequence (but having a native antisense strand sequence), was obtained by appropriate modifications of the above methods. Further, a VatpaseC v4 dsRNA comprising the native sequence (i.e., having perfectly complementary sense and antisense strands) was constructed, and used as a control for efficacy comparison with the VatpaseC v4.1 and v4.2 substantially homologous dsRNAs in diet-based feeding assays against western corn rootworm larvae (conducted using previously described methods).

Seven doses of these dsRNAs (0.2, 1.0, 3.9, 15.6, 62.5, 250, and 1000 ng/cm$^2$) were tested in feeding bioassays with western corn rootworm first-instar larvae to obtain $LC_{50}$ and $GI_{50}$ values. The assays were independently conducted two times, and each experiment had two replicates.

The $LC_{50}$ calculated for the substantially homologous VatpaseC v4.1 (antisense strand mismatched) dsRNA was 780.9 ng/cm$^2$, which is 7.9-fold higher than the $LC_{50}$ obtained for the native (i.e., non-mutated) VatpaseC v4 dsRNA. Table 12. This result indicates that, even though the 178 base antisense strand of the VatpaseC v4.1 dsRNA contained 8 mutated bases, sufficient homology to the coleopteran pest target mRNA strand existed to induce a lethal effect following ingestion of the dsRNA. The $LC_{50}$ value calculated for the substantially homologous VatpaseC v4.2 (sense strand mismatched) dsRNA was 868.6 ng/cm$^2$, which is similar to the value obtained with VatpaseC v4.1, and 8.8 fold higher than that obtained in these assays for the VatpaseC v4 dsRNA. These results demonstrate that substantially homologous dsRNAs comprising mismatches in the sense strand of the dsRNA retain sufficient homology to a coleopteran pest target mRNA strand to induce a lethal effect following ingestion of the dsRNA. It was further found that in these feeding assays the VatpaseC v4.1 and v4.2 dsRNAs had $GI_{50}$ values that were higher than the value calculated for the native (i.e., non-mutated) VatpaseC v4 dsRNA. Table 12. It is therefore seen that VatpaseC v4.1 and 4.2 dsRNAs are able induce both improved growth inhibition and improved mortality upon ingestion by a coleopteran pest.

TABLE 12

Insecticidal activity of substantially homologous VatpaseC dsRNAs (v4.1 and v4.2), and native VatpaseC v4 dsRNA against western corn rootworm larvae.

| dsRNA | Replicates | $LC_{50}$ (ng/cm$^2$) | $LC_{50}$ Increase (fold) | $GI_{50}$ (ng/cm$^2$) | $GI_{50}$ Increase (fold) |
|---|---|---|---|---|---|
| VatpaseC v4 | 8 | 98.5 | NA | 0.16 | NA |
| VatpaseC v4.1 | 4 | 780.9 | 7.9 | 7.50 | 47.7 |
| VatpaseC v4.2 | 4 | 868.6 | 8.8 | 0.84 | 5.4 |

Example 8

*Agrobacterium*-Mediated Production of Transgenic Maize Tissues Comprising Insecticidal Hairpin dsRNAs Ear Sterilization and Embryo Isolation:

Immature maize embryos were obtained from plants of *Zea mays* inbred line B104 grown in the greenhouse and self- or sib-pollinated to produce ears. The ears were harvested approximately 9 to 12 days post-pollination. On the experimental day, ears were surface-sterilized by immersion in a 20% solution of sodium hypochlorite (6.15%), and shaken for 20 to 30 min, followed by three rinses in sterile water. After sterilization, immature zygotic embryos (1.5 to 2.4 mm) were aseptically dissected from each ear, and randomly distributed into microcentrifuge tubes containing liquid Inoculation Medium (2.2 gm/L MS salts (Frame et al., 2011, supra); 1×ISU Modified MS Vitamins (Frame et al. (2011) "Genetic Transformation Using Maize Immature Zygotic Embryos," IN *Plant Embryo Culture Methods and Protocols: Methods in Molecular Biology*. T. A. Thorpe and E. C. Yeung, (Eds.), SPRINGER SCIENCE AND BUSINESS MEDIA, LLC., pp 327-341); 68.4 gm/L sucrose; 36 gm/L glucose; 115 mg/L L-proline; 100 mg/L myo-inositol; and 200 μM acetosyringone (prepared in DMSO); at pH 5.4). For a given set of experiments, embryos from pooled ears were used for each transformation.

*Agrobacterium* Culture Initiation:

Glycerol stocks of *Agrobacterium* strain DAt13192 containing the binary transformation vectors described above in Example 4 were streaked on AB minimal medium plates (Watson et al. (1975) J. Bacteriol. 123:255-64) containing appropriate antibiotics, and were grown at 20° C. for 3 to 4 days. A single colony was picked from each plate, streaked onto YEP plates (10 gm/L yeast extract; 10 gm/L Peptone; and 5 gm/L NaCl) containing the appropriate antibiotics, and incubated at 20° C. for 1-2 days.

*Agrobacterium* Culture and Co-cultivation.

*Agrobacterium* colonies were taken from a YEP plate, suspended in 10 mL of Inoculation Medium in a 50 mL disposable tube, and the cell density was adjusted to an $OD_{550}$ (Optical Density measured at 550 nm) of from 0.2 to 0.4 using a spectrophotometer. The *Agrobacterium* cultures were incubated on a rotary shaker at 125 rpm (room temperature) while embryo dissection was performed. Immature zygotic embryos (previously isolated from the sterilized maize kernels and placed in 1 mL of Inoculation Medium) were washed once in Inoculation Medium. 2 mL *Agrobacterium* suspension was added to each tube of embryos, and the tubes were placed on a shaker platform for between 10 and 15 minutes. The embryos were transferred onto Co-cultivation Medium (4.33 gm/L MS salts; 1×ISU Modified MS Vitamins; 30 gm/L sucrose; 700 mg/L L-proline; 3.3 mg/L Dicamba (3,6-dichloro-o-anisic acid or 3,6-dichloro-2-methoxybenzoic acid) in KOH; 100 mg/L myo-inositol; 100 mg/L Casein Enzymatic Hydrolysate; 15 mg/L AgNO$_3$; 100 µM acetosyringone in DMSO; and 3 gm/L GELZAN™ (SIGMA-ALDRICH®); at pH 5.8), oriented with the scutellum facing up, and incubated at 25° C., under 24-hour light at 50 µEm$^{-2}$ sec$^{-1}$ light intensity for 3 days.

Callus Selection and Regeneration of Putative Events:

Following the co-cultivation period, embryos were transferred to Resting Medium (4.33 gm/L MS salts; 1×ISU Modified MS Vitamins; 30 gm/L sucrose; 700 mg/L L-proline; 3.3 mg/L Dicamba in KOH; 100 mg/L myo-inositol; 100 mg/L Casein Enzymatic Hydrolysate; 15 mg/L AgNO$_3$; 0.5 gm/L MES (2-(N-morpholino)ethanesulfonic acid monohydrate; PHYTOTECHNOLOGIES LABORATORIES®, Lenexa, Kans.); 250 mg/L Carbenicillin; and 2.3 gm/L GELZAN™; at pH 5.8), and incubated under 24-hour light at 50 µEm$^{-2}$ sec$^{-1}$ light intensity and at 25° C. for 3 days.

Embryos were transferred onto Selection Medium 1 (which consists of the Resting Medium (above) with 100 nM R-Haloxyfop acid (0.0362 mg/L)), and incubated in the dark or under 24-hour light at 50 µm$^{-2}$ sec$^{-1}$ light intensity for 7 to 14 days at 28° C. Proliferating embryogenic calli were transferred onto Selection Medium 2 (which consists of Resting Medium (above), with 500 nM R-Haloxyfop acid (0.1810 mg/L)), and were incubated in 24-hour light at 50 µm$^{-2}$ sec$^{-1}$ light intensity for 14 to 21 days at 28° C. This selection step allowed transgenic callus to further proliferate and differentiate.

Proliferating, embryogenic calli were transferred onto Pre-Regeneration Medium (4.33 gm/L MS salts; 1×ISU Modified MS Vitamins; 45 gm/L sucrose; 350 mg/L L-proline; 100 mg/L myo-inositol; 50 mg/L Casein Enzymatic Hydrolysate; 1.0 mg/L AgNO$_3$; 0.25 gm/L MES; 0.5 mg/L naphthaleneacetic acid in NaOH; 2.5 mg/L abscisic acid in ethanol; 1 mg/L 6-benzylaminopurine; 250 mg/L Carbenicillin; 2.5 gm/L GELZAN™; and 500 nM R-Haloxyfop acid; at pH 5.8), and cultured under 24-hour light at 50 µEm$^{-2}$ sec$^{-1}$ light intensity for 7 days at 28° C.

Embryogenic calli with shoot-like buds were transferred onto Regeneration Medium I (4.33 gm/L MS salts; 1×ISU Modified MS Vitamins; 60 gm/L sucrose; 100 mg/L myo-inositol; 125 mg/L Carbenicillin; 3.0 gm/L GELZAN™; and 500 nM R-Haloxyfop acid; at pH 5.8), and cultured under 24-hour light at 50 µm$^{-2}$ sec$^{-1}$ light intensity for 7 days.

Small shoots with primary roots were transferred to Shoot/Root medium (4.33 gm/L MS salts; 1×ISU Modified MS Vitamins; 30 gm/L sucrose; 100 mg/L myo-inositol; 3.5 gm/L GELZAN™; at pH 5.8) in PHYTATRAYS™ (PHYTOTECHNOLOGIES LABORATORIES®), and were incubated under 16:8 hr. light:dark at from 140 to 190 µEm$^{-2}$ sec$^{-1}$ light intensity for 7 days at 27° C. Putative transgenic plantlets were analyzed for transgene copy number, and transferred to soil.

Seed Production:

Plants were transplanted into METRO-MIX™ 360 soilless growing medium (SUN GRO HORTICULTURE; Bellevue, Wash.), and hardened-off in a growth room. Plants were then transplanted into SUNSHINE CUSTOM BLEND™ 160 soil mixture, and grown to flowering in the greenhouse. Controlled pollinations for seed production were conducted.

Western corn rootworm bioassays on greenhouse-grown plants were conducted by the methods described in Example 12. Plants with a root rating of 0.75 or better were transplanted immediately to 5-gallon pots for seed production. Transplants were treated with insecticide to prevent further rootworm damage and insect release in the greenhouses. B104 plants were outcrossed to non-transgenic B104 (pollen donor) plants for seed production. Seeds produced by these plants are saved for evaluation at the $T_1$ and subsequent generations of plants.

*Agrobacterium* strain DAt13192 comprising a plant-expressible construct encoding a Caf1-180 v3 hairpin dsRNA (Example 4; construct in plasmid pDAB109817) was used to produce B104 transgenic maize plants. Western corn rootworm bioassays on these greenhouse-grown transgenic plants were conducted by the methods described in Example 12. Plants transformed with a similar plasmid (pDAB101556), which contains a gene for YFP production but does not contain a gene for dsRNA production, were used as negative controls. The results of these bioassays are shown in Table 13.

TABLE 13

Results of western corn rootworm bioassays of B104 transgenic maize events expressing a Caf1-180 v3 hairpin dsRNA.

| Event Description | Total No. Plants Tested | No. of Plants with Root Rating ≤0.5 (%)* | No. of Plants with Root Rating ≤0.75 (%) |
|---|---|---|---|
| Caf1-180 v3 hp dsRNA (pDAB109817) | 16 | 1 (6.3) | 4 (25) |
| YFP (pDAB101556) | 14 | 1 (7.1) | 1 (7.1) |
| B104 non-transgenic | 16 | 2 (12.5) | 3 (18.8) |

*Maize root damage rating scale: 0-1.0

*Agrobacterium* strain DAt13192 comprising a plant-expressible construct encoding a VatpaseC v3 hairpin dsRNA (Example 4; construct in plasmid pDAB109815) was used to produce B104 transgenic maize plants. Western corn rootworm bioassays on these greenhouse-grown transgenic plants were conducted by methods described in Example 12.

Plants transformed with a similar plasmid (pDAB101556), which contains a gene for YFP production but does not contain a gene for dsRNA production, were used as negative controls. The results of these bioassays are shown in Table 14.

TABLE 14

Results of western corn rootworm bioassays of B104 transgenic maize events expressing aVatpaseC v3 hairpin dsRNA.

| Event Description | Total No. Plants Tested | No. of Plants with Root Rating ≤0.5 (%)* | No. of Plants with Root Rating ≤0.75 (%) |
|---|---|---|---|
| VatpaseC v3 Hp dsRNA (pDAB109815) | 10 | 6 (60) | 7 (70) |
| YFP (pDAB101556) | 14 | 1 (7.1) | 1 (7.1) |
| B104 non-transgenic | 16 | 2 (12.5) | 3 (18.8) |

*Maize root damage rating scale: 0-1.0

*Agrobacterium* strain DAt13192 comprising a plant-expressible construct encoding a VatpaseH v 1 hairpin dsRNA (Example 4; construct in plasmid pDAB109816) was used to produce B104 transgenic maize plants. Western corn rootworm bioassays on these greenhouse-grown plants were conducted by methods described in Example 12. Plants transformed with a similar plasmid (pDAB101556), which contains a gene for YFP production but does not contain a gene for dsRNA production, were used as negative controls. The results of these bioassays are shown in Table 15.

TABLE 15

Results of western corn rootworm bioassays of B104 transgenic maize events expressing a VatpaseH v1 hairpin dsRNA.

| Event Description | Total No. Plants Tested | No. of Plants with Root Rating ≤0.5 (%)* | No. of Plants with Root Rating ≤0.75 (%) |
|---|---|---|---|
| VatpaseH v1 hp dsRNA (pDAB109816) | 18 | 8 (44.4) | 14 (77.8) |
| YFP (pDAB101556) | 14 | 1 (7.1) | 1 (7.1) |
| B104 non-transgenic | 16 | 2 (12.5) | 3 (18.8) |

*Maize root damage rating scale: 0-1.0

Example 9

WHISKERS-Mediated Production of Transgenic Maize Tissues Comprising Insecticidal Caf1-180 v3 Hairpin dsRNAs Plants that produce one or more insecticidal dsRNA molecules (for example, at least one dsRNA molecule including a dsRNA molecule targeting a gene comprising one of SEQ ID NOs:1-4) through expression of a chimeric gene stably-integrated into the plant genome were produced. DNA molecules for plant transformation were prepared as described in Example 4, and were delivered into maize cells in Hi-II suspension cell cultures via WHISKERS-mediated transformation (essentially as described in U.S. Pat. Nos. 5,302,523 and 5,464,765; U.S. Patent Publication No. 2008/0182332; and Petolino and Arnold (2009) M. Paul Scott (ed.) *Methods in Molecular Biology Transgenic Maize*, Vol. 526, Humana Press, NY, pp 59-67), which are herein incorporated by this reference in their entirety.

Plant Cell Transformation and Selection:

All procedures for WHISKERS-mediated transformation were performed using standard aseptic techniques, and generally followed the methods described by Petolino and Arnold (2009), supra. *Zea mays* Hill embryogenic cell suspensions (Armstrong et al. (1991) Maize Genet. Coop. Newslett. 65:92-3) were subcultured by transferring 30 mL settled suspension cells, plus 70 mL conditioned medium (i.e., the medium in which the cells had been grown), into 200 mL of fresh H9CP (4.33 gm/L MS Basal Salts (PHYTOTECHNOLOGIES LABORATORIES, Cat # M524); 30.0 gm/L Sucrose; 100.0 mg/L Myo-inositol; 200 mg/L Casein Enzymatic Hydrolysate; 2.0 mg/L 2,4-Dichlorophenoxy acetic acid; 2.0 mg/L Naphthaleneacetic acid; 691 mg/L L-Proline; 2.0 mg/L Glycine; 0.5 mg/L Thiamine HCl; 0.5 mg/L Pyridoxine HCl; 0.05 mg/L Nicotinic acid; at pH6.0) media containing 5% coconut water (SIGMA ALDRICH, St. Louis, Mo.; Catalog No. C5915) into a 175 mL NALGENE™ disposable conical bottom centrifuge tube (THERMO FISHER SCIENTIFIC; Catalog No. 3145-0175). The diluted cells were then incubated in a sterile 1 L disposable cell culture flask in the dark at 28° C. on a gyro-rotary shaker with a one inch throw radius at 120 rpm, and the cells were subcultured every 3.5 days as described above.

One day following subculture, and 18 to 24 hr prior to the transfection procedure, 50 mL H9CP medium containing 30 mL settled cells was added to 150 mL fresh GN6 medium (3.99 gm/L Chu N6 Basal Salts with vitamins (PHYTOTECHNOLOGIES LABORATORIES, Cat # C167); 30 gm/L Sucrose; 100 mg/L Myo-Inositol; 2 mg/L 2,4-Dichlorophenoxy acetic acid; at pH6.0) in a sterile 1 L flask, and the culture was incubated on a gyro-rotary shaker as described above.

Following 18 to 24 hr of incubation in GN6 media, the entire cell suspension was transferred to a sterile 175 mL disposable conical bottom centrifuge tube, and the cells were allowed to settle for 1-3 min, yielding a cell volume of about 40 mL. The spent medium was carefully decanted, and residual liquid was removed by pipette to produce a moist cell mass. Cells were resuspended in about 180 mL of high osmotic medium (GN6-SM; GN6 medium supplemented with 45 gm/L sorbitol and 45 gm/L mannitol) in the centrifuge tube, and the culture was placed on a table top rocker shaker at room temperature (23° C. to 25° C.) for about 30 minutes, but not more than 45 minutes. Following the 30 minute osmotic treatment, the cells were allowed to settle in the centrifuge tube for 3-5 minutes. Then, the liquid was carefully removed down to the 50 mL mark of the centrifuge tube via pipette, taking caution not to disturb the cells.

For delivery of plasmid DNA to the maize suspension culture cells, 5 mL of a 5% w/w suspension of BIOGRADE™ SC-9 silicon carbide whiskers (ADVANCED COMPOSITE MATERIALS, Greer, S. C.; lot 981011-101) was prepared by adding an appropriate amount of GN6-SM medium to sterilized (autoclaved), dry whiskers. An appropriate amount of DNA of pDAB109830 (Example 4) was added to the centrifuge tube (typically 80 μg/50 mL suspension of 40 mL cells), the cap was sealed tightly, and the tube was gently swirled to mix the contents. The centrifuge tube was fastened securely in a commercial paint mixer (RED DEVIL™ Model 5400; Minneapolis, Minn.) modified to securely hold the tube, and shaken for 10-20 seconds. After dilution to reduce the osmolarity of the medium with about 150 mL fresh medium (GN6-SM:GN6; 2:1 v/v) to a final volume of about 200 mL, the cells were incubated on a table top rocker shaker at RT for about 1 hour.

The transfected cells were then transferred by pipette in aliquots of about 8.3 mL onto sterile 70 mm WHATMAN™ #4 filter paper (THERMO FISHER SCIENTIFIC), taking care to evenly distribute the cells on the filter paper. The filters were placed on GN6 agar medium in 100×20 mm plastic plates, and then incubated in plastic boxes in the dark at 28° C. for 7 days.

One week after transformation, the filter papers holding the cells were transferred to fresh plates of GN6-1H (GN6 medium supplemented with 2.5 gm/L GELZAN™) solid agar medium containing 1.0 mg/L BIALAPHOS in 100×20 mm plates, and incubated in the dark at 28° C. BIALAPHOS was provided as HERBIACE® (20% ai) (MEIJI SEIKA KAISHA LTD.; Tokyo, JP).

One week later, the cells were embedded in soft agar by scraping the cell contents of each filter paper into a 50 mL sterile disposable centrifuge tube containing 15 mL of GN6 soft agarose medium (GN6 medium with 7.0 gm/L SEAPLAQUE™ Agarose; LONZA, Rockland, Me.) at 37° C. to 40° C., shaking the capped tube vigorously, and then pouring the contents of the tube evenly onto four 100×25 mm plastic plates containing GN61H solid agar medium. Each plate was agitated to coat the surface with an even layer of the cell suspension, and upon solidification the plates were incubated at 28° C. in the dark.

Following six to 10 weeks of incubation, well-growing emerging colonies were transferred to fresh plates containing GN61H agar medium. These candidate transformed colonies were allowed to grow for 2-4 weeks on the selection medium to establish stable events having a mass of about 50 to 200 mg tissue, which were then subjected to molecular analysis.

Samples of 0.1 mL packed callus cells from candidate events were sampled and placed in 1.2 mL COSTAR™ polypropylene cluster tubes (CORNING, INC.; Corning N.Y.) and frozen at −80° C.

Molecular Analyses:

Callus cell events were analyzed for the relative expression of the full length transcript by real time quantitative PCR of the Per 5 3 UTR, and copy number was estimated by comparison to an internal maize gene (TIP41-like protein). RNA was isolated using the RNeasy™ 96 kit (QIAGEN, Valencia, Calif.). After the first wash (RW1), the columns were treated with QIAGEN RNase-free DNase in buffer "RDD" (according to the kit-suggested alternate protocol). First strand cDNA was prepared using a HIGH CAPACITY cDNA SYNTHESIS KIT (INVITROGEN) in a 10 µL reaction volume with 5 µL denatured RNA, substantially according to the manufacturer's recommended protocol. The protocol was modified slightly to include the addition of 10 µL 100 µM T20VN oligonucleotide (IDT) into the 1 mL tube of random primer stock mix, in order to prepare a working stock of combined random primers and oligo dT.

Following cDNA synthesis, samples were diluted 1:3 with nuclease-free water, and stored at −20° C. until assayed. Real-time PCR was performed on a LIGHTCYCLER™ 480 (ROCHE DIAGNOSTICS, Indianapolis, Ind.) in 10 µL reaction volume. All assays included negative controls of no-template (mix only). For the standard curves, a blank (water in source well) was also included in the source plate to check for sample cross-contamination. Reactions were run with the ROCHE UNIVERSAL PROBE™ at 0.5 µM and the primers for the target and reference genes at 10 µM. The primer sequences are set forth in Table 16. PCR reactions conditions were as follows: (1) Target activation at 95° C. for 10 min; (2) 43 cycles of (denature at 95° C. for 10 sec and extension at 60° C.); (3) acquire at 72° C. for 1 sec; and (4) cool at 40° C. for 10 sec.

TABLE 16

Primer sequences used for molecular analyses of transgenic maize.

| Primer | Target | SEQ ID NO. | Primer Sequence |
|---|---|---|---|
| MZTIPU67F | TIP41* | SEQ ID NO: 132 | AGCCAAGCCAGTGGTACTTC |
| MZTIPU67R | TIP41 | SEQ ID NO: 133 | TCGCAGACAAAGTAGCAAATGT |
| P5U76S (F) | Per5 3'UTR | SEQ ID NO: 134 | TTGTGATGTTGGTGGCGTAT |
| P5U76A (R) | Per5 3'UTR | SEQ ID NO: 135 | TGTTAAATAAAACCCCAAAGATCG |

*TIP41-like protein; maize homolog of AT4G34270 by tBLASTx (74% identity)

Data Analysis:

Data were analyzed using LIGHTCYCLER™ Software v1.5 by relative quantification using a second derivative max algorithm for calculation of Cq values according to the supplier's recommendations. For expression analyses, expression values were calculated using the ΔCt method (i.e., 2−(Cq TARGET−Cq REF)), which relies on the comparison of differences of Cq values between two targets, with the base value of 2 being selected under the assumption that, for optimized PCR reactions, the product doubles every cycle.

Transgenic Plant Regeneration:

Some stably-transformed events were regenerated into plants for in-planta insect bioassays.

Following the selection process, callus cultures were transferred to Pre-Regeneration 28 Medium (4.33 gm/L MS Basal Medium with Vitamins; 30.0 gm/L Sucrose; 5 mg/L 6-Benzylaminopurine; 25 µg/L 2,4-Dichlorphenoxyactetic acid; 2.5 gm/L GELZAN™; and 1.0 mg/L BIALAPHOS). Transferred callus cultures were incubated for 7 days at 28° C. under continuous white fluorescent light (approximately 50 µEm$^{-2}$ s$^{-1}$).

For regeneration, the cultures were transferred to Regeneration Medium 36 (4.33 gm/L MS Basal Medium with Vitamins; 30 gm/L Sucrose; 2.5 gm/L GELZAN™; and 1.0 mg/L BIALAPHOS), and plantlets were allowed to generate and grow at 28° C. under continuous white fluorescent light for up to 3 weeks. When plantlets reached a suitable growth stage, they were excised with a forceps and scalpel, transferred to a 20×100 mm test tube containing agar, and placed in the light for 2 days.

Transgenic plants were assigned unique identifiers, and transferred to a controlled environment chamber (~28° C. daytime temperature; 24° C. nighttime temperature; with a 16:8 supplemental lighting photoperiod). Transgenic plants were transplanted from tubes to 3.5 inch pots, and returned to the controlled environment chamber for 1-2 weeks to help acclimate the plants. Transgenic plants were then moved to the greenhouse, and transplanted from the small pots to ROOTRAINERS™ (style TINUS™ 350-4; SPENCER-LEMAIRE INDUSTRIES; Acheson, Alberta, Canada), at one plant per event per ROOTRAINER™, for insect feeding bioassays. Approximately four days after transplanting to ROOTRAINERS™, the T$_0$ plants were ready for the insect feeding bioassay. Insect feeding bioassays were conducted by the methods described in Example 12.

The presence and expression of a transgene producing hairpin dsRNA results in a reduction in WCR root pruning, as was evident in those plants that exhibit high expression levels of the dsRNA transcript (as measured by relative PCR scoring of the Per5 3'UTR). The results of western corn rootworm bioassays on those events containing an RNAi hairpin comprising SEQ ID NO:97, and that have a relative expression level 16-fold higher than the internal TIP41-like reference gene, are shown in Table 17. The results indicate the surprising result that 36% of the transgenic RNAi plants demonstrated reduced WCR damage, as compared to only 3% of the non-transgenic control plants tested. Although the biological response is variable within the $T_0$ transgenic maize plants, the transgenic plants showed appreciable reduction of WCR pruning as compared to the non-transgenic control plants.

TABLE 17

Results of western corn rootworm bioassays of Hi-II transgenic maize events expressing a Caf1-180 hairpin dsRNA.

| Event | No. of Plants with Root Rating ≤0.75 | Total No. of Plants Per Event | % of Plants with Root Rating ≤0.75 |
|---|---|---|---|
| 109830[2]-001 | 4 | 9 | 44 |
| 109830[2]-002 | 1 | 4 | 25 |
| 109830[2]-004 | 4 | 7 | 57 |
| 109830[2]-025 | 0 | 7 | 0 |
| 109830[4]-005 | 3 | 6 | 50 |
| Total Transgenics | 12 | 33 | 36 |
| Hi-II Control Plants | 1 | 30 | 3 |

Example 10

WHISKERS-Mediated Production of Transgenic Maize Tissues Comprising Insecticidal VatpaseC v3 and VatpaseC v4 Hairpin dsRNAs The transformation methods described in Example 9 were used to provide Hill maize transgenic plants expressing VatpaseC v3 hairpin dsRNA or VatpaseC v4 hairpin dsRNA, by transformation with plasmids pDAB109828 and pDAB109838 (Example 4). Molecular screening was performed according to the screening methods described in Example 9, and western corn rootworm bioassays were performed according to the bioassay methods described in Example 12.

The presence and expression of a transgene producing hairpin dsRNA results in a reduction in WCR root pruning, as was evident in those plants that exhibit high expression levels of the dsRNA transcript (as measured by relative PCR scoring of the Per5 3'UTR). The results of western corn rootworm bioassays on those events containing an RNAi hairpin comprising SEQ ID NO:100 (VatpaseC v3) or SEQ ID NO:103 (VatpaseC v4), and that have a relative expression level 20-fold higher than the internal TIP41-like reference gene, are shown in Table 18. The results indicate the surprising result that 43% of transgenic RNAi plants demonstrated reduced WCR damage, as compared to 0% of the non-transgenic control plants tested. Although the biological response is variable within the $T_0$ transgenic maize plants, only the transgenic plants showed appreciable reduction of WCR pruning.

TABLE 18

Results of western corn rootworm bioassays of Hi-II transgenic maize events expressing a VatpaseC v3 or v4 hairpin dsRNA.

| Event | No. of Plants with Root Rating ≤0.5 | Total No. of Plants Per Event | % of Plants with Root Rating ≤0.5 |
|---|---|---|---|
| 109828[4]-011 | 5 | 10 | 50 |
| 109828[4]-016 | 1 | 5 | 20 |
| 109828[4]-006 | 2 | 6 | 33 |
| 109838[3]-003 | 2 | 2 | 100 |
| 109838[3]-002 | 5 | 10 | 50 |
| 109838[3]-001 | 2 | 2 | 100 |
| 109838[4]-020 | 1 | 5 | 20 |
| 109838[3]-006 | 0 | 2 | 0 |
| Total Transgenics | 18 | 42 | 43 |
| Hi-II Control Plants | 0 | 26 | 0 |

Example 11

WHISKERS-Mediated Production of Transgenic Maize Tissues Comprising Insecticidal VatpaseH v1 Hairpin dsRNAs The transformation methods described in Example 9 were used to provide Hill maize transgenic plants expressing VatpaseH v1 hairpin dsRNA, by transformation with plasmid pDAB109829 (Example 4). Molecular screening was performed according to the screening methods described in Example 9, and western corn rootworm bioassays were performed according to the bioassay methods described in Example 12.

The presence and expression of a transgene producing hairpin dsRNA results in a reduction in WCR root pruning, as was evident in those plants that exhibit high expression levels of the dsRNA transcript (as measured by relative PCR scoring of the Per5 3'UTR). The results of western corn rootworm bioassays on those events containing an RNAi hairpin comprising SEQ ID NO:106, and that have a relative expression level 18-fold higher than the internal TIP41-like reference gene, are shown in Table 19. The results indicate the surprising result that 60% of transgenic RNAi plants demonstrated reduced WCR damage, as compared to 0% of the non-transgenic control plants tested. Although the biological response is variable within the $T_0$ transgenic maize plants, only the transgenic plants showed appreciable reduction of WCR pruning.

TABLE 19

Results of western corn rootworm bioassays of a Hi-II transgenic maize event expressing a VatpaseH hairpin dsRNA.

| Event | No. of Plants with Root Rating ≤0.5 | Total No. of Plants Per Event | % of Plants with Root Rating ≤0.5 |
|---|---|---|---|
| 109829[1]-005 | 3 | 5 | 60% |
| Hi-II Control Plants | 0 | 30 | 0% |

Example 12

Insect Bioassay of Transgenic Maize

Western corn rootworm (WCR, *Diabrotica virgifera virgifera* LeConte) eggs were received in soil from Crop Characteristics (Farmington, Minn.). The eggs were incubated at 28° C. for 10-11 days. Eggs were washed from the soil, placed into a 0.15% agar solution, and the concentration was adjusted to approximately 75-100 eggs per 0.25 mL aliquot. A hatch plate was prepared in a Petri dish with an aliquot of egg suspension to monitor hatch rates.

The soil around the maize plants was infested with 150-200 WCR eggs. The insects were allowed to feed for 2 weeks, after which time a "Root Rating" was given to each plant. A Node-Injury Scale was utilized for grading. Oleson et al. (2005) J. Econ. Entomol. 98(1):1-8.

Plants with a root rating of 0.75 or better were transplanted immediately to 5-gallon pots for seed production. Transplants were treated with insecticide to prevent further rootworm damage and insect release in the greenhouses. Hill plants were outcrossed to inbred maize line 5XH751 (pollen donor) for seed production. Seeds produced by these plants are saved for evaluation at the $T_1$ and subsequent generations of plants.

Example 13

Transgenic *Zea mays* Comprising Coleopteran Pest Sequences

Ten to 20 transgenic $T_0$ *Zea mays* plants are generated as described in Examples 8 and 9. A further 10-20 $T_1$ *Zea mays* independent lines expressing hairpin dsRNA for an RNAi construct as set forth in SEQ ID NOs:1-4 are obtained for corn rootworm challenge. These are confirmed through RT-PCR. Total RNA from selected independent $T_1$ lines are optionally used for RT-PCR with primers designed to bind in the pdk intron of the hairpin cassette in each of the RNAi constructs. In addition, specific primers for each target gene in a RNAi construct are optionally used to amplify and confirm the production of the pre-processed mRNA required for siRNA production in planta. The amplification of the desired bands for each target gene confirms the expression of the hairpin RNA in each transgenic *Zea mays*. Processing of the dsRNA hairpin of the target genes into siRNA is subsequently optionally confirmed in independent transgenic lines using RNA blot hybridizations.

Phenotypic Comparison of Transgenic RNAi Lines and Wild-Type *Zea mays*.

Target coleopteran pest genes or sequences selected for creating hairpin dsRNA have no similarity to any known plant gene or sequence. Hence it is not expected that the production or the activation of (systemic) RNAi by constructs targeting these genes or sequences will have any deleterious effect on transgenic plants. However, development and morphological characteristics of transgenic lines are compared with wild-type plants, as well as those of transgenic lines transformed with an empty hairpin vector. Plant root, shoot, foliage and reproduction characteristics are compared. There is no observable difference in root length and growth patterns of transgenic and wild-type plants. Plant shoot characteristics such as height, leaf numbers and sizes, time of flowering, floral size and appearance are similar. In general, there are no observable morphological differences between transgenic lines and those without expression of target iRNA molecules when cultured in vitro and in soil in the glasshouse.

Example 14

Transgenic *Zea mays* Comprising a Coleopteran Pest Sequence and Additional RNAi Constructs A transgenic *Zea mays* plant comprising a heterologous coding sequence in its genome that is transcribed into an iRNA molecule that targets an organism other than a coleopteran pest is transformed via *Agrobacterium*- or WHISKERS™-mediated transformation to produce one or more insecticidal dsRNA molecules (for example, at least one dsRNA molecule including a dsRNA molecule targeting a gene comprising one of SEQ ID NOs:1-4). Preparations of plant transformation DNA molecules prepared essentially as described in Example 4 are delivered into maize Hi-II suspension cell cultures obtained from a transgenic *Zea mays* plant comprising a heterologous coding sequence in its genome that is transcribed into an iRNA molecule that targets an organism other than a coleopteran pest.

Example 15

Transgenic Coleopteran Pest-resistant Plants

In planta delivery of dsRNA, siRNA or miRNA corresponding to target genes and the subsequent uptake by coleopteran pests through feeding results in down-regulation of the target genes through RNA-mediated gene silencing. When the function of a target gene is important, growth, development, and reproduction of the coleopteran pest is affected, and in the case of at least one of WCR, NCR, SCR, MCR, *D. balteata* LeConte, *D. u. tenella*, and *D. u. undecimpunctata* Mannerheim leads to failure to successfully parasitize, feed, develop, and/or reproduce, or leads to death of the coleopteran pest at one or more stage(s) of development. The choice of target genes and the successful application of RNAi is then used to control coleopteran pests. Five to ten replicates of 10-20 independent $T_1$ *Z. mays* transgenic lines for each RNAi construct are challenged with a corn rootworm species. The challenge is duplicated for each corn rootworm species. $T_1$ seeds of RNAi lines are germinated, and resistant plants transferred to modified Knop's medium 10-15 days after germination. Wild-type control *Z. mays* seeds are germinated at the same time, and used for corn rootworm infection.

There are significantly more (>50%) surviving corn rootworms on controls than on transgenic *Z. mays* lines harboring one or more RNAi constructs. iRNA abundance is measured in corn rootworms feeding on roots of wild-type and transgenic plants using quantitative real-time RT-PCR. There are significantly more iRNA molecules found in transgenic *Z. mays* lines harboring one or more RNAi constructs than in control plants. These results indicate that the transgenic lines process siRNAs corresponding to target genes and that these siRNAs are available for uptake by feeding corn rootworms. More importantly, the results indicate that RNAi-mediated inhibition of all the target genes affects growth, development, and viability of the target corn rootworm. Moreover, RNAi molecules with mismatch sequences with more than 80% sequence identity to target genes affect corn rootworms in a similar way to wild-type sequences. The pairing of mismatch sequence with native sequences to form a hairpin dsRNA in the same RNAi construct delivers plant-processed siRNAs capable of affecting the growth, development and viability of feeding coleopteran pests.

What is claimed is:

1. A method for controlling a coleopteran pest population, the method comprising:
   contacting members of the coleopteran pest population with an agent comprising an inhibitory ribonucleic acid (RNA) molecule expressed from the polynucleotide of SEQ ID NO:109.

2. The method according to claim 1, wherein the inhibitory RNA molecule is expressed from the polynucleotide in a plant cell.

3. A method for controlling a coleopteran pest population, the method comprising:
   providing in a host plant of a coleopteran pest a transformed plant cell comprising the polynucleotide of SEQ ID NO:109 that is transcribed to produce an inhibitory RNA molecule,
   wherein the inhibitory RNA molecule functions upon contact with a coleopteran pest belonging to the population to inhibit the expression of a target sequence within the coleopteran pest.

4. The method according to claim 3, wherein the inhibitory RNA molecule is expressed from the polynucleotide in a plant cell.

5. A method for controlling a coleopteran pest population, the method comprising:
   providing in a host plant of a coleopteran pest a transformed plant cell comprising the polynucleotide of SEQ ID NO:109.

6. The method according to claim 5, wherein the inhibitory RNA molecule is expressed from the polynucleotide in a plant cell.

7. A pest control agent comprising an inhibitory RNA molecule expressed from the polynucleotide of SEQ ID NO: 109, wherein the agent is a topical composition or nutritional composition.

8. A method for controlling a coleopteran pest population, the method comprising:
   providing the pest control agent of claim 7 to the coleopteran pest population.

9. The method according to claim 8, wherein the inhibitory RNA molecule is expressed from the polynucleotide in a plant cell.

* * * * *